United States Patent
Rubbert et al.

(10) Patent No.: US 9,801,697 B2
(45) Date of Patent: Oct. 31, 2017

(54) INTEGRATED SUPPORT DEVICE FOR PROVIDING TEMPORARY PRIMARY STABILITY TO DENTAL IMPLANTS AND PROSTHESIS, AND RELATED METHODS

(71) Applicant: Natural Dental Implants AG, Berlin (DE)

(72) Inventors: Ruedger Rubbert, Berlin (DE); Lea Ellermeier Nesbit, Dallas, TX (US)

(73) Assignee: Natural Dental Implants AG, Berlin (DE)

( * ) Notice: Subject to any disclaimer, the term of this patent is extended or adjusted under 35 U.S.C. 154(b) by 97 days.

(21) Appl. No.: 13/767,999

(22) Filed: Feb. 15, 2013

(65) Prior Publication Data
US 2013/0158694 A1    Jun. 20, 2013

Related U.S. Application Data

(63) Continuation-in-part of application No. 13/247,843, filed on Sep. 28, 2011, and a continuation-in-part of application No. 13/247,607, filed on Sep. 28, 2011.
(Continued)

(51) Int. Cl.
*A61C 8/00* (2006.01)
*G06F 17/50* (2006.01)
(Continued)

(52) U.S. Cl.
CPC ............ *A61C 8/0018* (2013.01); *A61C 5/007* (2013.01); *A61C 5/70* (2017.02); *A61C 8/005* (2013.01); *A61C 8/0012* (2013.01); *A61C 8/0036* (2013.01); *A61C 8/0077* (2013.01); *A61C 9/0046* (2013.01); *A61C 13/0004* (2013.01);
(Continued)

(58) Field of Classification Search
CPC ....................................... A61C 8/0048–8/0078
USPC ............ 433/172–176, 191–195; 700/95–98; 703/2, 6–7; 13/172–176, 191–195
See application file for complete search history.

(56) References Cited

U.S. PATENT DOCUMENTS 2,210,424 A * 8/1940 Morrison ............. A61C 8/0036
433/175
2,792,628 A   5/1957 Neumayer
(Continued)

FOREIGN PATENT DOCUMENTS

DE        2729969 A1     1/1978
DE     197 53 577 A1     6/1999
(Continued)

OTHER PUBLICATIONS

U.S. Appl. No. 11/549,782, filed on Oct. 16, 2008.
(Continued)

*Primary Examiner* — Matthew Nelson
(74) *Attorney, Agent, or Firm* — Bracewell LLP; Kevin R. Tamm

(57) ABSTRACT

Integrated support devices for providing temporary primary stability to a dental prosthesis implant, each individually designed and manufactured for a specific pre-identify patient are also provided. An integrated support device can include a prosthesis interface member configured to connect to an abutment or reduced sized portion of a dental prosthesis/implant. The integrated support device also includes one or more bonding wings for connecting to the adjacent healthy teeth.

29 Claims, 60 Drawing Sheets

Related U.S. Application Data

(60) Provisional application No. 61/602,470, filed on Feb. 23, 2012, provisional application No. 61/454,450, filed on Mar. 18, 2011.

(51) Int. Cl.

| | | |
|---|---|---|
| *A61C 5/00* | (2017.01) | |
| *A61C 9/00* | (2006.01) | |
| *A61C 13/00* | (2006.01) | |
| *A61C 5/70* | (2017.01) | |
| *B33Y 80/00* | (2015.01) | |
| *A61C 8/02* | (2006.01) | |
| *A61C 13/08* | (2006.01) | |
| *A61C 19/06* | (2006.01) | |

(52) U.S. Cl.
CPC ............. *G06F 17/50* (2013.01); *A61C 8/0006* (2013.01); *A61C 8/0075* (2013.01); *A61C 13/0013* (2013.01); *A61C 13/0019* (2013.01); *A61C 13/082* (2013.01); *A61C 19/063* (2013.01); *B33Y 80/00* (2014.12)

(56) References Cited

U.S. PATENT DOCUMENTS

| | | | |
|---|---|---|---|
| 3,717,932 A * | 2/1973 | Brainin | A61C 13/30 433/175 |
| 4,178,686 A | 12/1979 | Riess et al. | |
| 4,199,864 A | 4/1980 | Ashman | |
| 4,431,416 A * | 2/1984 | Niznick | A61C 8/0018 433/174 |
| 4,531,566 A | 7/1985 | Boettcher | |
| 4,552,779 A * | 11/1985 | McClure | A61C 13/26 106/35 |
| 4,684,555 A | 8/1987 | Neumeyer | |
| 5,002,488 A | 3/1991 | Homsy | |
| 5,004,422 A * | 4/1991 | Propper | A61C 8/0036 433/175 |
| 5,080,589 A * | 1/1992 | Oden | A61O 5/002 433/202.1 |
| 5,264,215 A * | 11/1993 | Nakabayashi | A61L 24/0084 424/423 |
| 5,556,280 A * | 9/1996 | Pelak | A61C 8/0048 433/172 |
| 5,562,450 A | 10/1996 | Gieloff et al. | |
| 5,725,378 A | 3/1998 | Wang | |
| 5,921,778 A * | 7/1999 | Karmaker | A61O 5/00 433/215 |
| 5,944,524 A * | 8/1999 | Hill | A61L 27/06 433/173 |
| 6,099,313 A | 8/2000 | Dorken et al. | |
| 6,238,601 B1 * | 5/2001 | Salomonson | A61O 5/10 156/182 |
| 6,250,923 B1 | 6/2001 | Gibbs et al. | |
| 6,447,295 B1 | 9/2002 | Kumar et al. | |
| 6,534,197 B2 | 3/2003 | Noda et al. | |
| 6,696,073 B2 * | 2/2004 | Boyce | A61B 17/0401 424/422 |
| 6,702,855 B1 | 3/2004 | Steinemann et al. | |
| 6,755,651 B2 | 6/2004 | Brodbeck | |
| 6,984,261 B2 | 1/2006 | Cummings et al. | |
| 7,377,782 B1 * | 5/2008 | Brosnihan | A61C 7/08 128/861 |
| 7,708,557 B2 | 5/2010 | Rubbert | |
| 8,753,118 B2 * | 6/2014 | Randall | A61C 8/0048 433/181 |
| 2001/0055745 A1 * | 12/2001 | Gault | A61C 8/0012 433/201.1 |
| 2003/0064349 A1 | 4/2003 | Simmons, Jr. | |
| 2004/0029068 A1 | 2/2004 | Sachdeva et al. | |
| 2004/0110110 A1 * | 6/2004 | Chishti | A61C 7/00 433/24 |
| 2004/0152034 A1 | 8/2004 | Cummings et al. | |
| 2004/0185418 A1 | 9/2004 | Schulter | |
| 2004/0197727 A1 * | 10/2004 | Sachdeva | A61C 7/00 433/24 |
| 2005/0038498 A1 * | 2/2005 | Dubrow | A61L 31/14 623/1.15 |
| 2005/0048440 A1 * | 3/2005 | Feng | A61C 8/0036 433/175 |
| 2005/0084513 A1 | 4/2005 | Tang | |
| 2006/0078847 A1 * | 4/2006 | Kwan | A61C 8/0001 433/174 |
| 2006/0105295 A1 * | 5/2006 | Mayer | A61B 17/68 433/173 |
| 2007/0015110 A1 | 1/2007 | Zhang et al. | |
| 2007/0264612 A1 * | 11/2007 | Mount | A61C 8/00 433/173 |
| 2008/0090208 A1 | 4/2008 | Rubbert | |
| 2009/0042167 A1 | 2/2009 | Van Der Zel | |
| 2009/0087817 A1 | 4/2009 | Jansen | |
| 2009/0319068 A1 | 12/2009 | Sager | |
| 2010/0086895 A1 * | 4/2010 | Randall | A61C 8/0048 433/172 |
| 2010/0203478 A1 | 8/2010 | Rubbert | |
| 2010/0261141 A1 | 10/2010 | Ajlouni | |
| 2011/0008754 A1 * | 1/2011 | Bassett | A61C 8/0012 433/175 |
| 2011/0086326 A1 * | 4/2011 | Gwon | A61C 13/275 433/172 |
| 2012/0064489 A1 | 3/2012 | Rubbert | |
| 2012/0065756 A1 | 3/2012 | Rubbert | |

FOREIGN PATENT DOCUMENTS

| | | |
|---|---|---|
| DE | 10020894 | 4/2000 |
| DE | 103 58 680 A1 | 7/2005 |
| EP | 1073381 | 11/1999 |
| EP | 1150620 | 8/2000 |
| EP | 2 025 303 A1 | 2/2009 |
| WO | 2009020447 | 2/2009 |

OTHER PUBLICATIONS

U.S. Appl. No. 11/724,261, filed on Mar. 15, 2007.
U.S. Appl. No. 12/763,001, filed on Apr. 19, 2010.
U.S. Appl. No. 13/247,843, filed on Sep. 28, 2011.
U.S. Appl. No. 13/247,607, filed on, Sep. 28, 2011.
Non-Final Office Action issued in co-pending U.S. Appl. No. 12/247,843; dated Aug. 29, 2013; 34 pages.
A Goerig, "Successful International Reimplantation of Mandibular Molars," Quintessence Int'l, vol. 19, No. 8, 1998.
K. Wong, "Exarticulation and Reimplantation Utilizing Guided Tissue Regeneration: A case report," Quintessence Int'l, vol. 33, No. 2, 2002.
E. Nuzzolese, "International Dental Reimplantation: A Case Report," Journal of Contemporary Dental Practice, vol. 5, No. 3, Aug. 15, 2004.
Search Report for Related Application PCT/EP2013/053246 dated Jun. 28, 2013.

\* cited by examiner

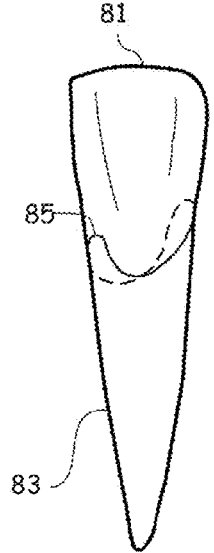
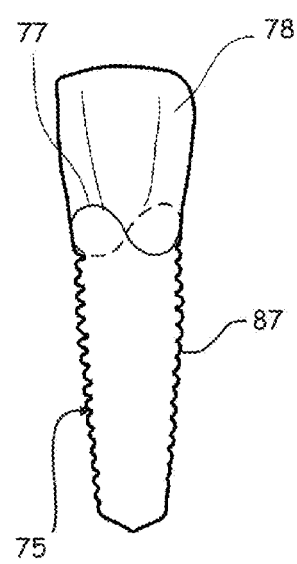
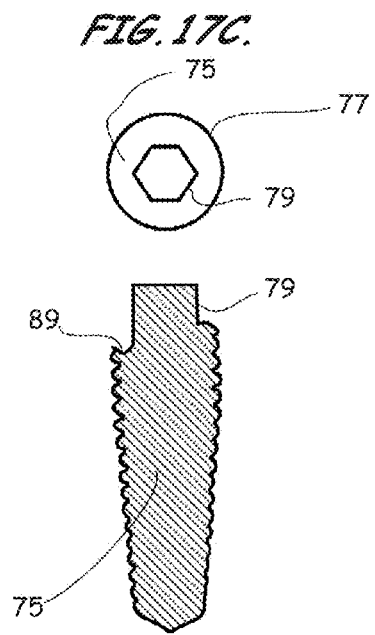
FIG. 18.     FIG. 17A.     FIG. 17B.
FIG. 17C.

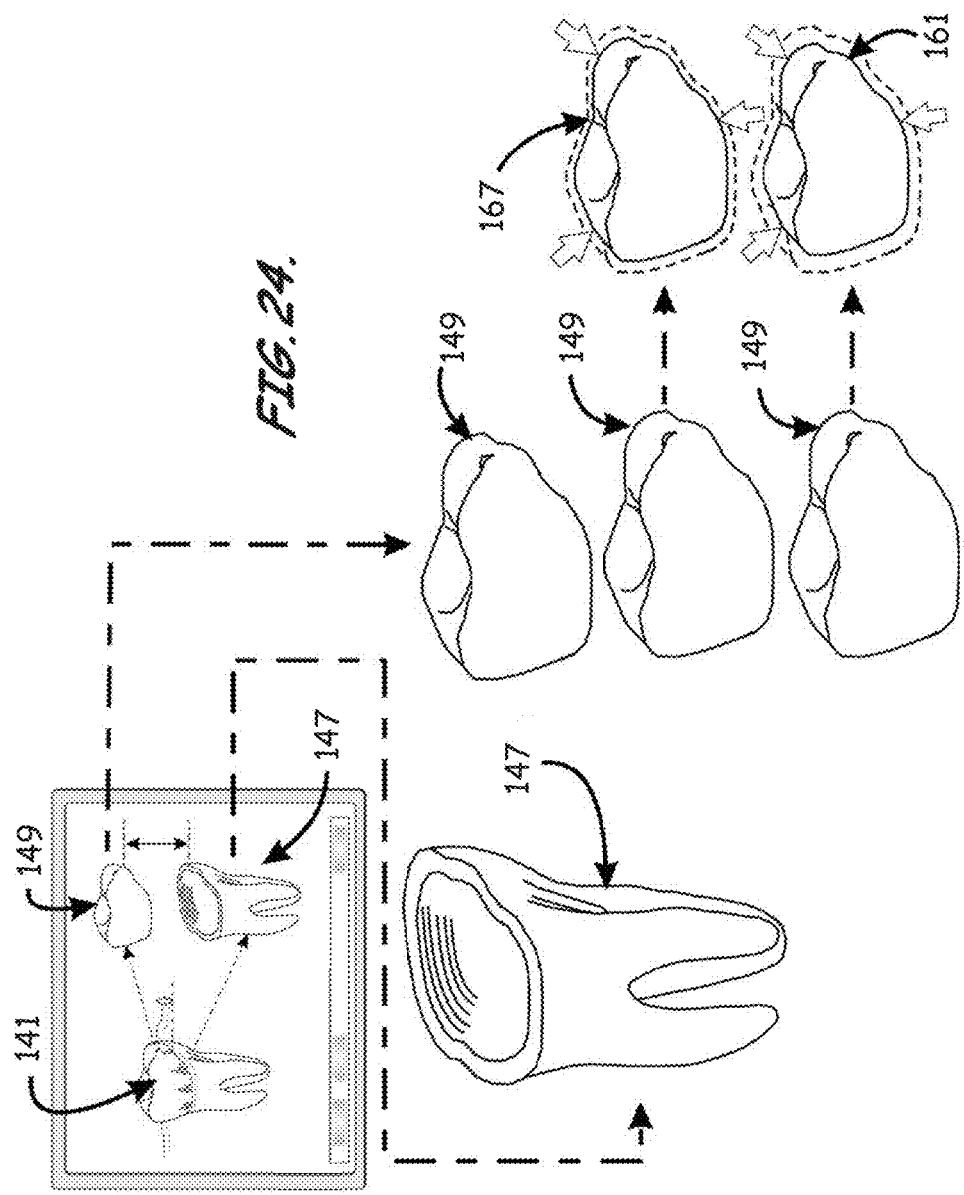

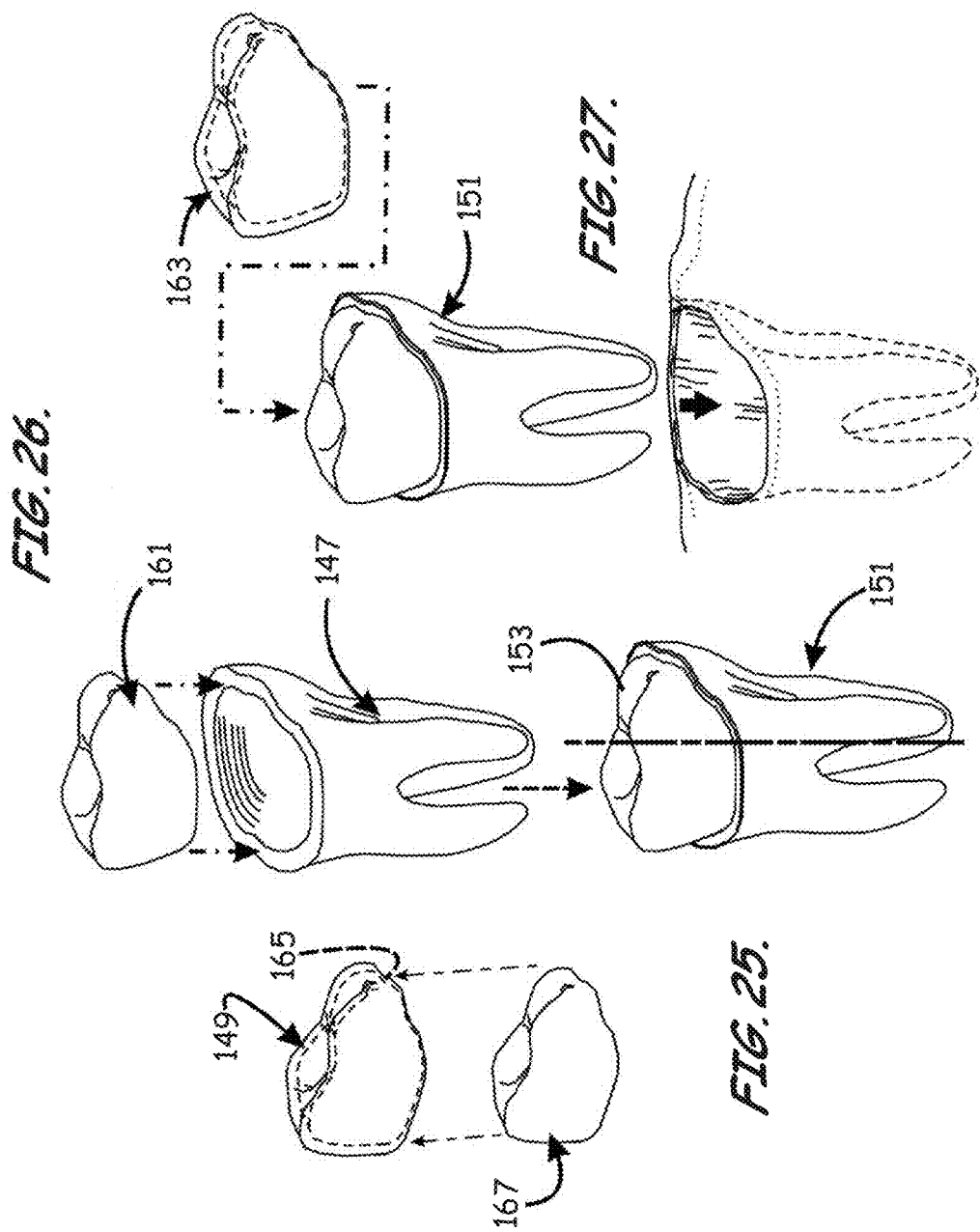

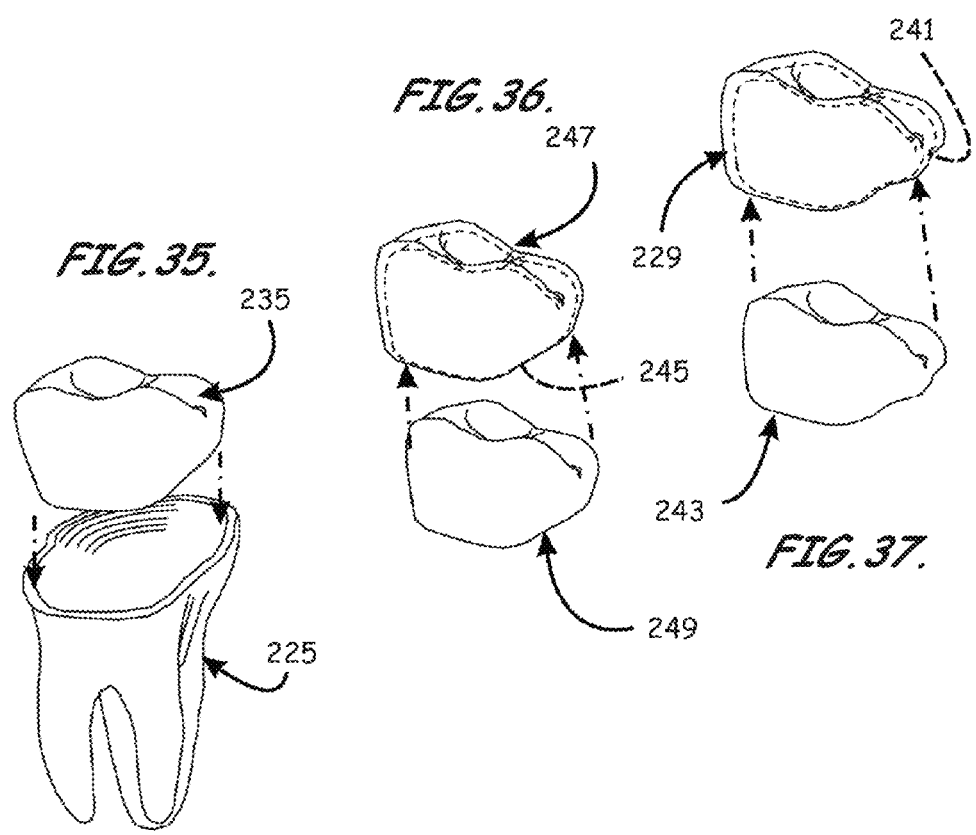

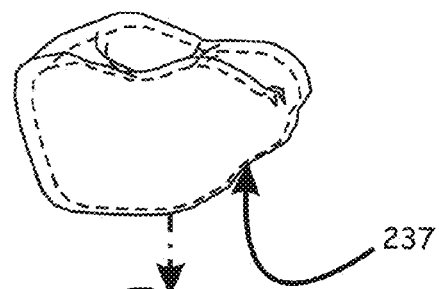
FIG. 38.
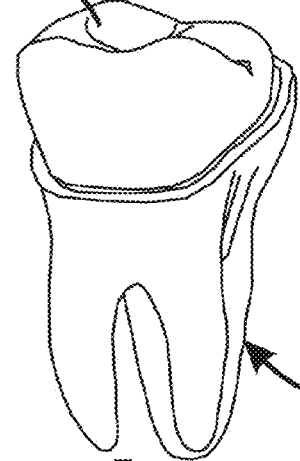
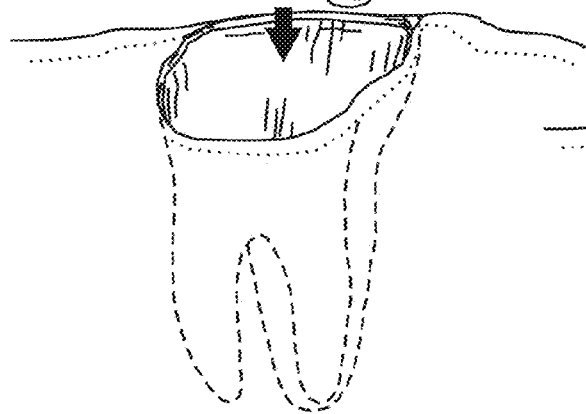
FIG. 39.
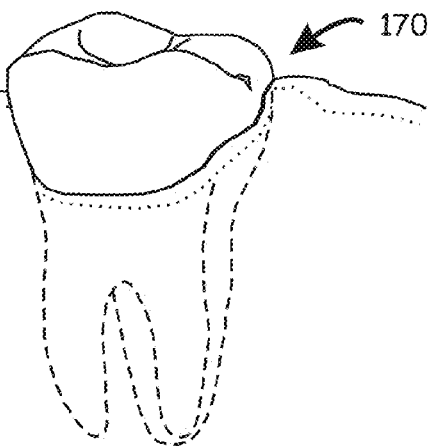

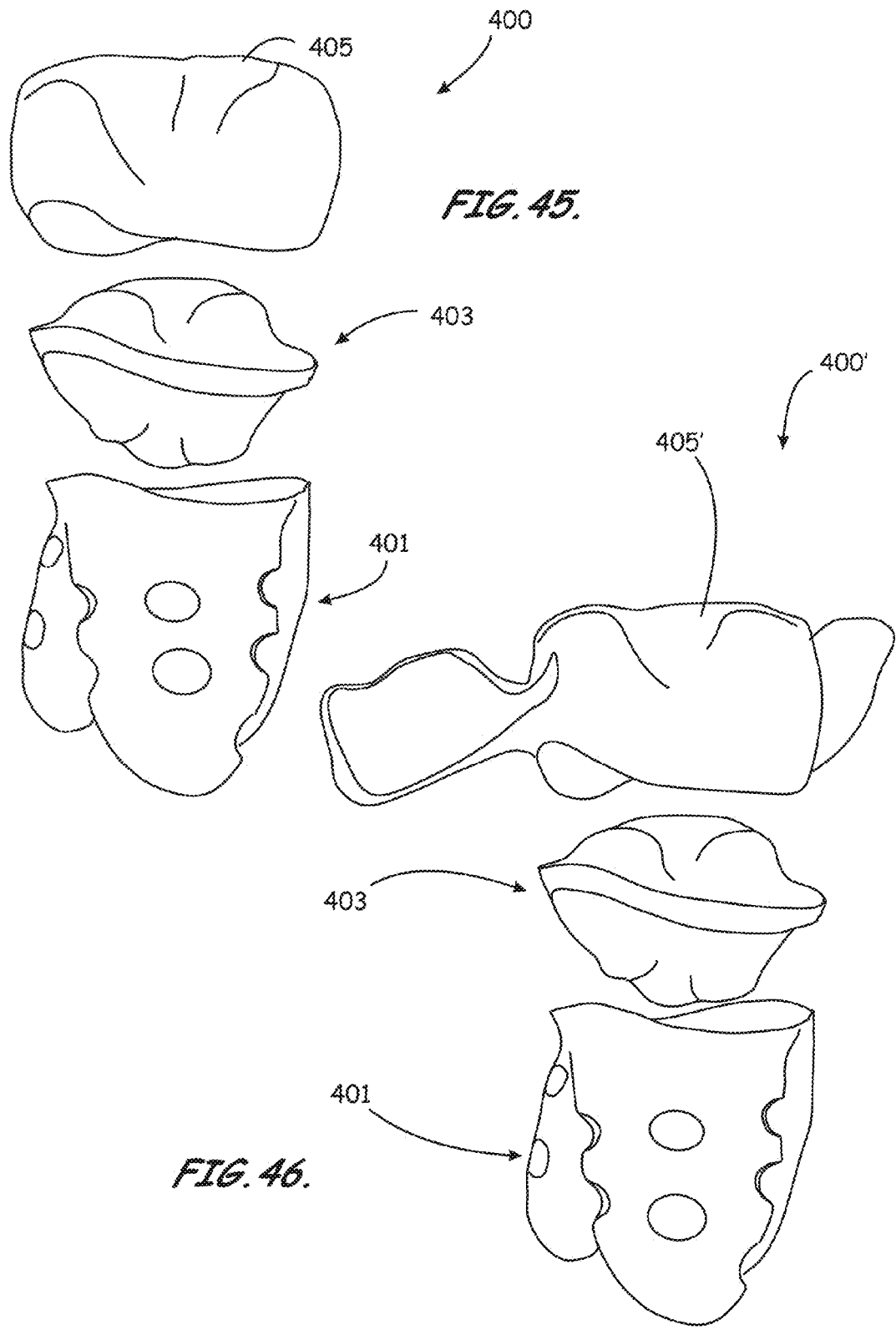

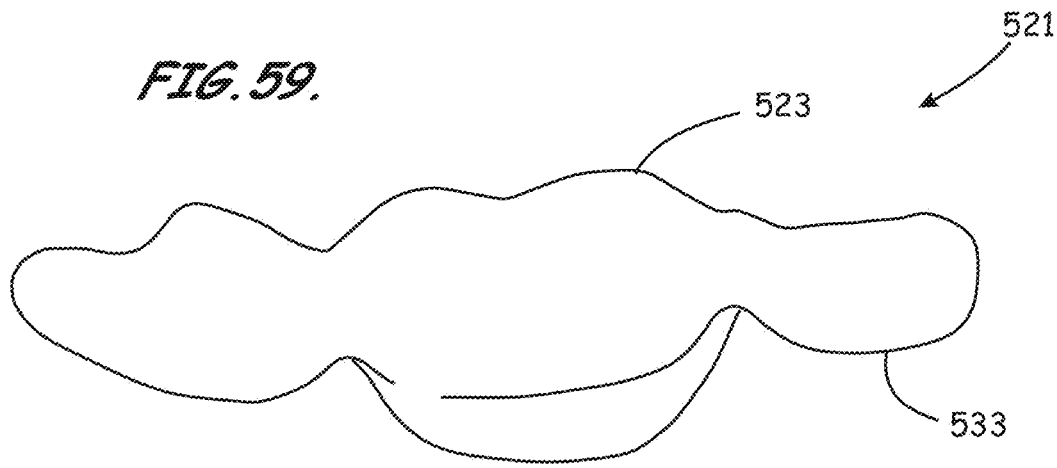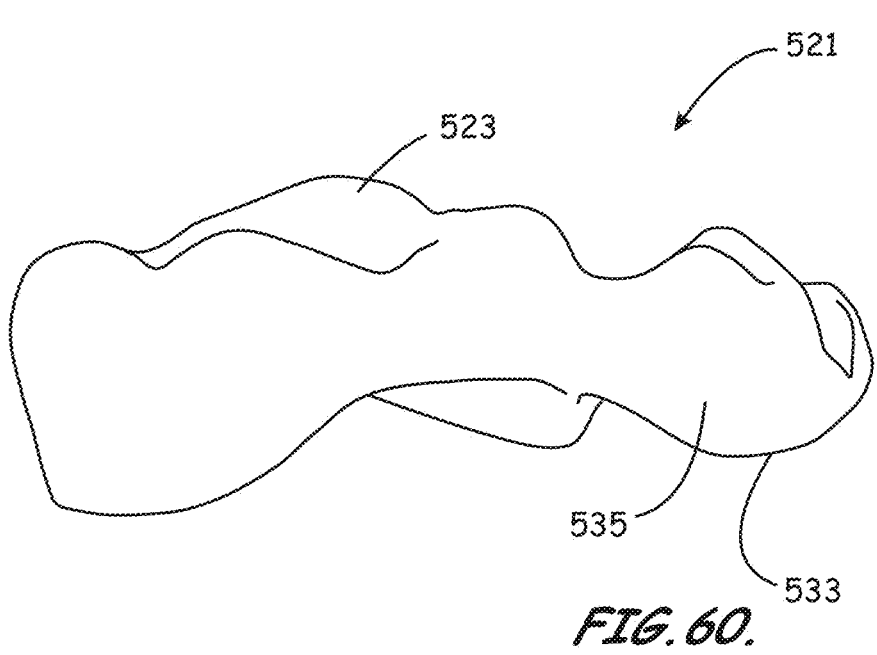

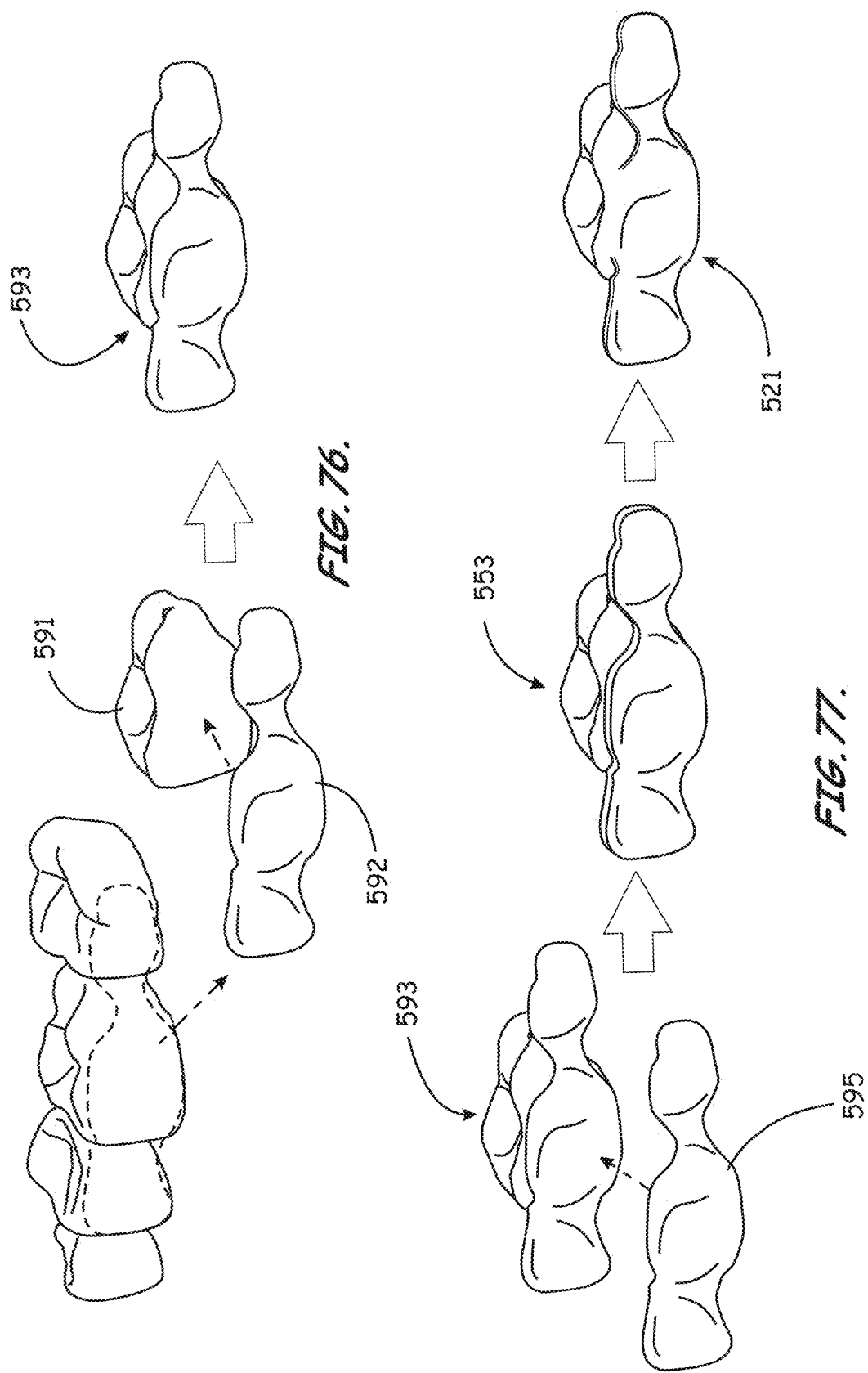

INTEGRATED SUPPORT DEVICE FOR PROVIDING TEMPORARY PRIMARY STABILITY TO DENTAL IMPLANTS AND PROSTHESIS, AND RELATED METHODS

RELATED APPLICATIONS

This patent application is a non-provisional of and claims priority to and the benefit of U.S. Provisional Patent Application No. 61/602,470 filed on Feb. 23, 2012, and is a continuation in-part of U.S. patent application Ser. No. 13/247,843, filed Sep. 28, 2011, and U.S. patent application Ser. No. 13/247,607, filed Sep. 28, 2011, which claimed priority to and the benefit of U.S. Provisional Patent Application No. 61/454,450 filed on Mar. 18, 2011; and is related to U.S. patent application Ser. No. 13/767,981, concurrently filed on Feb. 15, 2013, and U.S. patent application Ser. No. 12/763,001, filed Apr. 19, 2010, which is a continuation-in-part of and claimed priority to and the benefit of U.S. patent application Ser. No. 11/724,261, filed Mar. 15, 2007, now U.S. Pat. No. 7,708,557, which is a continuation-in-part of and claimed priority to and the benefit of U.S. patent application Ser. No. 11/549,782 filed on Oct. 16, 2006, each incorporated by reference in its entirety.

BACKGROUND OF THE INVENTION

Field of the Invention

The invention relates generally to the field of dentistry, and more particularly to the field of dental restorations, implants and prostheses. The invention further relates to computer assisted and conventional systems and methods for designing and manufacturing such custom dental prosthesis.

Description of Related Art

Human teeth serve a variety of functions. Not only are they important for chewing food, but they also necessary to properly pronounce certain consonants, especially fizzle- and S-sounds. Furthermore, teeth play a major role in our personal appearance. Healthy and well aligned teeth are an ideal of beauty and appear as a cosmetic sign of youth and success.

Although various preventive measures, like frequent tooth brushing and flossing, and drinking fluoridized or iodized water are widely accepted and used, the great majority of people are sooner or later challenged with dental fillings, restorations implants, and/or other prostheses.

A major goal in dentistry is to postpone loss of teeth as long as possible. Another goal is certainly to provide comfortable prostheses with a broad scope/indication and a long lasting life-time.

Generally, the number of available restorative and prosthetic options is limited. Typically fillings, inlays, and crowns are used if the root and its embedding periodontal structure are healthy, and sufficient as support for such restorative partial prostheses. Traditionally, if the original tooth can no longer be used; the use of bridges or non-customized osseointegrated implants is indicated. In this context, several negative aspects are to be endured. In order to provide the support structure for a bridge, adjacent teeth are ground, and healthy enamel is partially destroyed. With osseointegrated implants, the gingiva-implant interface is often the cause of chronic local infection. Removable dentures, generally considered the final prosthetic option, have severe functional limitations and significant maintenance requirements.

When a tooth is partially damaged, either by caries or mechanical impact, the missing portion should in most cases be replaced. As long as a tooth provides enough structural strength to support a prosthesis, for example, an inlay or a crown, this will typically be the preferred solution. However, if the loss of tooth substance is severe, this may not be applicable. In these cases, a bridge can be applied, enduring the aforementioned negative consequences. Another option is to replace the tooth with an implant.

There are many methods or options for replacing missing teeth. Off-the-shelf or pre-shaped osseointegrated dental implants are one of the options. Osseointegration means the direct contact of the implant surface with the bone without a fibrous connective tissue interface (natural teeth are typically not in direct contact with the bone, but are connected to the bone by ligaments). The use of such dental implants includes a wide variety of implant designs and materials, use of implants in different locations in the mouth and use of a variety of surgical protocols.

Endosteal, also called endosseous implants, are placed into the bone like natural tooth roots. They can provide an anchor for one or more artificial teeth. They are the most commonly used type of implants. There are various types of endosteal implants, for example, screws, cylinders, cones, plates and blades. The generic screw, cylinder and cone types of implants are sometimes called "root-form" type. Such generic root-form implants that replace a single tooth generally consist of three parts, the actual implant-root for osseointegration, an abutment, and the artificial crown. The interfaces between the three aforementioned parts are critical in respect to the sealing quality between said three parts. Bacterial infections can be caused if the sealing is compromised in regards to its short, mid and long-term stability.

Such three-part implant designs have a first sub-gingival joint between the implant screw and the abutment. The first joint is in its height placed adjacent to the bone crest of the jaw of the implant-receiving patient. The second joint is placed iso- or supra-gingival, which means on the same vertical height of the mouth facing surface of the gingiva or beyond the trans-gingival portion of the overall implant design. The first joint between the implant screw and abutment is especially under the static and dynamic stress of mastication forces, and is identified as an area where bacteria may congregate, causing a chronic infection. This chronic infection is sometimes called "periimplantitis."

Sometimes implant designs that actually consolidate two of said three parts (e.g., the implant-root to be osseointegrated and the abutment) are referred to as one-piece implants. Contrary hereto, the term "one-piece" implant as used hereinafter is meant to refer to the integration of all three parts: the implant root, the abutment, and the crown. The term "immediate placing" of an implant is used if the integration of the implant into the jaw occurs a short term after the extraction of a tooth. If such implants have a reasonable initial contact stability with the bone directly after being inserted (referred to as primary stability), then such implants are available for so called "immediately load", which means that the osseo-integrative stability, or secondary stability, does not need to be developed before performing the following process steps: making an impression of the abutment part of the implant in conjunction with the gingiva and the adjacent teeth situation, then fabricating the crown, implementing the crown, and actually allowing the patient to use the implant for functional load, including mastication.

Subperiosteal implants are implants that are placed over the bone in cases where the bone has atrophied and jaw structure is limited. Subperiosteal implants are customized metal frameworks, providing the equivalent of multiple tooth roots. They can be applied in a limited area or in the entire mouth. After application, natural tissue membrane and/or bone will grow back around the implant, thus providing more stability. Posts are positioned to protrude through the gum to hold the prosthesis.

Traditionally, submerged osseointegrated dental implants are placed in bone and covered by mucosa during the immediate post-operative healing period. At four to eight months, a second surgical procedure is performed to expose the implant so it may be loaded first with various types of abutments and second with various types of dental crowns. In recent years, immediate non-submerged implant placement following tooth extraction and immediate abutment and crown loading after surgical placement has become more common.

Generic ceramic dental implants are available made from yttrium-stabilized zirconia ceramics. Although such ceramic materials are, due to its internal crystal structure and mechanisms, able to suppress micro-cracks, it has been reported in the industry that in the moist-warm environment of the human body, the long term stability of yttrium-stabilized zirconia ceramics and conventional dental implants is considered compromised to the extent that respective dental implants cannot be considered fracture-safe for the life-time expectations established.

The success rate and the in-vivo life time of non-customized osseointegrated dental implants are limited, and the surgical procedure is heavily invasive, because the bone needs to be drilled or ground in order to be adapted to the shape of the non-customized implants. Furthermore, osseointegrated implants are a limiting factor in a later orthodontic treatment. Problems relating to nerve transposition, osseous grafting, ridge augmentation, and sinus augmentation of osseointegrated dental implants, and/or to tissue health adjacent to dental implants have also been reported. Patients often complain about chronically infected periodontal structure caused by osseointegrated implants.

In cases where a tooth is not severely damaged, and would be ready to receive a partial restoration but an intra-oral repair is impossible due to access problems, or a reverse root canal treatment is required, an alternative method is the intentional re-implantation. The tooth is extracted, repaired, and re-integrated into the existing periodontal or perio-type structure of a dental patient. A disadvantage relating to such techniques is certainly that the specific tooth to be reimplanted or transplanted still needs an overall reasonable condition and prognosis to justify an intentional re-implantation and that only certain root and root canal deficiencies can be repaired this way.

U.S. Pat. No. 5,562,450 references as prior art the German application DE 27 29 969 A1, incorporated herein by reference in its entirety, which describes osseointegration of an implant that is substantially a copy of an extracted human tooth fabricated by a process involving copy milling. In order to be successfully osseointegrated, the connective tissue (e.g., ligament) remaining in the extraction socket needs to be removed by being scraped out or curetted. The '450 patent recognizes the need to create a compression pressure between the bone and the implant in order to reach reasonable primary stability of the implant and teaches to dimensionally enlarge the anatomical shape of the implant over the extracted tooth to fill the extraction socket.

Rubbert and Berndt reference in the article "Topologically Structured Surfaces and Coating Treatments for Periodontal and Osseo-Integration" published on Apr. 7, 2009, which is incorporated herein by reference in its entirety, various aspects of surface condition and treatments of dental implants and prostheses.

U.S. Pat. No. 6,099,313 discloses a dental implant for osseointegration having a bone-contact section which is root-shaped with an apical extension and an abutment described as a build-up section for fastening a crown.

All such restorative and prosthetic options and methodologies are deficient—being heavily invasive and/or limited in their respective scope. There has not been recognition, until now by the inventors, of the need for a product, systems, and methods related to the integration of dental prosthesis such as artificial tooth, bridges, or segments of the dentition that includes custom-shaped root structures, custom-shaped abutments, custom joints connecting a custom abutment to a custom-shaped root structure and/or a custom-shaped crown structure or portion of an integrated support structure, custom-made positioning and fixation integrated support structures for achieving primary stability, or a fabrication process whereby the root-shaped custom portions of the prosthesis are based on anatomical imaging data received prior to the extraction of the tooth or of the teeth of interest or directly of the alveolar situation.

In addition, recognized by the inventors, there is the need for a dental prosthesis and implementation methods which utilizes advanced ceramic materials, manufacturing technologies to increase the density and/or thickness of ceramic materials to its theoretical degree to be considered fracture-safe for use as dental implants or prostheses, metal-ceramic diffusion bonding and hot-bonding technologies to overcome bacterial issues developing on the sub-gingival joints of traditional 2-part and 3-part implant designs, and tissue engineering methods for osseointegration and perio-type integration to enhance the clinical integration of prostheses designed and manufactured according to the inventions disclosed herein as further advantageous embodiments not previously recognized until now.

The shape design of mass-produced implants shows a standardized joint between the implant and the crown portion. While the crown is usually custom-shaped to the adjacent and opposite teeth, the implant is not. Therefore, the joint between such traditional crowns and implants is non-customized. Such joints are usually shaped with standardized cylindrical, hexagonal, and conical shape portions. In order to try to obtain a positive lock between the implant and the crown, numerous standard form joints are manufactured in order to try to cover a majority of the possible crown designs. This, however, results in significant additional manufacturing costs and difficulties in inventory management. Alternatively, a smaller number of "standard" designs are manufactured designed to cover most cases. Although the smaller number helps reduce inventory management problems and manufacturing costs, it has been found too often to lead to inadequate joint connections and in an increased number of suboptimal situations, as the clinician is often provided an improperly suited connection. That is, the joint having a smaller footprint than ideal is often employed in order to allow for adjustments due to the inadequate connection. Recognized, therefore, by the inventors is the need for a custom joint which can provide a good positive lock between the implant and the crown or respectively between the implant and the abutment, which can maximize the "footprint" between the connecting pieces, and which can also be adapted to the geometrical limitations of the overall available envelope for the single tooth prosthesis.

The product, and related systems and methods provided by embodiments of the present invention or inventions comprise several independent inventive features providing substantial improvements to conventional devices and processes. The greatest benefit will be achieved for dental treatments—especially for patients requiring tooth replacement.

SUMMARY OF THE INVENTION

In view of the foregoing, various embodiments of the present invention beneficially provide an integrated support device for providing temporary stability to customized dental prosthesis and implants that are designed and manufactured based on a process or processes. Various embodiments also provide dental implant assemblies that incorporate integrated support devices for providing temporary primary stability to the dental implant/prosthesis. An exemplary integrated support device includes a crown-like prosthesis interface member configured to engage and land atop and surround substantial portions of the occlusal extending rising of the transgingival interlock abutment to stabilize and provide temporary primary stability to the dental implant at a user desired position and inclination when the dental implant is positioned in the jaw cavity of the pre-identified patient. The integrated support device further includes at least one bonding wing at least substantially, if not completely (within tolerances) rigidly connected to the prosthesis interface member and configured to bond to a corresponding at least one adjacent functional tooth when operably positioned thereon. Advantageously, the integrated support device can be shaped into its final form prior to insertion of the dental implant into the jaw bone cavity.

As an exemplary embodiment of the present invention, the crown portion of the aforementioned prosthesis forms one part with one or more bonding wings to form an integrated support device. That is, according to the exemplary embodiment, the integrated support device provides a prosthesis interface member (e.g., in the form of a temporary crown portion) similarly configured as described above, to engage and land atop and surround substantial portions of an occlusal extending rising of an abutment connected to or being an integral part of a dental implant of a dental prosthesis positioned within a jawbone cavity of a pre-identified patient, to provide a form lock fit with the occlusal extending rising. According to an exemplary configuration, the prosthesis interface member is slightly undersized to reduce occlusal-occlusal contact.

The device also includes the one or more bonding wings configured to bond to a corresponding adjacent functional tooth when operably positioned thereon to at least substantially rigidly fixate the prosthesis interface member. According to the exemplary configuration, the bonding wing is dimensioned to be sufficiently small so as to not extend atop a portion of an incisal surface of the respective adjacent functional tooth or teeth that is/are normally aligned to contact a surface of a corresponding opposite-facing functional tooth when the respective tooth is an anterior tooth, and so as to not extend atop a portion of an occlusal surface of the respective adjacent functional tooth or teeth that is/are normally aligned to contact an occlusal surface of a corresponding opposite-facing functional tooth when the respective tooth is a posterior tooth. That is, portions that extend atop the tooth do not extend over portions of the tooth that normally contact an opposing tooth.

According to the exemplary configuration, each bonding wing includes a tooth-facing outer surface portion having a custom three-dimensional surface shape dimensioned to substantially match a three-dimensional shape of the outer surface portion of the crown of the adhesively engaged adjacent functional tooth. According to the exemplary configuration, the tooth-facing outer surface portion is manufactured to provide the custom three-dimensional surface shape prior to insertion of the dental implant into the jawbone, prior to application of bonding material to the tooth-facing outer surface portion, and prior to bonding attachment of the tooth-facing outer surface portion to the outer surface portion of the crown of the adjacent functional tooth, determined using imaging data.

Advantageously, the integrated support device functions to maintain the interlock abutment and the implant portion or the integrated implant that includes a transgingival portion at a user desired position and inclination having a geometrical relation to one or more adjacent functional teeth (adjacent the receiving jawbone cavity) to stabilize and provide the primary stability to the dental implant. According to the exemplary configuration, the prosthesis interface member (e.g., temporary crown portion) and bonding wings are removably configured such that the entire device can be removed when the implant portion of the prosthesis is fully integrated in the extraction socket. After removing the integrated support device, a final or permanent crown configured, for example, as described above, can be placed on the, e.g., one-part implant.

Various embodiments of the present invention provide methods of designing and manufacturing the integrated support device for a dental prosthesis to replace a non-functional tooth of a pre-identified patient. An example of a method includes the step of designing the integrated support device to stabilize and provide primary stability to a dental implant portion of the dental prosthesis when the dental implant is positioned within a jawbone cavity of the pre-identified patient, and providing design data to a fabrication machine to produce the integrated support device. According to an exemplary configuration, the step of designing the integrated support device includes the steps of receiving data describing a three-dimensional surface shape of at least portions of the specific non-functional natural tooth of a pre-identified patient to be replaced by a dental prosthesis, and/or the occlusal extending portion of the dental prosthesis. The steps also include forming a virtual prosthesis component interface model modeling outer dimensions of an occlusal extending recess extending within a body of a prosthesis interface member, and forming a virtual prosthesis component model modeling an outer surface of an occlusal facing dental prosthesis component to define at least an occlusal-facing outer surface portion of a prosthesis interface member.

The steps also include connecting the virtual prosthesis component interface model with the virtual prosthesis component model to form a virtual prosthesis interface member model modeling the prosthesis interface member. The modeled prosthesis interface member advantageously has a corresponding occlusal facing recess extending into a body of the prosthesis interface member and shaped to interface with the occlusal extending portion of the dental prosthesis, the prosthesis interface member configured to engage and land atop and surround substantial portions of the occlusal extending portion of the dental prosthesis.

The steps further include forming a virtual bonding wing model modeling a bonding wing having a tooth-facing surface configured to bond to a corresponding adjacent functional tooth adjacent the jaw bone cavity when operably positioned thereon to at least substantially rigidly fixate the prosthesis interface member, and connecting the virtual bonding wing model with the virtual prosthesis interface member model to form a virtual integrated support device model modeling the integrated support device. According to the exemplary configuration the step of forming a virtual bonding wing model includes the steps of receiving data describing a three-dimensional surface shape of at least portions of a crown of the adjacent functional tooth adjacent the job of cavity of the pre-identified patient, and employing skin models of the three-dimensional surface shape of the adjacent functional tooth to define a corresponding three-dimensional surface shape of the tooth-facing surface of the virtual bonding wing model, and according to the preferred configuration, to form the non-tooth-facing surface.

The step of designing the integrated support device further includes connecting the virtual bonding wing model with the virtual prosthesis interface member model to form a virtual integrated support device model modeling the integrated support device. Alternatively, the bonding wing and the prosthesis interface member models can be provided separately to the fabrication equipment.

In an alternative embodiment of the present invention, a splint is provided which comprises recesses formed as holes. These holes enhance the adhesive in attaching the splint to the prosthesis and its adjacent teeth. In a further embodiment of the present invention, the aforementioned splint is attached only to one of the adjacent teeth. This splint can be used in cases where only one of the adjacent teeth is capable of providing primary stability to the prosthesis via the splint. If the other adjacent tooth is not qualified for a splint to be attached, this splint design can be utilized. The recesses described herewith and the configuration whereby the bonding wing is attached only to one of the adjacent teeth, can also be employed with the integrated support device, which is described, for example, as a temporary crown and splint formed as one integrated part.

For a situation in which the directly adjacent teeth of the prosthesis are both not capable for a splint to be attached to, a splint is proposed which attaches to the teeth next to the adjacent teeth. This specifies a possibility for providing primary stability to the prosthesis by utilizing the teeth next to the adjacent teeth. Such a splint can be of particular importance if the directly adjacent teeth are not capable of providing sufficient primary stability. Also, the implementation of a bonding wing that covers the teeth next to the adjacent teeth can be utilized with the integrated support device concept. In another embodiment of the invention the splint is not directly adhesively connected to the temporary crown or the permanent crown but connected by/through a detachable connection mechanism, having an attachment that is either a separate part or an integrated part of the temporary or permanent crown, whereby the splint attaches to the connection geometry of the attachment e.g. by means of a screw or one or more cotter-pins. This concept of a detachable connection mechanism can be alternatively or additionally employed for the affixation of the splint to the adjacent teeth so that the attachments are adhesively bonded to the adjacent teeth prior to the extraction of the tooth to be replaced by a dental prosthesis according to an embodiment of the invention. Then, after extraction, the prosthesis can be affixed though the splint (e.g. screwed or pinned) to the pre-installed attachments, eliminating the need to perform an adhesive bonding procedure adjacent the extraction wound. In an alternative embodiment, the detachable affixation affixed to the adjacent teeth is combined with the integrated support device to the extent that the bonding wings are configured to support the detachable mechanism—e.g. by having a corresponding form fit to the attachments for accurate positioning of the prosthesis and e.g. a detachable mechanical component by means of screws or cotter-pins.

Various embodiments of the present invention also provide dental implant assemblies/apparatus and methods of manufacturing or otherwise providing a custom prosthesis interface having a three-dimensional surface shape positioned and formed to create a form locking fit with respect to the crown/abutment combination and the implant body and/or respectively between the crown/splint combination and the abutment/implant combination, which can maximize or at least significantly increase the footprint of each such locking fits, which can reduce and/or eliminate collisions between manufactured components, and which allows just-in-time use of the fully customized components or individualized stocking—eliminating the need to manufacture, offer and provide multiple potential versions of such joints.

For example, a dental implant assembly to replace a nonfunctional natural tooth positioned in a jawbone of a specific pre-identified patient according to an embodiment of the present invention can include a dental implant body having a occlusal projecting custom shaped prosthesis interface formed therein to receive an occlusally-facing dental prosthesis component having a complementing interface surface. The prosthesis interface has a three-dimensional surface shape/contour positioned and formed to create a form locking fit with respect to the occlusally-facing dental prosthesis component when connected thereto. The dental implant body can be a unitary piece or an integrated/attached assembly of an implant portion and an abutment portion and respectively the occlusally-facing dental prosthesis component can be either a crown or a separate abutment or an integrated/attached assembly including an abutment portion and a crown portion. The prosthesis interface can also have an asymmetrically contoured outward facing edge having a shape correlated to a shape of a gum line of the specific pre-identified patient. The separate abutment can also include an apical projecting custom shaped second prosthesis interface form to receive a root body portion of the dental implant having a complementing interface surface. The second prosthesis interface has a three-dimensional surface shape positioned and formed to create a form locking fit with respect to the root body portion when connected thereto. The three-dimensional surface shape of either or both prosthesis interface can also be substantially asymmetrically shaped and substantially devoid of concentric convolutionally shaped segments with respect to a longitudinally extending axis of the dental implant. The abutment can be a ceramic (including, e.g., zirconia or alumina or a combination thereof) of sufficient thickness to be considered fracture-safe. This can provide a significant advantage over ceramic abutments which, rather than extend into the root portion, receive an occlusal-facing projection of the root body, as the much thinner structure is significantly more prone to fracture.

According to another embodiment of the present invention, a dental implant assembly can include a dental implant providing the root portion of the implant assembly, an occlusal-facing dental prosthesis component providing, for example, a permanent or temporary crown, and a transgingival interlock abutment connecting the dental implant with the occlusal-facing dental prosthesis component. The transgingival interlock abutment includes a body having an occlusal extending rising having an asymmetrical custom three-dimensional surface shape substantially directly correlated with an asymmetrical custom three-dimensional surface shape of an occlusally facing surface of an occlusal-facing dental prosthesis component of the dental prosthesis, and a dental anatomy of the specific pre-identified patient, and can also or alternatively include an apical extending rising having an asymmetrical custom three-dimensional surface shape directly correlated to an asymmetrical custom three-dimensional surface shape of one or more of the following: an apical facing surface of an apical-facing dental implant, an apical extending recess extending substantially into a main body of the dental implant, and/or a dental anatomy of the specific pre-identified patient. Advantageously, according to an exemplary configuration, the trans-gingival interlock abutment is mainly composed of a relatively thick unitary piece of ceramic material configured and shaped to resist micro-cracks such that the dental prosthesis can resultantly be considered fracture-safe for life-time expectations.

According to an embodiment of the abutment, the three-dimensional surface shape of the occlusal extending rising can include a substantial asymmetric negative indent recessed into the occlusal facing surface of the occlusal extending rising. Advantageously, such design can enhance structural integrity of the crown resulting from a corresponding asymmetric negative indent in the crown portion, itself. Also or alternatively, the occlusal facing surface of the occlusal extending rising can have an asymmetrical custom-shaped surface contour directly correlated to an inner surface contour of an occlusal extending recess extending substantially into a body of the occlusal-facing dental prosthesis component. The occlusal extending recess can beneficially define a complementing interface surface, whereby the occlusal facing surface of the occlusal extending rising and the complementing interface surface of the dental prosthesis component together create a form-lock fit. Additionally, the occlusal extending recess can have a three-dimensional asymmetric shape directly correlated with a three-dimensional asymmetric shape of substantial portions of the occlusal facing surface of the dental prosthesis component. According to an embodiment of the abutment, the occlusal extending rising has a base forming an asymmetrically contoured outward facing edge having a shape matching a three-dimensional surface shape of the outer gum line of the pre-identified patient. Such shape can be determined, for example, from digitized data of an intro-oral (e.g. silicone or alginate) impression of the dental anatomy of interest or in-vivo imaging data describing or including the three-dimensional surface shape of the gum line. According to an exemplary configuration, a runout at a perimeter of the occlusal extending rising forms a stable non-sharp material edge of approximately 90° or more (e.g., typically) 135°.

According to an embodiment of the abutment, similar to the design of the occlusal extending rising, and vice versa, the apical extending rising has an apical facing surface having an asymmetrical custom-shaped surface contour directly correlated to a surface contour of an apical extending surface of the dental implant, and/or a dental anatomy of the specific pre-identified patient. The apical extending rising is or can be further shaped such that an outline of a cross-section of the apical extending rising directly correlates with an outline of a corresponding cross-section of the dental implant root. The apical extending recess has a three-dimensional shape directly correlated with a three-dimensional shape of substantial portions of the apical facing surface of the dental implant. The three-dimensional surface shape of the apical extending rising can also or correspondingly include a substantial asymmetric negative indent recessed into the apical facing surface of the apical extending rising. According to an exemplary configuration, the apical extending rising includes an apical facing surface having an asymmetrical custom-shaped surface contour directly correlated to an inner surface contour of the apical extending recess extending substantially into a body of the dental implant. Correspondingly, the apical extending recess can define a complementing interface surface, and whereby the apical facing surface of the apical extending rising and the complementing interface surface of the dental implant together create a form-lock fit. According to an embodiment of the abutment, the apical extending rising has a base forming an asymmetrically contoured outward facing edge, and wherein a three-dimensional shape of the asymmetrically contoured outward facing edge matches a three-dimensional surface shape of a bone crest line of a specific tooth socket of the pre-identified patient determined from imaging data describing the three-dimensional surface shape of the bone crest line. According to the exemplary configuration, a runout at a perimeter of the apical extending rising forms a sharp edge of less than approximately 90° (e.g., typically approximately 45°), for example, corresponding to the runout mentioned in the preceding paragraph.

According to various embodiments, dental prosthesis/implant manufacturing methodologies can include copying a significant portion of the original root geometry of a human tooth, to be integrated after extraction of the original tooth either in the existing biological cell structure of the periodontal or perio-type ligament or as one piece into the embedding bone structure of the respective jaw. In an embodiment, primary stability is favorably achieved by a custom made support structure and/or splint that connect the prosthesis with the adjacent tooth or teeth or other dental structures like existing implants, bridges and the like. According to various embodiments of the present invention, an artificial root of the prosthesis or implant can be osseointegrated—embedded into the natural extraction cavity. According to various embodiments of the present invention, the principle of the natural mechanism of holding the teeth in the jaw structure of a dental patient is maintained, preserved and/or regenerated, whereby a customized dental prosthesis is integrated into, healed in, and at least partially adopted by the existing and/or newly formed fibrous connective (ligament) tissue between the prosthesis and the bone socket, comparable to the soft-tissue interface of the periodontal anatomical structure of an individual patient that is naturally holding the tooth. Such fibrous connective tissue between the prosthesis and the bone socket is called herein also perio-type tissue and the respective integration mechanism respectively perio-type integration.

The concept of perio-type integration of an artificial tooth uses the existing human periodontal ligament for integration and is certainly less invasive than the integration of osseointegrated implants. Additionally, it preserves not only the existing bone socket but also the elastic ligament tissue comparable to the aforementioned natural periodontal holding mechanism. The concept of integrating a one-piece prosthesis that includes a root-shape part, an abutment and a crown combines the two or more clinical episodes of integrating the root-shaped part and adapting the crown into one clinical event. Even if the prosthesis would include an assembly of two or more parts, the assembly could be fabricated in the controlled environment of a dental laboratory or an industrial fabrication. As a result, the quality of the interface sealing between such parts can be expected to be of higher quality as produced in the mouth of the patient. This would reduce the infection rate so that the success rate of the prosthesis according to an embodiment of the invention would be higher as achieved with implementations according to conventional processes and procedures. The concept of a primary support structure and/or splint that is custom made in the laboratory in advance serves two purposes: the correct positioning of the prosthesis, and the achievement of reasonable primary stability. The concept of using in-vivo imaging data in order to design and fabricate the prosthesis prior to the extraction of the teeth of interest enables a laboratory lead time prior to the invasive clinical event. The concept of using data to design a root-shaped portion or portions of the prosthesis not actually of the tooth or teeth extracted or to be extracted, but of the anatomical alveolar structure, allows the prosthesis to adapt to the post-extraction or even post-surgical—in case of, for example, surgical extensions to the extraction socket— shape of the alveolar situation.

Any combination of the aforementioned concepts of the invention can be used in embodiments of efficient and/or less-invasive clinical methods according to the exemplary embodiment of the invention. One of such clinical methods, for example, includes the immediate placement of a prosthesis—allowing immediate loading. In another embodiment, these concepts can be combined with methods of ultrasonic or other vibrations applied to the prosthesis or adjacent tooth/teeth after placement in order to stimulate bone and tissue healing. In another embodiment, the extraction of the tooth might be performed using ultrasonic or other vibrations applied to the tooth of interest to facilitate the extraction.

All such methods can be also favorably combined with laboratory methods according to one or more embodiments of the invention. One of such laboratory methods might be the coating of the root portion of the prosthesis with engineered tissue that is grown in the laboratory from autologous tissue, cell, bone or root material samples of the patient of interest. Alternatively to the aforementioned use of autologous material, human allogenic cell, bone, root or tissue material can be used. Alternatively to the use of human bio material, cell, tooth, bone or tissue material of animals, for example, bovine or even synthetic materials can be used for the process step of tissue engineering. Alternatively or in addition to the coating of the root portion of the prosthesis with engineered tissue, laboratory methods can be employed to harvest, select and/or proliferate cells, such cells to origin the tissue of interest. In an embodiment of the invention, the cells to origin the tissue of interest can be applied onto the surface of the prosthesis prior to the insertion, or placed adjacent to the prosthesis in the jaw socket during the clinical procedure. In such situation, the applied or adjacently placed cells would origin, i.e. regenerate the hard and/or soft tissue of interest in-vivo. All laboratory methods can be carried out partially or in its entirety in-vitro but in or next to the actual surgical suite—called in dentistry "chair-side". Tissue engineering includes the use of a combination of cells, engineering materials, and suitable biochemical factors to improve or replace biological functions. In the context of certain embodiments of the invention disclosed herein, this would include the growth of soft tissue or bone structures in a controlled laboratory environment. The term regenerative medicine is often used synonymously with tissue engineering, although those involved in regenerative medicine place more emphasis on the use of stem cells to produce tissues. This is an additional approach that can be favorably combined with other specific embodiments of the invention disclosed herein. The terminology "tissue engineering" and "regenerative medicine" as used herein, however, shall include the use of stem cells, ancestral cell, multi-potent cells as well as finally differentiated cells. An embodiment of the invention using finally differentiated cells can be of advantage since it would reduce significantly the risk that multi-potent cells would differentiate unwantedly and create in the worst case tumors.

In this context, various embodiments of the invention described herein relate to fabricating customized artificial copies of segments of the dentition, single teeth, roots and crowns or parts of those, and primary support structures and splints. The artificial reproduction of the original root will be inserted into the alveolus, the natural cavity of the root of the tooth to be replaced. It will either be adopted by the periodontal ligament of the patient or osseointegrated if the periodontal ligament is no longer functional, the foregoing also depending on various aspects of surface conditioning of the prosthesis and on the clinical protocol employed. The shape of the root can be a substantial copy of the root to be replaced or may be intentionally smaller, for example, to compensate for measurement or manufacturing tolerances or inaccuracies. It can be even made smaller to allow for additional substances to be injected or otherwise placed adjacent to the prosthesis to facilitate bone augmentation or soft tissue regeneration. The shape of such roots may alternatively be a direct copy of the root to be replaced, or it may be directly adapted to the alveolar situation, or any combination thereof. In certain cases it is advantageous to modify the shape to be integrated. For instance, it may be appropriate to conjoin the two or three roots of a molar partially or in its entirety to gain additional stability or enable the manufacturing of such. Also, strongly bent root tips may be reduced or left away in order to ease the insertion of the prosthesis. In cases of root resorption, it may be appropriate to re-establish a shape close to the estimated shape of the original shape of the root before the resorption clinically occurred. Even imaging data of an earlier clinical situation or imaging data of mirrored or un-mirrored data of the same or a similar shaped root of the same or the other (right-to-left, left-to-right) side of the jaw or of an opponent jaw of the patient may be favorably used in this context. It may be additionally possible to consider and use generic (averaged) root shapes in the process designing the target shape of the prosthesis. The extraction socket may be surgically enlarged to accommodate for a bigger or different root shape compared to the extracted root shape.

Additional embodiments of a method of manufacturing a dental prosthesis to replace a non-functional natural tooth positioned in or received from a jawbone of a specific pre-identified patient are further described. An example of such a method can include the steps of receiving data describing a three-dimensional X-ray image of at least portions of the patient's dentition defining x-ray image data, and receiving data describing one of the following: a physical impression of a dental anatomy and a surface scan of the dental anatomy, defining impression image data made prior to removal of the non-functional natural tooth from the jawbone of the specific patient. The steps can also include forming at least one three-dimensional virtual model of at least portions of the non-functional natural tooth to include combining the x-ray image data and impression image data, and forming the at least one three-dimensional virtual model of the non-functional natural tooth including a modeled virtual root portion and a modeled virtual crown portion responsive to the x-ray image data and the impression image data.

The steps can also include designing a dental prosthesis based upon the at least one virtual model of at least portions of the non-functional natural tooth. The step of designing the dental implant includes the steps of forming a virtual dental implant body modeling a dental implant body (e.g., root portion) having a virtual abutment apical-facing surface interface modeling an abutment interface extending into the dental implant body to receive a transgingival interlock abutment component. The step of forming a virtual dental implant body can include forming the virtual abutment apical-facing surface interface to have a three-dimensionally contoured implant body surface shape at least partially correlated to a surface shape of an apical surface of the modeled virtual root portion.

According to a three-part dental prosthesis configuration, the step of forming a virtual dental implant body includes separating a portion of the at least one three-dimensional virtual model along a virtual bone-facing gum line representation (e.g., effectively shaping the outward-facing circumferential edge of an abutment interface), copying at least portions of the modeled virtual root body portion to form a base shape of the abutment interface, reducing dimensions of the at least portions of a second copy of the modeled virtual root body portion and smoothing the result to define a virtual abutment apical-facing surface interface model, and combining the virtual abutment apical-facing surface interface model with the virtual root body portion model to form the virtual dental implant body having a recess for receiving an apical extending rising of a transgingival interlock abutment.

According to this configuration, the steps can also include forming a virtual occlusally-facing dental prosthesis component modeling an occlusally-facing dental prosthesis component, such as, for example, a virtual crown component and/or a virtual prosthesis/abutment interface member of an integrated support device for providing primary stability to the dental prosthesis. The virtual dental prosthesis component can be formed by separating a portion of the at least one three-dimensional virtual model along a virtual outer gum line representation to form a virtual crown portion (e.g., effectively shaping the outward-facing circumferential edge of an abutment interface), copying at least portions of the modeled virtual crown portion, reducing dimensions of the at least portions of a second copy of the modeled virtual crown portion and smoothing the result to form a virtual abutment occlusal-facing surface interface model, and combining the virtual crown portion model with the abutment occlusal-facing surface interface model to form at least portions of the virtual dental prosthesis component having an occlusal facing recess for receiving an occlusal extending rising of a transgingival interlock abutment.

According to this configuration, the transgingival interlock abutment can be formed using a similar set of procedures. For example, the step of forming the occlusal extending rising of the transgingival interlock abutment can be formed by copying at least portions of the abutment occlusal-facing surface interface model, and reducing the dimensions to form a virtual complementing outer surface structure of the occlusal extending rising. Similarly, the step of forming the apical extending rising of the trans-gingival interlock abutment can be formed by copying at least portions of the abutment apical-facing surface interface model, and reducing dimensions to form a virtual complementing outer surface structure of the apical extending rising. The virtual outer surface modeled outer surface structures can be combined with a model of the portion of the at least one virtual model of at least portions of the non-functional tooth between the virtual outer gum line representation and the bone-facing gum line representation to form a virtual model of the trans-gingival interlock abutment.

Further, a computer can produce a set of digital data virtually describing the three-dimensionally contoured outer and inner body surface shapes of the dental implant, the outer and inner body surface shapes of the dental prosthesis component, the outer surface shapes of the integrated support device, and the outer surface shapes of the trans-gingival interlock abutment, which can be utilized by a manufacturing apparatus. As such, the design and manufacturing/fabricating steps can also include employing a machine process performed by a computer numerical control (CNC) based machining apparatus to form substantial portions of the dental prosthesis responsive to the set of digital data, and/or employing a rapid prototyping process performed by a computer numerical control (CNC) based rapid prototyping apparatus to form substantial portions of the dental prosthesis responsive to the set of digital data.

Various embodiments of the present invention avoid or postpone the need of or for conventional heavily invasive implants for a significant time by using at first the natural periodontal structure as long as possible and afterwards by customized osseointegrated artificial roots or teeth. No such approach in dentistry based on design and manufacture of customized teeth including the root, or only roots suitable to be used in conjunction with off-the-shelf or customized components (typically for the visible part like veneers or complete crowns) used in the field of implantology for an individual patient, and design and manufacture of such customized tooth, has been proposed to date. The implants widely used in dental treatment today are off-the-shelf products. Because teeth have to fit properly for comfort and healing after surgery in the periodontal ligament of a patient, some commonly used implants do not constitute an optimal replacement.

In an embodiment of the present invention, a dental prosthesis is assembled as a one-part ceramic implant body with a translucent glass-ceramic cap. To achieve a qualitatively high one-piece dental implant or other components of a dental prosthesis, the white body of the implant or the component, root portion body is finished in a hot isostatic pressing process. Hot isostatic pressing (HIP) describes compression of materials to almost its theoretical density, by applying high temperatures and high pressure to the work piece of interest, i.e., the prosthesis or parts thereof. Therefore, firstly, the ceramic implant is covered with a customized metallic coating, or sintered to a density that the gas used for the later process step of hot isostatic pressing cannot transpire or migrate into the object to be pressed. In a further step, the coated or tightly sintered implant is placed in an oven with a temperature closely under the melting point of the ceramic material of the dental implant. Furthermore, an increased pressure is applied to the coated implant, thereby eliminating certain defects and flaws. After this process step (often called hot isostatic pressing), the coating is removed from the body by e.g., an etching process. The removal of the coating from the ceramic body can also be achieved by mechanic means. In an alternative embodiment, the ceramic implant is sintered in a first process step form its porous structure to be dense to a degree that the gas or other media employed in the following hot isostatic pressing process cannot invade into the material itself, so that the compressing, and therefore the elimination of internal defects, can take place. In another embodiment, the abutment and the root portion are separately subjected to the hot isostatic pressing process and then bonded together to form a one part ceramic implant body.

In a further embodiment, the implant body is made of two or more different materials being assembled and connected by a soldering process and/or by diffusion bonding. Diffusion bonding may include technologies connecting different materials on an atomic level without a facilitating third material. Diffusion bonding may be facilitated by hot isostatic pressing to provide the required connection of the adjacent materials to the degree where diffusion bonding takes place. In another embodiment, the abutment is subjected to the hot isostatic pressing process and bonded to a root portion of a different material such as, for example, titanium or other compatible metal. In another embodiment, the corresponding surfaces of the components of the dental prosthesis are silicatised as a coating using a diffusion bonding process and then the silicatised components are fused together with a glass solder or welding material. It can be preferable to use for the silicatising process of the ceramic component, a higher temperature, e.g., typically 1000° C., for the silicatising process of the titanium component, and e.g., typically 800° C. for the actual fusing process.

In another embodiment of the present invention, the dental prosthesis provides a porous outer surface of the root body portion. Such a porous surface acts as a biocompatible and cell pleasing environment. Thereby, the process of osseointegration of the dental prosthesis into the jaw bone or the process of integration into the periodontal ligament is promoted. The porous outer surface can be achieved by, e.g., applying ultra-short laser pulses onto the surface eroding the material without a remnant of scoria or thermally altered adjacent surface material. Ultra short means time pulses having a length in time measured in the range of 1 to 1000 pico-seconds or 1 to 999 femto-seconds. Alternatively, the porous coating can be achieved by milling the outer surface of the root body portion. Moreover, the porous outer surface can be achieved by covering the outer surface of the root body portion with a ceramic porous coating which is applied or assembled in a customized and well controllable process. Titanium as well as ceramic components of a dental prosthesis or parts thereof can be first sandblasted and second acid etched to create an extremely rough surface to enhance soft and hard tissue integration. The acid etching process can be employed at higher temperatures (e.g., typically 80° C.). One or more geometrical indents in the root portion of the prosthesis (as probably best shown at the surface of the root portion 401 in FIG. 41) with an area size of 0.1 to 10 mm$^2$ (typically 3 mm$^2$) and a depth between 0.1 and up to 2 mm (typically 0.8 mm), called retentions, provide a form fit with the ingrowing bone and can be combined with the rough and porous surfaces to further enhance the long term stability of the integrated prosthesis.

In another embodiment of the present invention, the prosthesis comprises a customized form with an upwardly directed convex surface in the area between the roots of the prosthesis. Such a form prevents air inclusions from being enclosed in the area between the roots of the prosthesis.

In a further embodiment of the present invention, the one-part implant and the cap are separated by a customized joint. This customized joint is embodied as a three-dimensional surface comprising a form that is individually fitted to the design of the prosthesis and the course of the patient's gingiva.

In another embodiment of the present invention, the overall fabrication is simplified. In this method, firstly, an impression is made of the patient's tooth. Moreover, a scan is obtained from a computed tomography device. Both types of data are combined and CNC-instructions (CNC: Computerized Numerical Control) are generated for the fabrication of the milling of the prosthesis and the dedicated splint. As another enhancement of the present invention, the overall fabrication process can partly or totally be executed at the chair side of the dentist executing the treatment of the patient.

In yet another embodiment of the present invention, the surface data obtained from the impression of the tooth and the surface data obtained from the computed tomography device are combined utilizing statistical methods.

Directly after placement, the prosthesis may be tied, glued or otherwise fixated for several weeks to adjacent original or artificial teeth. Accordingly, various embodiments of the present invention provide an integrated support device, or alternatively, a custom splint in order to provide primary stability ball the implant portion of the prosthesis is integrated into the alveole.

The various embodiments of this invention described herein are not only substitutive but additive to the available options in the field of restorative and prosthetic dentistry with the result that in most cases the need to use removable dentures will be significantly postponed.

BRIEF DESCRIPTION OF THE DRAWINGS

So that the manner in which the features and advantages of the invention, as well as others which will become apparent, may be understood in more detail, a more particular description of the invention briefly summarized above may be had by reference to the embodiments thereof which are illustrated in the appended drawings, which form a part of this specification. It is to be noted, however, that the drawings illustrate only various embodiments of the invention and are therefore not to be considered limiting of the invention's scope as it may include other effective embodiments as well.

FIGS. 17A-17C illustrate a prior-art dental implant.

FIG. 18 illustrates a natural tooth.

FIG. 24 illustrates copying of portions of the divided virtual model.

FIG. 25 illustrates the combining of virtual models to form a virtual crown portion.

FIG. 26 illustrates the combining of virtual models to form a virtual dental implant body.

FIG. 27 illustrates the attachment of a crown portion of a dental implant to a dental implant body to form the dental implant.

FIG. 35 illustrates the combining of virtual models to form a virtual dental implant body portion.

FIG. 36 illustrates the combining of virtual models to form a virtual transgingival cap portion.

FIG. 37 illustrates the combining of virtual models to form a virtual crown portion.

FIG. 38 illustrates the attachment of a transgingival cap portion of a dental implant to a dental implant body and attachment of a crown portion to the transgingival cap portion to form the dental implant.

FIG. 39 illustrates a completed three-piece dental implant.

FIG. 45 is an exploded view of the exemplary prosthesis shown in FIG. 41 according to an embodiment of the present invention.

FIG. 46 is an exploded view of portions of the exemplary prosthesis shown in FIG. 41 supported by an integrated support device according to an embodiment of the present invention.

FIG. 59 is a perspective view of an integrated support device according to an embodiment of the present invention.

FIG. 60 is a perspective view of an integrated support device according to an embodiment of the present invention.

FIG. 76 is a sectional view illustrating the combining of the virtual prosthesis interface member with a skin model of a set of bonding wings according to an embodiment of the present invention.

FIG. 77 is a sectional view illustrating the combining of the resultant model shown in FIG. 76 with a copy of the skin model to form the bonding wings and to complete the model construction of an integrated support device according to an embodiment of the present invention.

DETAILED DESCRIPTION

The present invention will now be described more fully hereinafter with reference to the accompanying drawings, which illustrate embodiments of the invention. The invention may, however, be embodied in many different forms and should not be construed as limited to the illustrated embodiments set forth herein. Rather, these embodiments are provided so that this disclosure will be thorough and complete, and will fully convey the scope of the invention to those skilled in the art. Like numbers refer to like elements throughout. Prime notation, if used, indicates similar elements in alternative embodiments.

Current methods for replacing damaged teeth have several disadvantages. For example, conventional bridge implants require healthy teeth to be ground, and traditional osseointegrated implants are drastically invasive. Additionally, these prostheses have a limited average lifetime. Removable dentures are the final prosthetic option. An object of the invention is to design and manufacture customized dental prosthesis for replacing human teeth and support structures and/or splints which provide primary stability until such time as secondary (long-term) stability is achieved.

Dental Prosthesis

Figure 1:
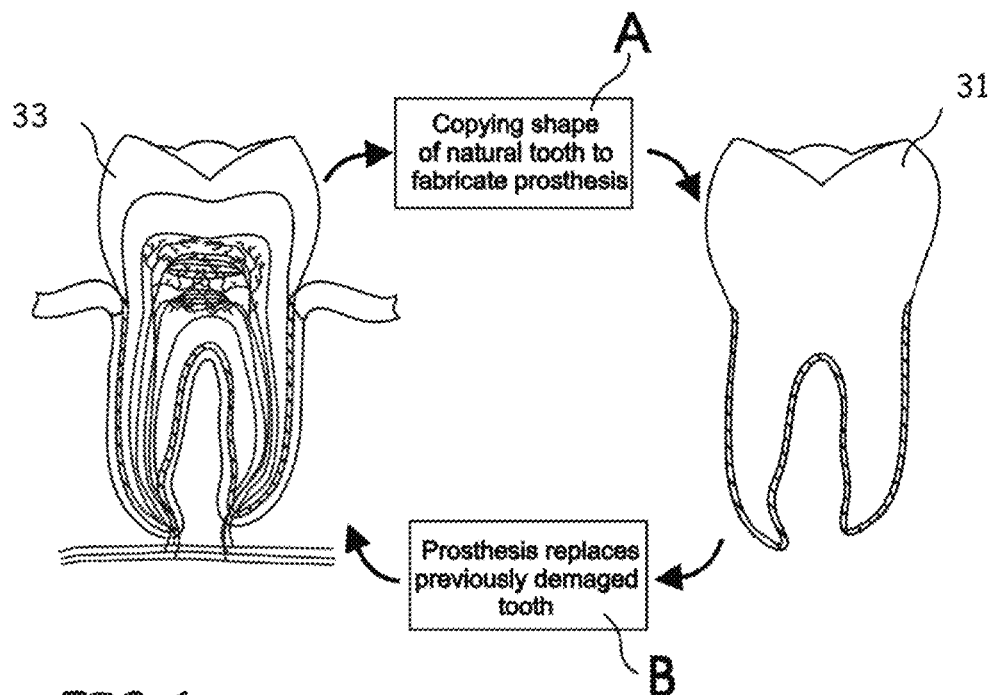
FIG. 1 illustrates a procedure of replacing a human tooth with a prosthesis in accordance with an aspect of the invention.

FIG. 1 illustrates a method of replacing a human tooth with a customized dental prosthesis according to an embodiment of the invention. First, in step (A) a copy 31 of the natural tooth 33 to be replaced is fabricated. Then, in step (B) the natural tooth 33 is replaced with the prosthesis 31.

Figure 2:
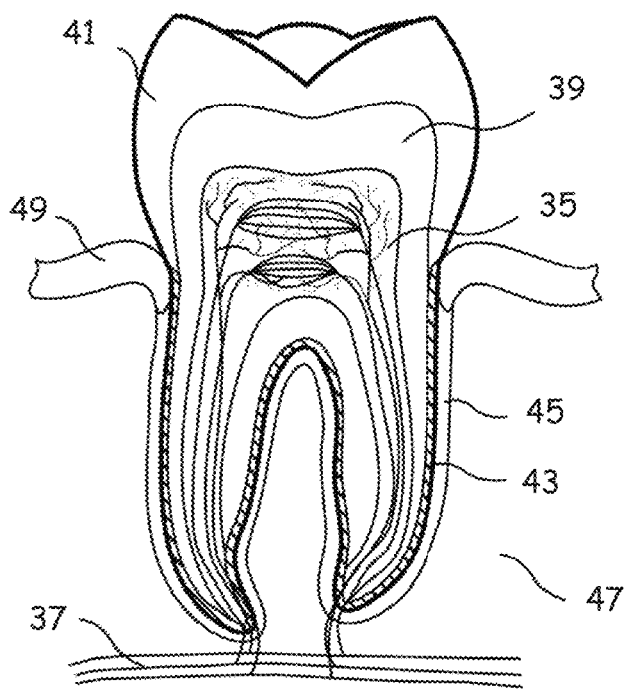
FIG. 2 is a detailed cross-sectional view of a natural tooth.

FIG. 2 shows a natural tooth embedded in its socket. The pulp 35 holds nerves and blood vessels 37. It is surrounded by dentine 39, which is covered on the top part of the tooth with enamel 41. The root portions have a thin layer of cement 43 providing connection to the ligament 45, which serves to anchor the tooth to the bone 47. The outside of the bone is covered with gum 49 that forms a seal with natural tooth to protect the ligament 45 and the bone 47.

According to an embodiment of the invention, portions of a dental prosthesis are individually shaped and integrated into the natural extraction socket of an individual specifically identified patient. The shape of the portions of the prosthesis representing the root can substantially copy the natural root of the tooth that was located in the socket. However, the shape may be modified in order to better adapt to the natural socket or to ease insertion of the prosthesis. Also, the socket may be surgically adapted for the same reasons. For example, damaged and infected soft tissue, tooth or bone substances would not allow for immediate or even delayed implantation.

An embodiment of the present invention includes the following steps: (i) Recording and digitizing (scanning) the three-dimensional anatomical shape of a human tooth or dentition; (ii) Obtaining a virtual model of the tooth as data record; and (iii) Manufacturing of the prosthesis, based on the three-dimensional data that have been obtained by the scan and if applicable, optimized.

Figure 3:
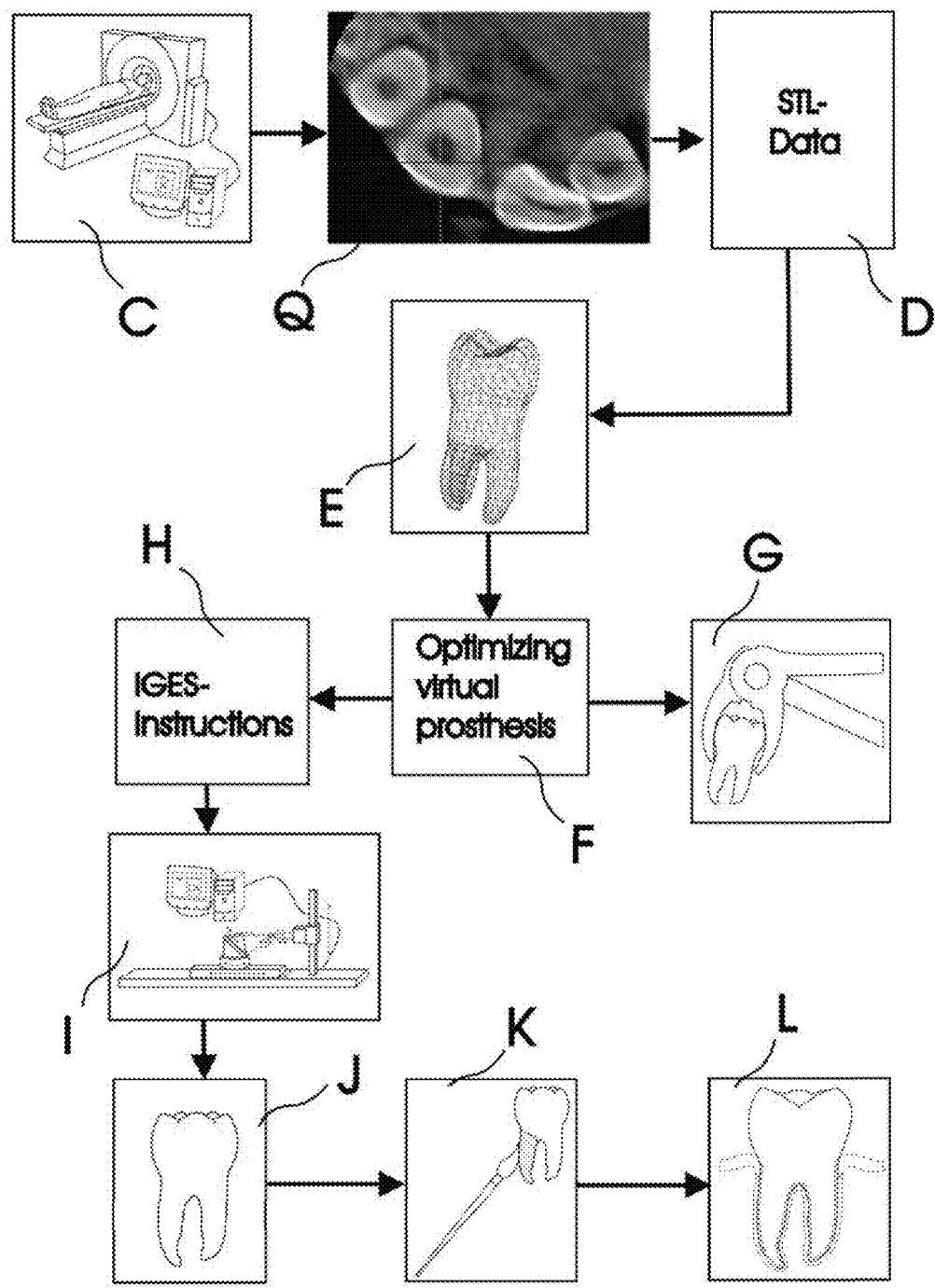
FIG. 3 illustrates the process steps of intra-orally acquiring three-dimensional data of a human tooth, fabricating an artificial copy, extracting the natural tooth and replacing it with the artificial copy according to an embodiment of the invention.

FIG. 3 shows an example of process steps for intra-orally acquiring three-dimensional data of a human tooth, fabricating an artificial copy, extracting the natural tooth and replacing it with the artificial copy according to an embodiment of the invention. A CT scan (steps C, Q) is made of the dentition of the patient. The resulting data are volume based, where every numerical volume element (each called a "voxel") represents the X-ray density of the corresponding natural volume portion of the dentition of the patient. The 3D voxel data are usually provided in a Digital Imaging and Communications in Medicine (DICOM) format. The volume data are converted into surface data, e.g. Surface Tesselation Language (STL) 3D data (step D), imported into Computer Aided Design (CAD) software and displayed to the operator (step E). The shape is modified and optimized as needed (step F). The resulting CAD 3D data is converted, for example, into the standardized Initial Graphics Exchange Specification (IGES) format and exported (step H) to a Computer Aided Manufacturing (CAM) system for fabricating the prosthesis (step I). The process may include coating the finished prosthesis (step J) with a substance promoting bone ingrowth (step K). Only after the prosthesis is ready for insertion, is the natural tooth extracted (step G), and the implant is placed into the extraction socket (step L). It should be noted that although FIG. 3 contemplates possibly interaction with an operator, one skilled in the art would readily appreciate that this functionality may be fully automated.

The data may either be recorded intra-orally from the patient, such as with a 3D camera, a micro laser optical device, a computerized tomography apparatus, or an ultrasound apparatus, or be recorded extra-orally by scanning an extracted tooth. If required, the model can be modified in order to ease insertion, divided and separated if the prosthesis is to be fabricated in components and assembled prior to insertion, or modified to receive aids for the final correct positioning of the fabricated prosthesis. The prosthesis can be fabricated as one piece or in components to be assembled prior to insertion. The prosthesis or its components can be directly produced by milling, grinding or rapid prototyping, for example, at a dentist's office or in a laboratory. It can also be produced using conventional laboratory procedures like casting. Preferably, the implant portion representing the root is manufactured using CAM methods, e.g., based on an acquired virtual model, while other portions of the prosthesis, for example, representing the crown or bridge, can be manufactured using standard procedures known in the art. Such methodologies, along with various others, are described in more detail, for example, in U.S. patent application Ser. No. 13/247,607, incorporated by reference in its entirety.

According to an embodiment of the present invention, a segmented prosthesis can be used. A segmented, also referred to a segment, prosthesis is one in which a first segment is implanted into the extraction socket and second segment, for example, a portion representing the crown of a tooth, is attached to the segmented portion. Accordingly, segmented prosthesis include at least two separate portions which may be manufactured and implanted at separate times. The segment which is implanted into the extraction socket can include a portion that is a representation of the root of the natural tooth and can be manufactured based on 3D imaging data. The segment representing the crown can also be at least partially manufactured according to 3-D imaging data and/or other processes according to standard procedures known in the art, and laminated or coated with an ecstatically pleasing material known to those of ordinary skill in the art.

In an embodiment of the present invention where the prosthesis will be positioned for osseointegration, INFUSE® can be used to improve healing time and enhance the integration. Bone Graft (Medtronic Sofamor Danek) can be applied to stimulate bone formation. INFUSED Bone Grafts consists of two parts—a solution containing rhBMP-2 (recombinant human bone morphogenetic protein 2) and the ACS (absorbable collagen sponge). The protein is a genetically engineered version of a natural protein normally found in small quantities in the body. The stimulation of bone formation is key to develop osseointegration, and to fill voids in between the extraction socket and the actual prosthesis in an accelerated manner. Other growth aiding proteins like bone morphogenetic protein (BMP), dentin matrix protein (DMP), platelet-derived growth factor (PDGF) and/or other bone growth stimulating proteins may be applied or otherwise used additionally or instead in order to facilitate integration, healing, and rebuild of the bone structure of the patient.

In another embodiment of the invention, cell attracting cytokines are attached or applied to the implant surface to be integrated. For example, that cytokine material InductOss (Wyeth) attracts bone building cells (i.e., osteoblasts) to enhance osseointegration. In contrast specific cytokine material can be applied to attract cementoblasts and/or fibroblasts to regenerate the perio-type membrane and avoid osseointegration.

In a further embodiment of the invention, cells (including but not limited to autologous and/or allogeneic cells) are attached or applied adjacent to or contained in a gel-type scaffold. Agarose gel scaffolds, platelet gel and/or fibrin (Baxter) based scaffolds are used. In order to create a geld type fibrin scaffold, the two components of fibrin sealant are mixed in a ratio 80:20 instead of 50:50.

Figure 4:
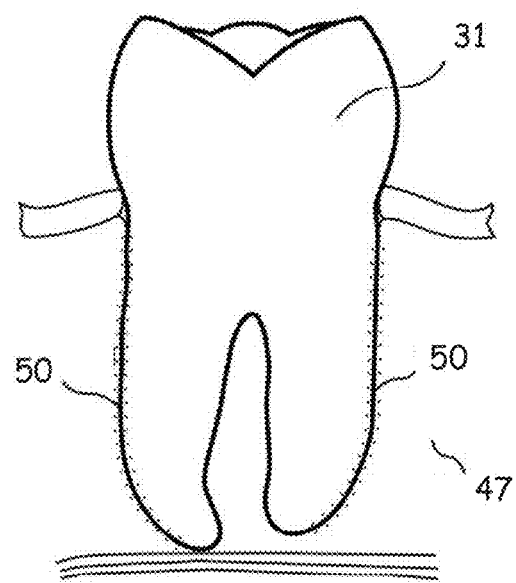
FIG. 4 illustrates an artificial tooth (an dental prosthesis) inserted into the extraction socket and, after a healing period, fully integrated into the bone.

A resin strip can be utilized to secure the prosthesis in place. An advantage of embodiments that employ osseointegration is that the complete replacement of the natural tooth can be performed in one appointment. After the prosthesis has healed in, only the resin strip initially securing the prosthesis to the adjacent teeth must be removed. A significant amount of laborious steps can thus be avoided. FIG. 4 shows an osseointegrated unsegmented tooth 31. Osseointegration is achieved in marked areas 50.

In yet another embodiment, the prosthesis will not be osseointegrated, but adopted by the ligament of the extraction socket. In this case the prosthesis is coated with a material promoting perio-type adoption. For example, a thin layer of about 0.05 mm to 0.2 mm of resin-modified glass-ionomer cement, for example, can be applied to the surface of the part of the workpiece being inserted into the extraction socket. Alternatively and additionally, substances promoting periodontal integration are applied, such substances include but are not limited to other types of natural tooth segments, natural tooth materials such as dentin, enamel and cementum (or a combination thereof), pharmaceuticals, ancestral cells, proteins, and cell parts of a human tooth. The substances can be in liquid, gel or powder form or provided as shavings or as any combination thereof, and the cells can be isolated or attached to separate scaffold material or to the implant surface, or a combination thereof. The meaning of "ancestral cells" shall include but shall not be limited to multi-potent and stem cells, as such cells have the ability to further differentiate. The meaning of "cell parts of a human tooth" shall include but shall not be limited to PDL-fibroblasts, non-PDL-fibroblasts, cementoblasts, osteoblasts and ancestral cells, having the ability to differentiate into PDL-fibroblasts, non-PDL-fibroblasts, cementoblasts and osteoblasts. "PDL" shall mean in this context "periodontal ligament" or "perio-type ligament" as applicable.

Especially in the context of perio-type integration, it might be advisable to utilize a Guided Tissue Regeneration (GTR) membrane, for example an absorbable collagen membrane, to separate the faster gum growth from the healing process of the periodontal ligament.

In another embodiment, an undersized customized root representation of a ceramic prosthesis is coated with a thin layer of mineral trioxide aggregate (ProRoot MTA, Dentsply) while potential socket irregularities are prepared with calcium sulphate (Capset, Lifecore Biomedical) in order to promote the selective formation of new perio-type tissue (i.e., cementum, perio-type ligament, Sharpey's fibers and alveolar bone) and to build a barrier against an overgrowth by gingival tissue. The thickness of the coating layer may match the undersizing of the root shape and would preferably be chosen to be about 0.2 to 0.3 mm. Alternatively, the outer shape of the root portion of the prosthesis and the coating thickness could still maintain an undersizing of substantial portion of the surface of the root portion compared to the shape of the natural tooth. It would furthermore be advantageous to insert the prosthesis into the socket as soon as possible, but no more than 24 hours (see respective reference re: Spouge, Oral Pathology, Mosby, Saint Louis, 1973 above), after extraction.

Figure 5:
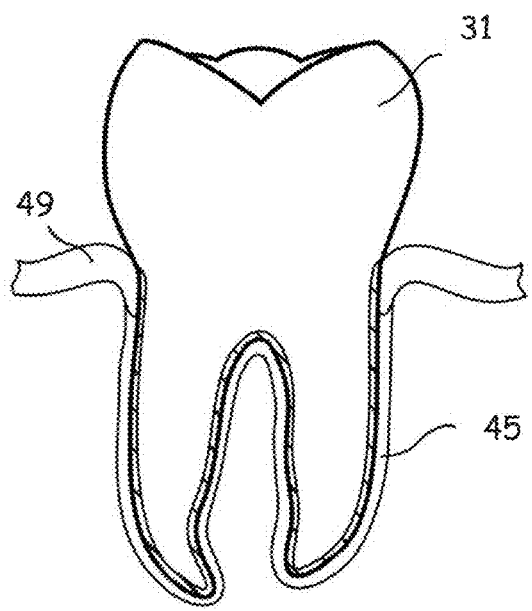
FIG. 5 illustrates an artificial tooth being embedded in the socket of the natural tooth.

Perio-type integration (FIG. 5) has the advantage that the anchoring of the prosthesis 31 is not stiff as with osseointegrated implants, but shows the elasticity of the natural tooth. The soft tissue ligaments 45 are providing support to the teeth in a viscoelastic manner. Furthermore, forces applied to the tooth and thus, to the ligaments, create tension which is actually the stimulus for bone growth. Another function of the periodontal or perio-type ligaments is to serve as a method for tactile sensation. To support perio-type integration, the implantation of the prostheses should be performed shortly after extraction of the natural tooth, preferably not more than 24 hours after extraction. A key to success is the preservation of cellular vitality in the periodontal or perio-type ligament and performing the extraction in a surgical environment under conditions of asepsis. Further below, other embodiments of the invention are disclosed providing instant replacement of the natural tooth.

In another embodiment, not fully individualized per tooth and per patient, but suitable pre-determined generic root shapes can be selected and employed for fabricating the portion of the implant to be osseointegrated or integrated into the periodontal or perio-type ligament. A variety of generic shapes may be stored on a computer-readable media and accessed by the CAD/CAM system.

In yet another embodiment, the crown of the extracted tooth or the tooth to be extracted is not only subject to 3D imaging, but additional color data are obtained. Depending on the scanning method, color data can already be contained in the scan data, or a separate imaging is performed to record the color of the crown. It is possible to obtain a uniform overall color representing the average color of the crown, or alternatively, different shadings for different portions of the crown can be recorded. Based on the color data, the color of the crown can be adapted to the color of the original tooth. The lab technician manufacturing an artificial crown can, for instance, be provided with the color data and select the most appropriate color for the prosthesis. If a complete prosthesis is manufactured using CAM methods, a material best fitting the original color can be used, or a coating can be selected that matches the original color or even the individual pattern of colors.

Figure 6:
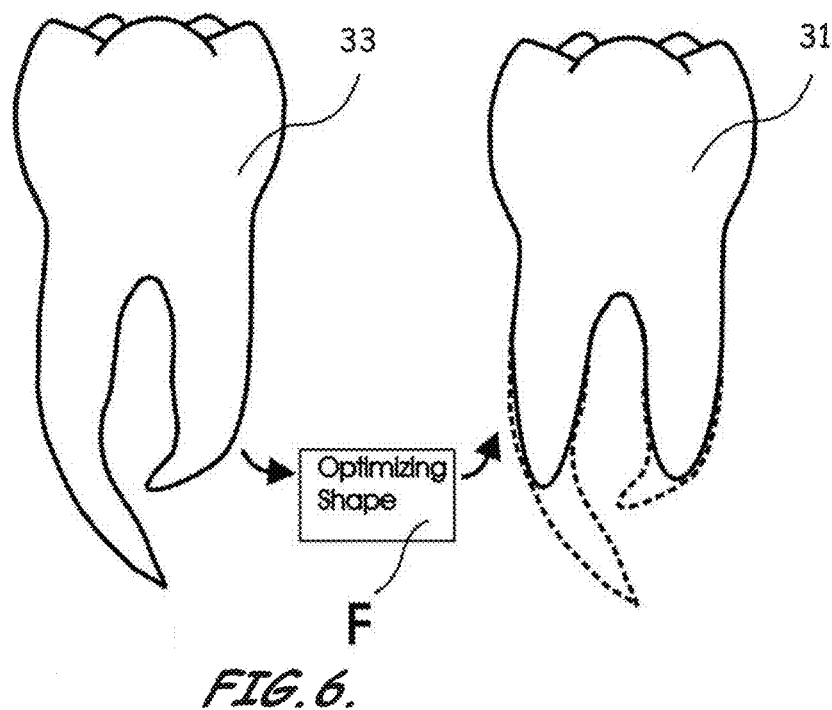
FIG. 6 illustrates a natural tooth having strongly crooked roots and the artificial substitute, wherein the shape of the substitute has been altered in order to allow for simplified insertion into the natural socket.
Figure 7:
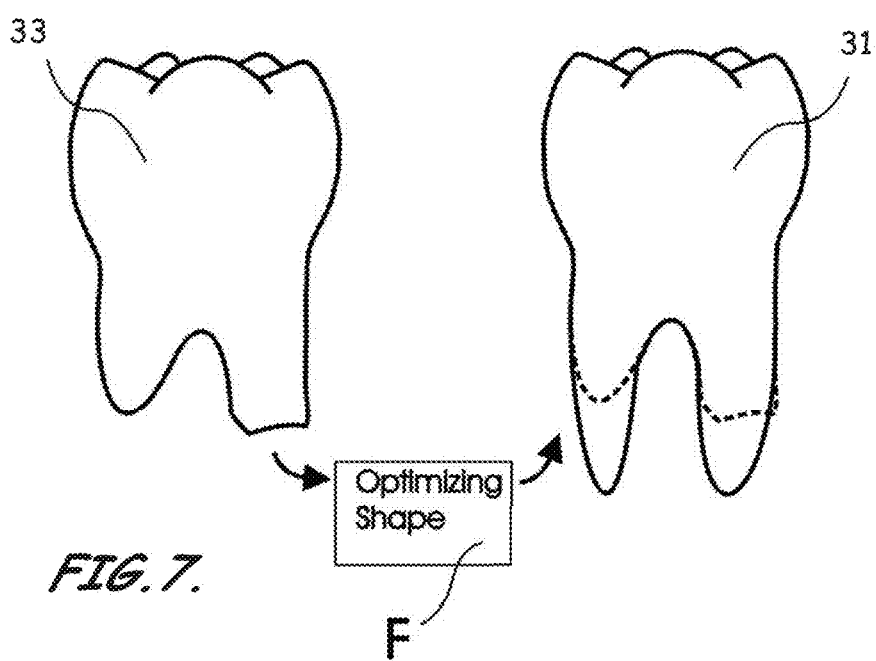
FIG. 7 illustrates a natural tooth suffering from partial root loss due to root resorption or a surgical procedure and an artificial substitute, the shape of the artificial tooth being optimized for better adaption to the natural socket.
Figure 8:
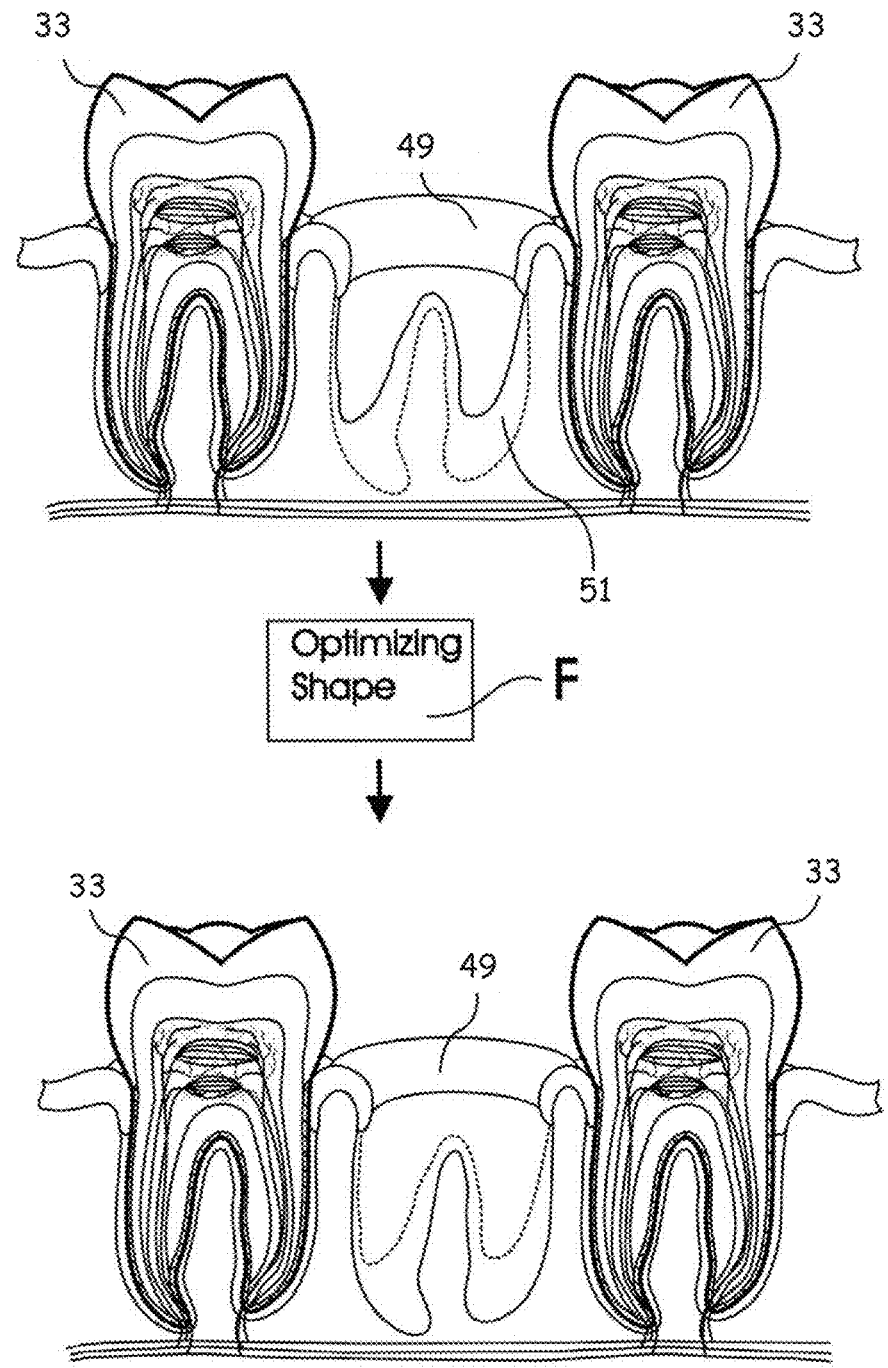
FIG. 8 illustrates a tooth socket after extraction. Due to root resorption, the size of the socket has been reduced over time. In order to enhance anchoring, the artificial replacement will have a root portion of greater size. Therefore, the socket is surgically enlarged.

In some cases the shape of the original roots will present difficulties on the insertion of the artificial replacement. For example, braided or divergent roots of a molar tooth or hocks and undercuts of roots need to be modified to allow for insertion. Also, the furcation can be modified in its vertical height or otherwise as prescribed by the doctor of record. In such cases, a proper modification and optimization of the shape of the artificial root according to FIG. 6 is applicable. In other cases, the root of the natural tooth may be suffering from partial root loss due to root resorption or a surgical procedure. In these cases or if otherwise prescribed by the doctor of record, the root of the replacement may be adapted to the extraction socket or even beyond as demonstrated in FIG. 7. For example, the customized portion includes a substantial copy of at least 60% of the root shape of the natural tooth while the other portion of the artificial root is modified as described herein. In other cases, the size of the socket may have been reduced over time due to root resorption as displayed in FIG. 8. The size reduction has occurred in areas 51. In such cases, it is advantageous to enhance anchoring by surgically enlarging the socket and to adapt the root of the artificial tooth to the enlarged socket. SolidWorks is a suitable CAD software to alter the shape of the implant with respect to the original imaging data.

Figure 9:
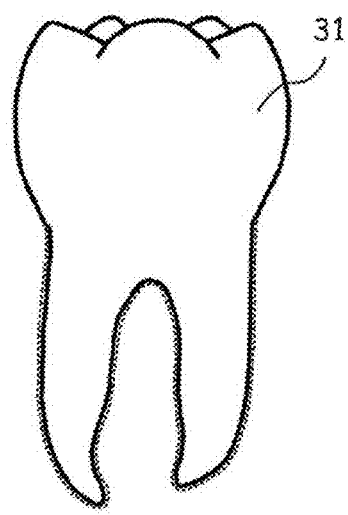
FIG. 9 illustrates an artificial tooth, the portion representing the root being slightly reduced in size compared to the natural tooth.

There are more reasons to modify the shape of the implant with respect to the original root. To ease insertion into the extraction socket, the shape of the implant may be slightly undersized as shown in FIG. 9. MAGICS provides a functionality allowing for a simple reduction of the overall size of a body. This software has a couple of helpful features that have originally been developed to optimize plastic parts for injection molding, but turned out to be useful also for the processes of various embodiments of this invention.

In an exemplary embodiment, the root portion of the prosthesis adjacent to the bone socket of the extraction site substantially mimics either the root shape of the non-functional tooth to be replaced or the three-dimensional shape of the bone socket or any combination thereof, but will be dimensioned not to exceed the shape of the bone socket in order to avoid a conflict when positioning the prosthesis clinically in the pre-defined position and inclination. In a further embodiment, measurement and/or manufacturing tolerances are considered undersizing the root portion adjacent the bone socket in its design. Manufacturing tolerances are to be estimated between 10 and 50 micrometers. Measurement tolerances are to be estimated between 20 and 400 micrometers.

To achieve a long living prosthesis, the size and the shape of the root and the socket needs to be appropriate to enable solid anchorage in the bone. If, for example, a root is too small to absorb the normal chewing forces it may be necessary to expand the size of the socket before designing and manufacturing the customized root. Other patients may not have enough bone material or the outward facing lamella of bone (called "bundle bone") does not have a thickness to maintain the bone structure after the extraction of the natural tooth, so that the thickness of the bone gingivally and labially is not sufficient for the anchorage of an implant, or to support the aesthetically expected clinical outcome. In such a case, the root may be shaped even smaller in corresponding areas of a critical bone lamella to allow for placing bone augmentation material known to those skilled in the art adjacent the implant into the extraction socket order to support a minimum thickness of bone (typically, a bone lamella that has a thickness of at least 1 mm is considered stable). This approach significantly increases the stability of the anchorage because no hollow or less stabile areas remain in the bone. If crown and root are manufactured as one part, the crown may be coated with an enamel-colored layer or multiple layers for aesthetic reasons. Such layer(s) can be, for example, translucent to a certain extent. During the healing process, appropriate measures need to be put in place to avoid early exposure of the implant to forces (bite bumpers, partials positioners, etc.).

Figure 10:
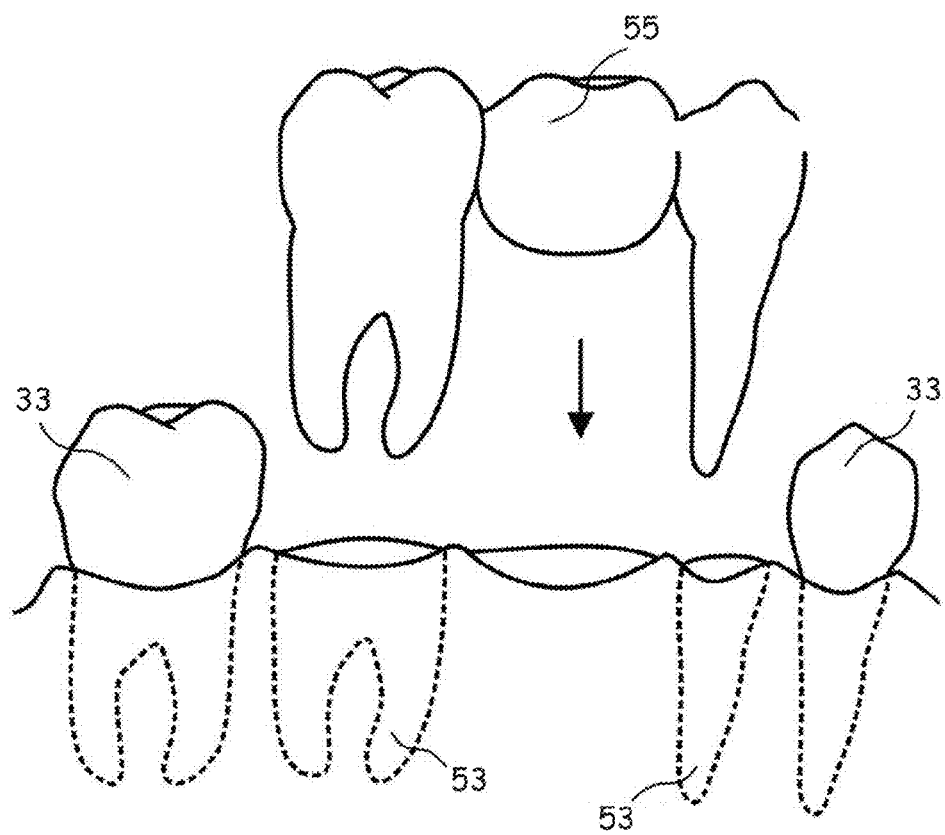
FIG. 10 is a view of a bridge according to an embodiment of the present invention.

The invention is not limited to the replacement of a single tooth. It is possible to manufacture dental bridges, whereby the lateral artificial teeth have root features that can readily be implanted into an existing socket. According to an embodiment of the present invention, the natural sockets 53 can be used as shown in FIG. 10 for attaching the bridge 55, with the adjacent teeth 33 staying healthy and complete. It is also possible to fabricate a partial prosthesis to be implanted into the natural socket, said prosthesis being the anchor for a later installment of a dental bridge. This embodiment is especially useful in cases where one of the two lateral supports of the bridge is already present, and the bridge therefore needs to be cemented.

According to various embodiments of the present invention, due to the ability of the suggested manufacturing processes, a respective embodiment of the invention allow the fabrication of prostheses representing crowns, roots, bridges, segments or any combination thereof, and also the entirety of a dentition.

Figure 11:
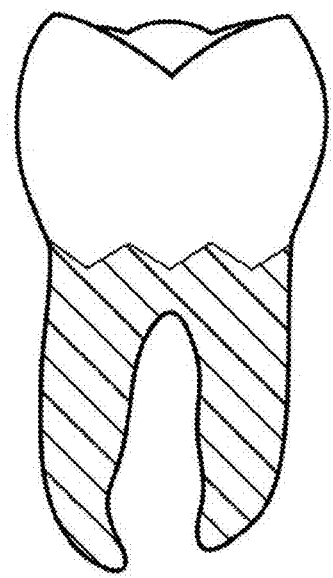
FIG. 11 is a view of a segmented artificial tooth, the segment representing the root and the segment representing the crown having an interlocking connection.

In yet another embodiment, the artificial root will comprise a feature on its occlusal-facing surface shaped in a way that it allows for assembly of a conventional veneer or a pre-manufactured veneer or crown to the root. The occlusal-facing surface can also be shaped to provide an interlocking connection to the crown as shown in FIG. 11. The shape of the interlocking joint can have a straight geometrical contour (as shown in FIG. 11) or can be fully individualized to the patient's needs.

In another embodiment, the shape of the artificial root will not completely reflect the shape of the root to be replaced. In order to strengthen the connection with the perio-type or periodontal ligament or the bone, the shape will be modified. If, for instance, the three roots of a molar are located very close to each other, the three roots will be replaced by only one root which will comprise parts of the original shape of the three original roots.

Figure 12:
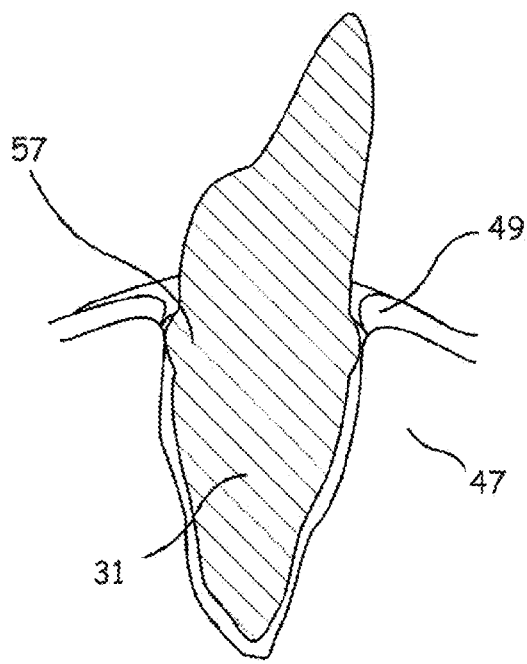
FIG. 12 illustrates a single-tooth prosthesis for osseointegration showing a custom shaped torus as a barrier against tissue growth.

According to an embodiment of the present invention, the prosthesis is manufactured in all its parts or as a single piece in its entirety before being integrated into the dental anatomy of the patient of interest. FIG. 12, for example, shows a tooth-shaped one-piece prosthesis having an integrated root portion and an integrated crown portion 31. The prosthesis 31 can be shaped with or without a custom shaped torus 57 that circumvents the prosthesis in a height of, for example, 0.5 mm below the line of gingiva 49. The torus 57 builds a barrier against in-growth of the gingival tissue. In case the prosthesis 31 is configured for osseointegration, the cavity in the bone 47 is virtually sealed, and osseointegration will take place without being disturbed by isolating lobes of gingival tissue growing between the prosthesis and the cavity. In case the prosthesis 31 is configured for perio-type integration, the gap between the prosthesis and the extraction socket is sealed against fast growth of gingival tissue, so that the integration into the perio-type or periodontal ligament structures, having a reduced growth rate in comparison, is protected.

Figure 13:
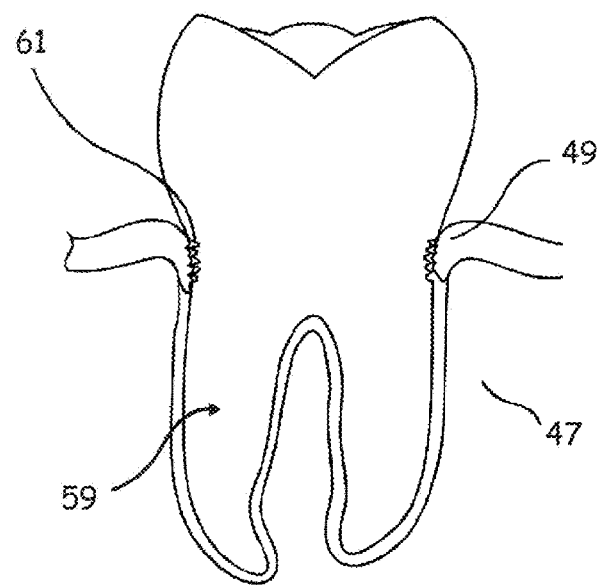
FIG. 13 illustrates a single-tooth prosthesis showing a labyrinth-sealing feature between a single-tooth prosthesis and the gingiva as barrier against bacteria infiltration.

In another embodiment as shown in FIG. 13, the prosthesis 59 has a sealing feature 61, which is circumventing or partially placed between the crown portion and the root portion of the prosthesis 59. The sealing feature 61 is either simply an indent (e.g. one or more circumventing grooves) or a labyrinth feature that builds the interface between the material of the prosthesis and the gingiva 49. The respective interface seals the structure between the prosthesis and the extraction socket against bacteria infiltration in order to gain long-term stability and to avoid pockets.

Figure 14:
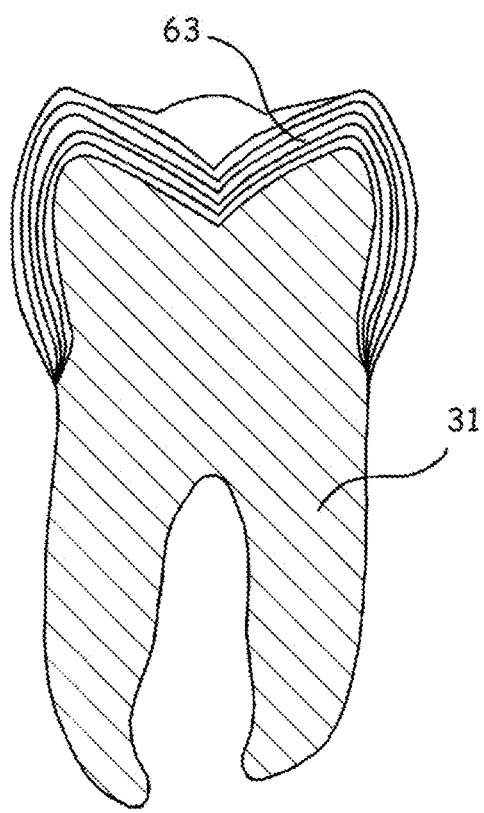
FIG. 14 illustrates a single-tooth prosthesis showing a build-up of a crown portion of translucent ceramic layers.

In another embodiment, the crown portion of a prosthesis is fabricated in an undersized shape compared to the final shape of the temporary or permanent crown of the prosthesis. Single or multiple layers of translucent ceramics are added in a laboratory process to gain esthetic performance compared to the appearance of a natural tooth. FIG. 14, for example, is a single tooth prosthesis having an undersized crown shape 31 and a build-up of several ceramic layers 63. It is also possible to use other esthetic materials having one or more than one layer. In another embodiment, the build-up 63 is, for example, made of elastic materials (like an elastic cover) in order to soften early contacts and foster in this way the healing process after integrating the prosthesis.

Figure 15:
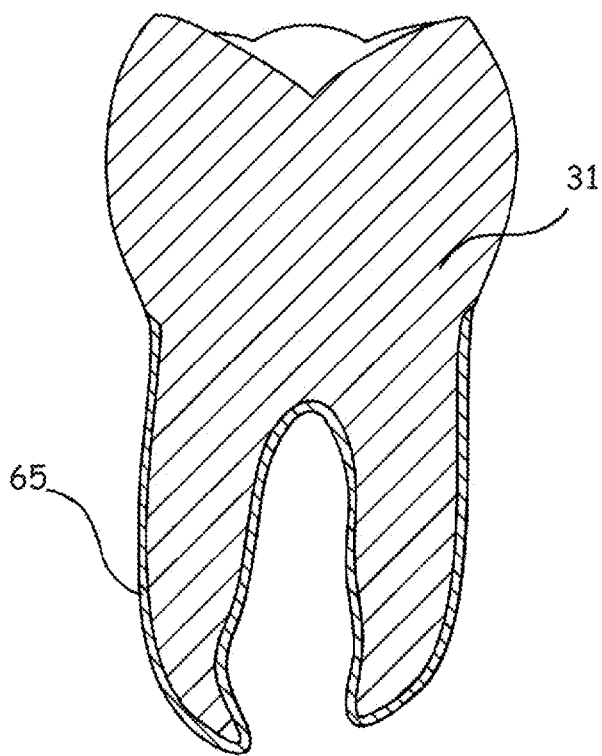
FIG. 15 illustrates a single-tooth prosthesis showing a root portion having drug releasing surface.

In yet another embodiment, the prosthesis includes a drug releasing surface, releasing over time medical substances. Such substances include, for example, one of the following: Antibiotic or other infection suppressing pharmaceuticals, growth promoting substances (for example, finally differentiated cells, ancestral cells, proteins, and cell parts of a human or animal tooth) or any combination thereof. FIG. 15 is, for example, a single-tooth prosthesis 31 having a drug releasing surface 65 covering at least a portion of the root part of the prosthesis 31.

In yet another embodiment, a prosthesis is fabricated based on imaging data of the patients dental anatomy. The imaging data includes three-dimensional representations of one tooth or two or more teeth. Each tooth includes a crown portion and root portion. The imaging data can be made either prior to or after extraction of the tooth or teeth to be replaced. The imaging data can include in-vivo data or data made in-vitro from one tooth or two or more teeth after extraction. Other imaging data are derived from physical impressions made of a dental anatomy. Dental anatomy includes the occlusion, the articulation, the geometrical (spatial) relationship between the teeth within one arch or between upper and lower arch of a patient, or parts thereof. Dental anatomy also includes the structures holding the tooth/teeth which include soft tissue structures and bone structures and any combination thereof. Imaging data can include two dimensional representations (for example, X-ray films, facial photos) or three-dimensional representations (like CT or MRT data). Imaging data can be any portion of the aforementioned data and/or any combination thereof. All these imaging data can be merged, overlaid and combined to derive shape data of a design of a prosthesis.

Figure 16:
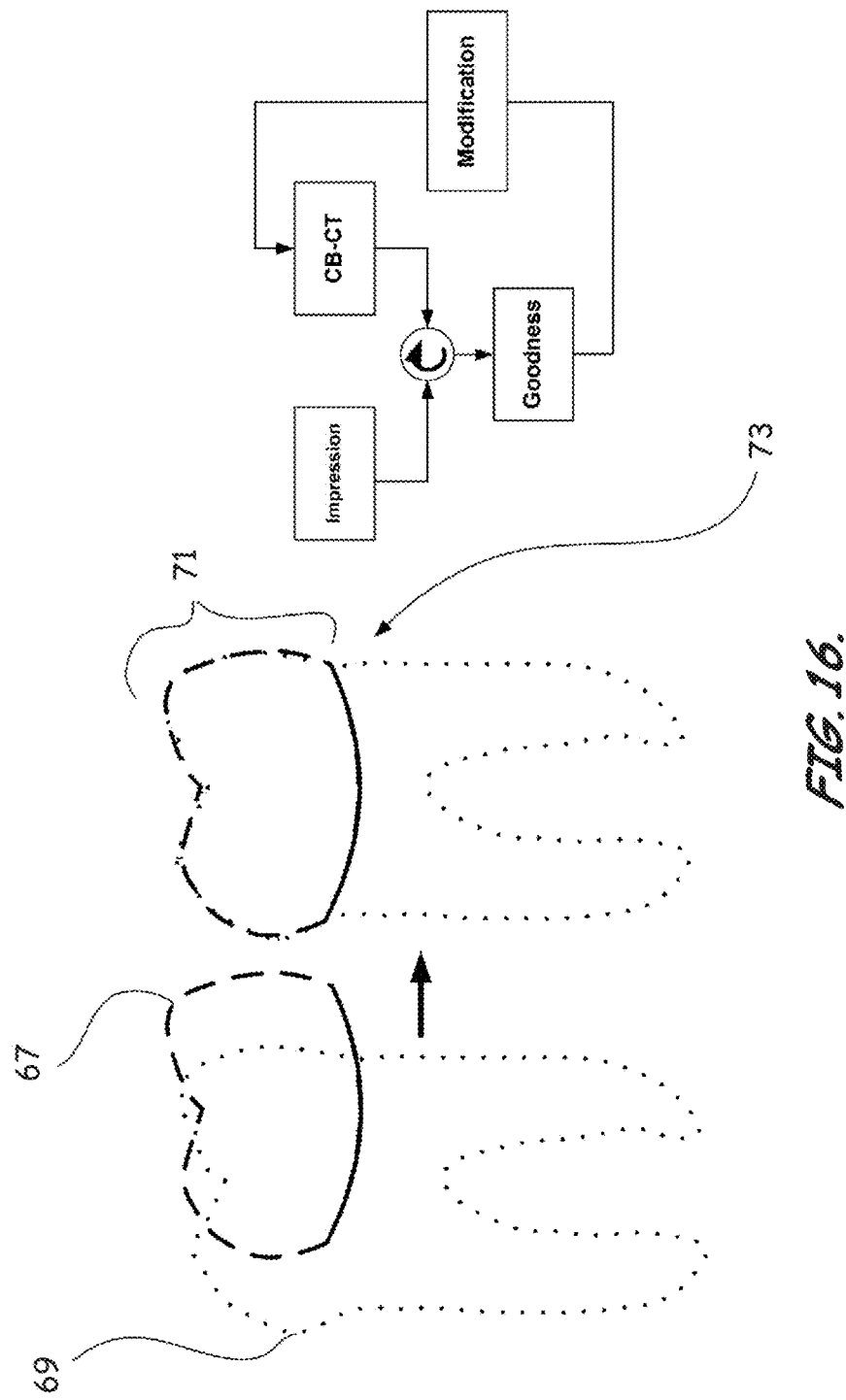
FIG. 16 illustrates an iterative method for processing previously acquired data for the fabrication of the mentioned prosthesis.

A further enhancement of the present fabrication process is shown in FIG. 16. Therein, two sets of surface-data are shown, i.e., surface-data of the crown portion 67 of the original tooth derived from the impression of the patient's denture and surface-data derived from the computed tomography image 69 providing information on the whole anatomy of the patient's non-functional tooth. It is to be noted that the uncertainty of the dataset provided by the impression lies at about 10 to 50 micrometer. The uncertainty of the dataset obtained from the computed tomography device shows an uncertainty within 200 to 300 micrometer. The impression data may include digital representations of the gum line surrounding the crown of interest.

Having these two types of surface-data, it is of interest to combine both datasets in the overlapping region 71, i.e., in the area of the crown portion. For this combination of datasets, the overlapping regions of the two datasets are placed together using best-fit algorithms. From the combination of the two datasets, a goodness/performance value of the fit is obtained as a value being calculated from the differences between the two datasets at corresponding points of the virtual prosthesis surface. Such a goodness value represents a measure representing the quality/performance of the fitting of the two datasets. For example, the sum of the distances raised to the second power could be used to calculate such goodness value of the best fit. From the combined dataset 73, the lower portion would represent the shape of lower accuracy derived from computed tomography data (image 69) while the upper portion 71 would represent the higher accuracy shape and the gingival line contour derived from the surface data of e.g. a digitized physical impression. From the combined data set 73 and the dataset 71, CNC-instructions are derived for the fabrication of the prosthesis or its components.

In the following, a procedure is described for enhancing the quality of the combined dataset. The proposed method/procedure executes the following steps: At first, the surface dataset derived from the impression (virtual crown) and the surface dataset derived from the computed tomography device data (virtual tooth with roots) are combined to one surface dataset of a virtual tooth. For this fitting combination a first goodness value is calculated that is saved electronically for further steps. Then, the surface data of the virtual tooth (combined dataset) is modified, e.g., blown up, biased, moved with respect to inclination and position etc. In a further step, the modified dataset of the virtual tooth is fitted to and combined with the original dataset of the impression. From this second combination of datasets, a second goodness value is derived. This second goodness value is saved electronically and compared to the aforementioned goodness value. If the new goodness value is greater, than the first goodness value, the aforementioned procedure is repeated. I.e., the second combined dataset is modified as before, e.g., blown up, biased, etc.

This iterative procedure (as shown in principle in FIG. 16) is repeated several times with different, e.g., systematically or randomly chosen modifications being applied to the respective combined dataset. In doing so, it is a goal to find or identify a maximum goodness value, e.g. employing the least-squares method" in cases where the sum of the multiple local distances between corresponding portions of each data set, each raised to the second power, is used. For this search of the maximum goodness value, many kinds of statistical methods and mathematical optimization methods can be utilized in which the kind of modifications and the directions of modifications are derived from adaptive algorithms based on the kind of modification and its direction and the gradient of the quality (i.e., the goodness value) calculation the goodness value iteratively.

As shown, for example, in FIGS. 17A-17C, the shape design of mass-produced implants of a single tooth prosthesis 87 shows a standardized joint 77 between the implant 75 and the crown portion 78. While the crown is usually custom-shaped to the adjacent and opposite teeth, the implant 75 is not. Therefore, the joint between such traditional crowns and implants is non-customized. Such joints are usually shaped with standardized cylindrical, hexagonal, and conical shape portions, either concentric or symmetrically shaped in the vertical component of outward facing runout of the joint 77. E.g., the hexagonal rising 79 described to serve as prosthesis interface having a generic shape.

According to conventional methodology, in order to obtain a positive lock between the implant and the crown, numerous standard form joints are manufactured in order to try to cover a majority of the possible crown designs. This, however, results in significant additional manufacturing costs and difficulties in inventory management. Alternatively, a smaller number of "standard" designs are manufactured designed to cover most cases. Although the smaller number helps reduce inventory management problems and manufacturing costs, it has been found too often lead to inadequate joint connections and in increased number of collisions between components as the clinician is often provided an improperly fitting connection. That is, the joint having a smaller footprint than ideal is often employed in order to allow for adjustments due to the inadequate connection, or the occlusal raising does not support the anatomy of the crown to be placed thereon. Recognized, therefore, by the inventors is the need for a custom joint which can provide a good positive lock between the implant and the crown/intermediate abutment, and which can maximize the "footprint" between the connecting pieces. Also recognized by the inventors is that an optimal positive lock can be established by custom shaping the joint to reflect the general shape of the crown.

FIG. 18 illustrates a natural tooth having a natural enamel crown 81, a natural dentin root 83 and the natural juncture between dentin and enamel 85 showing an individual asymmetric outer contour line. FIGS. 17B-17C illustrate an implant 75 having a cross-section showing a cylindrical or respectively slightly conical screw portion having concentric convolutions or threads 87 and having an occlusally facing generic prosthetic interface including a symmetric and generic hexagonal rising 79, and showing a symmetric and generic scallop-shaped surface 89 having a symmetric and generic shaped edge 77 between the surface 89 and the concentric outer screw shape as an attempt to account for an anatomical 3D curvature of the gum line. Each of these features are shown in top view in FIG. 17C. FIG. 17A shows a prosthetic crown 75, which is affixed to the aforementioned hexagon rising (not shown in this view) of the prior art implant 87.

The inventors, however, recognize the limitations of such anatomically shaped mass-produced implant joint portion where a limited amount of standardized shape is supposed to fit all individual situations of the patients of interest in the limitations of utilizing a scallop-shaped surface having a symmetric and generic shaped edge to try to account for the anatomical curvature of the gum line.

Accordingly, various embodiments of the present invention provide apparatus and methods of manufacturing or otherwise providing a custom prosthesis interface having a three-dimensional surface shape positioned and formed to create a form locking fit with respect to the crown/abutment and the implant body, which can maximize or at least significantly increase the footprint of the locking fit, which can reduce and/or eliminate collisions between manufactured components, and which allows individualized stocking—thus, eliminating the need to manufacture multiple potential versions of the joint. Various embodiments of the present invention also provide an asymmetrical shaped to account for the gum line.

The "One-Piece" Dental Implant/Prosthesis

Figure 19:
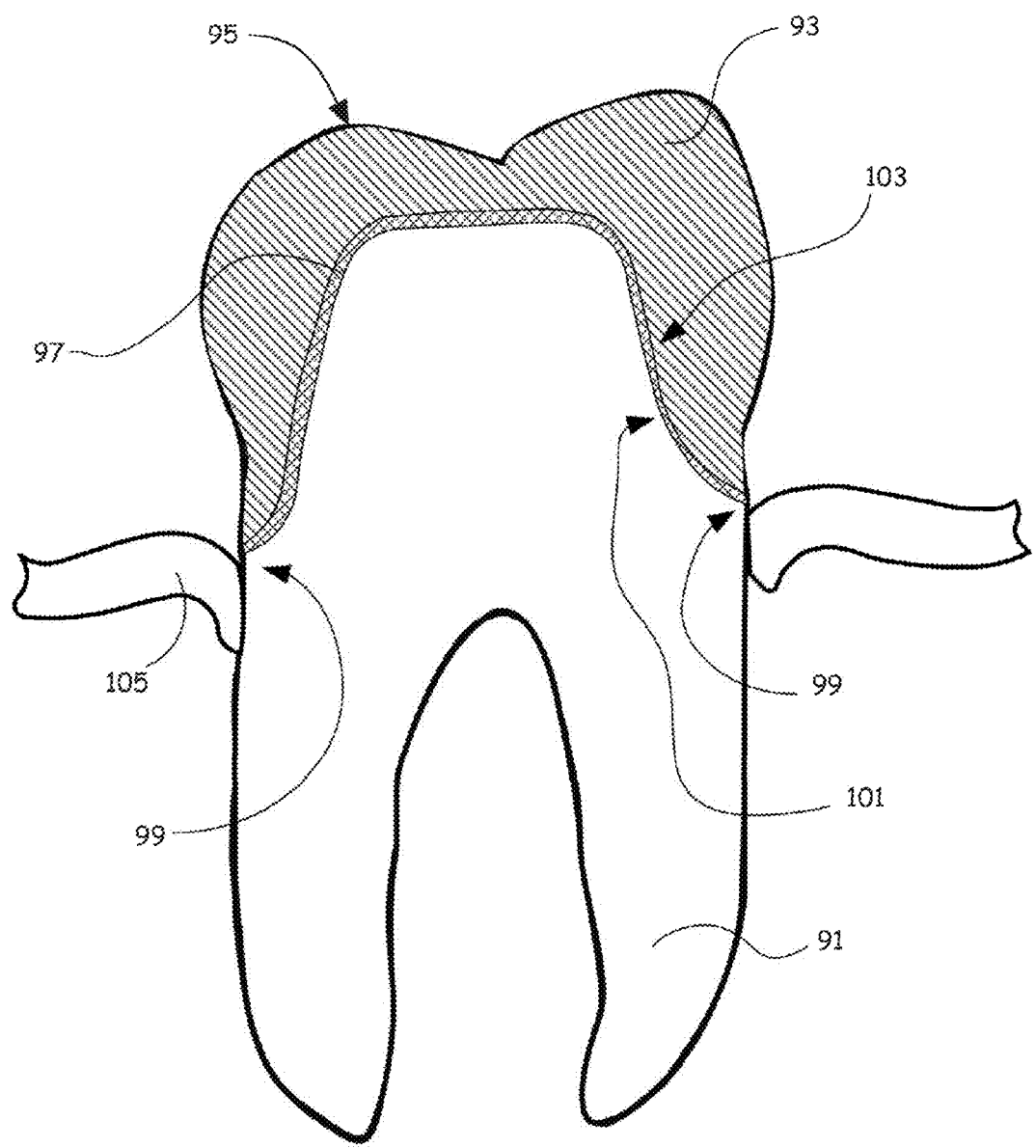
FIG. 19 illustrates a dental implant prosthesis with a custom-shaped joint between an implant body (having a root portion and an transgingival portion) and a crown.

FIG. 19 illustrates a cross-sectional view of an exemplary embodiment of a one-piece dental prosthesis 95. The term one-piece refers to the root body 91 portion and the crown cap 93 which are assembled as a one piece body 95. The body 91 is mainly composed of a ceramic material. This ceramic material as described herein can be pure zirconia, or a ceramic matrix composite like yttria-stabilized (tetragonal phase) zirconia (e.g., Y-TZP zirconia, NaceraZ Medium/Ivory, Doceram), alumina-toughened zirconia (e.g., ATZ zirconia, ZIRALDENT®, METOXIT) or zirconia-toughened alumina. On the top of the one piece body 91, a translucent cap, the crown cap 93 made of feldspar ceramics, lithium disilicate ceramics, highly translucent yttria-stabilized (tetragonal phase) zirconia, or resin nano ceramic technology materials (e.g., IPS e.max CAD HT—highly translucent, IPS e.max CAD LT—low translucent, available in various color shades, Ivoclar Vivadent, Z-CAD HTL, METOXIT, Lava Ultimate, 3M ESPE), is placed and attached with adhesive means at 97. This is, for example, a temporary silicon based adhesive (e.g., TempoSIL®2, coltène whaledent), a temporary non-silicon based adhesive (e.g., eugenol-free cement, e.g., RelyX™ Temp NE, 3M ESPE) for temporary use, or a permanent cementation (e.g., RelyX Unicem, 3M ESPE) for definite use. The spacing between the one piece body 91 and the translucent glass cap 93 can be adjustable depending on the adhesive material used for the attachment of the crown cap 93 onto the ceramic body 91. In an exemplary embodiment, the gap is 100 microns. An advantageous range is between 50 and 200 microns. In an alternative embodiment, for example, when non resin materials are used for the crown cap 93, the adhesive material at 97 can be composed of glass solder (e.g., Hotbond Tizio silicate coating and Hotbond Plus, DCM), where the parts are fused together utilizing a hot-bond process. In the process of integration, the one-piece dental prosthesis 95 can be placed into the alveole as a whole. Note, this is in contrast to procedures used with state of the art dental implants where a root portion is integrated and in a further step a crown portion is attached to the root portion. In order to prepare the surfaces of interest for non-fused connection, a cold-processed tribochemical method for silicatising surfaces may be applied (e.g., Rocatec Plus by 3M ESPE). The silicatised surface is prepared for bonding (e.g., cementing) by applying a silanising surface conditioning, i.e., a silane resin primer (e.g., ESPE Sil, 3M ESPE). Crown caps are traditionally individualized by manual manufacturing processes or directly or indirectly machined to fit the pre-existing preparation of a post stumps (on implants, implant assemblies, or natural teeth) prepared by the dentist inside the mouth or a patient. It has not been recognized until now by the inventors, however, that the occlusually-facing surface 101 of the actual implant body 91 can be optimally individualized prior to clinical insertion. This can be even of advantage when the rest of the shape of the implant body 91 is of generic shape, e.g. a traditional screw type dental implant. Further, it has not been recognized until now by the inventors that the apical-facing surface 103 of the crown 93 can machined responsive to data free-form created in a CAD system.

In an exemplary embodiment, a hot processed glaze finish (e.g., Crystall/Glaze and Crystall/Glaze Liquid, Ivoclar Vivadent) is applied to the non-resin translucent crown cap 93 prior to temporary or permanent bonding. Usually, a crown is bonded in the patient's mouth in the dentist's office. In an exemplary embodiment of the invention, the bonding takes place at the site of the manufacturer to thereby increase accuracy and the quality of the bonding itself.

Koebel et al. disclose in WO 2008/017472 a rough, porous osseoconductive topography of a zirconia implant surface that promotes bonding between the implant and tissue, where in a mixture, comprising of a polymer and at least one ceramic material is applied on a substrate, the mixture further comprising inorganic binders, e.g., phosphates, silicates, carbonates, sulfates. However, it has not been recognized until now by the inventors that dental implants, abutments, prostheses or parts thereof are individualized in its three-dimensional shape prior to such surface coating.

As noted above, the exemplary prosthesis 95 has an anatomically custom-shaped edge to the cross-section 99 adjacent the gum line, where the root-shaped outer surface portion corners to an occlusually-facing interface portion 101 to receive the crown cap 93. The joint line of the juncture 97 between the implant body 91 and the crown cap 93 shows in the cross-sectional view an individual, asymmetrical custom-shaped rising over the circumferential edge 99 curvature in the occlusal direction of the main longitudinal axis of the prosthesis. The occlusually-facing surface 101 of the implant body 91 correlates in its three-dimensional shape to the corresponding interface surface 103 of the crown cap 93, together creating a form-locking fit. Further, in an embodiment of the prosthesis, the individual, custom-shaped curvature of the outer joint (partially shown in the cross-sectional view as edge 99) is designed and manufactured to substantially follow either adjacent the gum line of the gingiva 105 of the patient or parallel to a bone crest shape, or a combination thereof.

The design process of both the implant body 91 and the crown cap 93 includes deriving from clinical imaging data representing the bone crest and/or the gum line, the virtual representation (i.e., the custom design) of the adjacent joint surface shapes 103 and 101 of the virtual representations of the implant body 91 and of the crown cap 93. In another method step, numerical machine control data are derived from the custom design of the joint shape and parts are machined (or made otherwise by rapid prototyping technologies) based on such numerical machine control data, the parts having physical joint shapes substantial to virtual custom design data.

According to the illustrated embodiment, the customized joint interface 97 between the implant body 91 and the crown cap 93 comprises a customized three-dimensional shape, i.e., a three-dimensional surface that separates the crown portion 103 from the root portion 101. In contrast to conventional joints between an detachable abutment and a crown, the illustrated joint is a customized joint actually between the implant body 91 itself and the crown cap 93, where at least the occlusally-facing interface member 101, manufactured prior to clinical insertion of the implant body 91, individually correlates to the dental anatomy of the patient's tooth to be replaced and the adjacent dental structures, including the gum lime, the bone socket, the adjacent and/or opponent crowns. This means that the points of separation along the juncture gum 105 at the intersection between the root portion i.e. the implant body 91 and the crown portion i.e. the crown cap 93 are individually designed, and in most cases, asymmetrical, instead of showing a generic symmetrical shape. Moreover, the course of the joint is individually form-fitted to the patients need and potential geometrical limitations and to complement the form of the crown cap 93 to be placed on the implant body 91. In an embodiment, the interfaces between such parts are sealed in order to provide a barrier against bacteria infiltration.

A problem occurs when both the implant body 91 and the crown cap 93 are fabricated in a parallel process. Both the implant and crown are fabricated based on data obtained from the scan and impression of the original denture. The customized joint interface 97 is then designed for both parts based on the aforementioned data. In such a parallel fabrication process however, small fabrication failures and inaccuracies can lead to two joint portions (i.e., two three-dimensional surfaces of the implant body and the crown portion) that in some cases do not totally fit together. This is especially an issue when the two parts are both made of hipped (HIP) zirconia since only small corrections can be applied to such a material. In an exemplary fabrication method of the aforementioned prosthesis 95, the implant body 91 and the crown cap 93 are instead fabricated in a serial fabrication process. Therefore, in a first step, the implant body 91 is fabricated with a customized surface forming the root portion and the joint portion 101. In a further step, the three-dimensional surface is scanned or an impression prior to clinical insertion is taken, thereby, acquiring data that actually represents the embodiment of the customized joint as it is embodied in the fabricated implant body 91. The data obtained from the scan of the customized joint 97 is then utilized for the fabrication of the crown cap 93 interface member 103 having a customized joint portion that fits to the joint portion 101 of the implant body 91 with a high accuracy.

In contrast, in a common process using CAD/CAM technologies to make dental crowns and bridges, the process receives the custom shape of the tooth preparation to form the joint between the natural tooth or even of a custom shaped abutment. Such joint shapes, however, are not custom generated or designed (i.e., originated) in the virtual domain, but rather are physically man-made and shaped by the doctor of record in the mouth of the patient of interest. Even when new state-of-the-art abutments having the transgingival middle-pieces that connect the implant screw with the crown are custom shaped with respect to the outer shape that finally receives the crown, the implant facing joint/interface surface of such abutment is of a three-dimensional standard (i.e., non-custom) geometry.

Figures 20A, 20B:
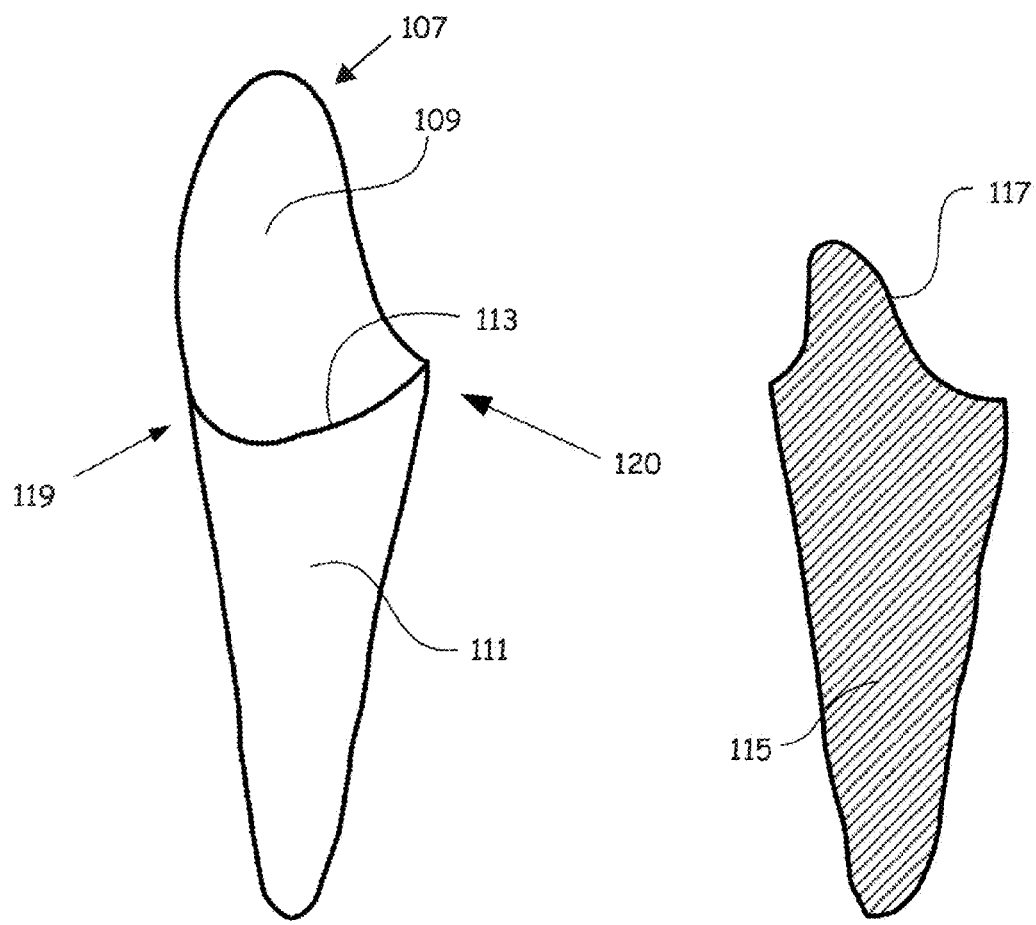
FIGS. 20A and 20B illustrate a proximal lateral view of a dental prosthesis and a cross-sectional lateral view of the dental implant body, respectively.

FIG. 20A shows a proximal lateral view of a dental prosthesis 107 having a crown portion 109 and a root-shaped implant body 111, being separated at a junction that shows up as a circumferential line 113 in the view of the figure. FIG. 20B also shows a cross-sectional lateral view 115 of the dental implant body 111. In the cross-sectional view 115 of the implant body 111, illustrating that the surface line 117 of the occlusally facing surface is asymmetric, having a different slope or steepness on one side compared to the slope or steepness of the other one side. In the proximal lateral view, the circumferential line 113 is also asymmetrical, having a different slope or steepness in the direction of the labial height of the line at 119 compared to the slope or steepness in the direction of the lingual height of the line at 120.

Figure 21:
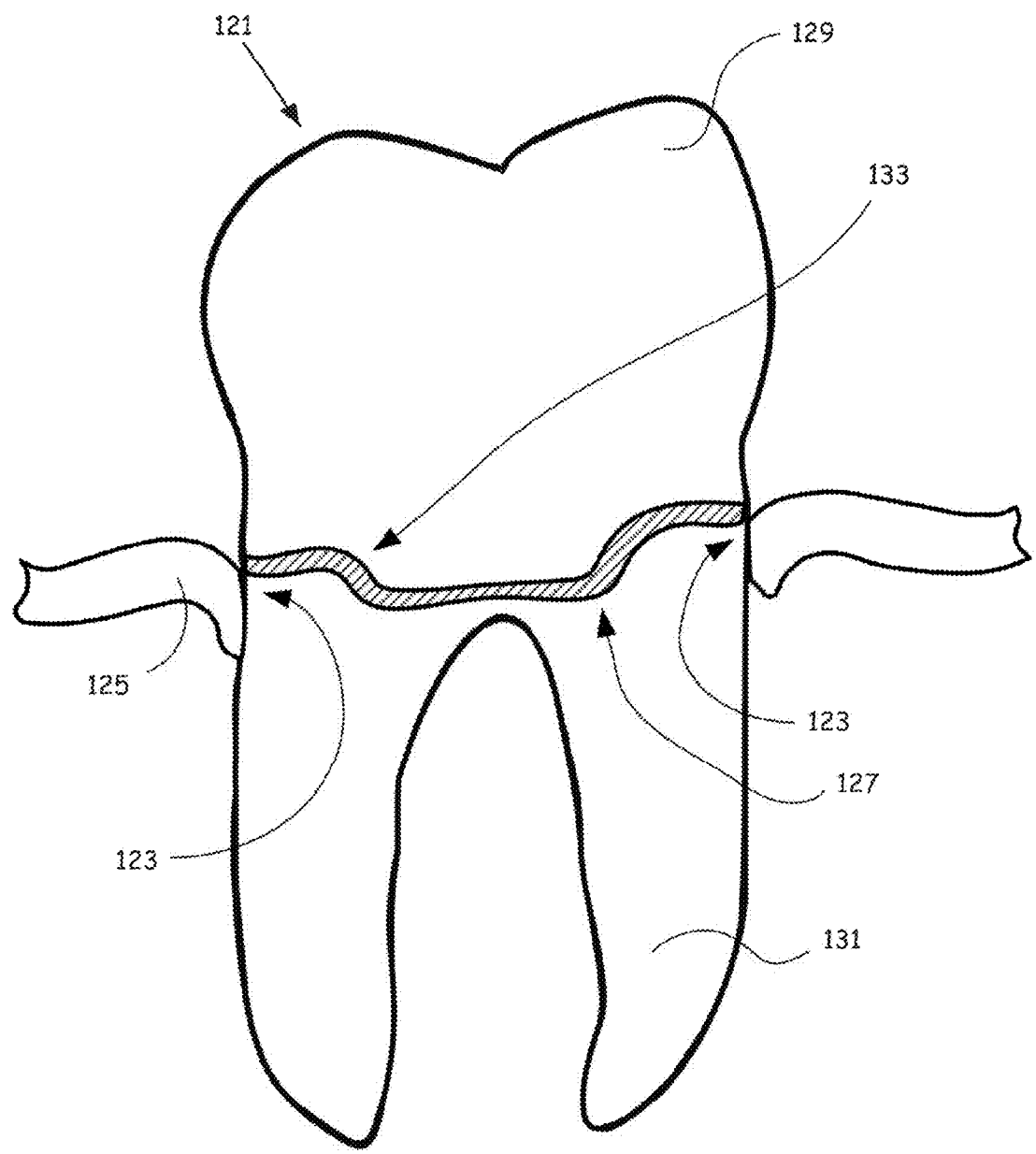
FIG. 21 illustrates a dental implant prosthesis with a custom-shaped joint between an implant body (having a root portion and an transgingival portion) and a crown.

FIG. 21 illustrates a cross-sectional view of another exemplary embodiment of the present invention. The implant body 131 of the prosthesis 121 has an anatomically custom-shaped edge to the cross-section 123 adjacent the gum line of the gingiva 125, where the root-shaped outer surface portion of the implant body 131 corners to an occlusually-facing interface portion 127 to receive the crown cap 129. The joint line of the juncture between the implant body 131 and the crown cap 129 shows in the cross-sectional view an individual, asymmetrical custom-shaped indent over the circumferential edge 123 curvature in the apical direction of the main longitudinal axis of the prosthesis. The occlusually-facing surface 127 of the implant's body 131 correlates in its three-dimensional shape to the corresponding interface surface 133 of the crown 129, together creating a form-locking fit. Further, in an embodiment of the prosthesis, the individual, custom-shaped curvature of the outer joint (partially shown in the cross-sectional view as edge 123) is designed and manufactured to follow either substantially adjacent the gum line of the gingiva 125 of the patient or substantially parallel to a bone crest shape, or any combination thereof.

Designing the "One-Piece" Dental Implant/Prosthesis

Figure 22:
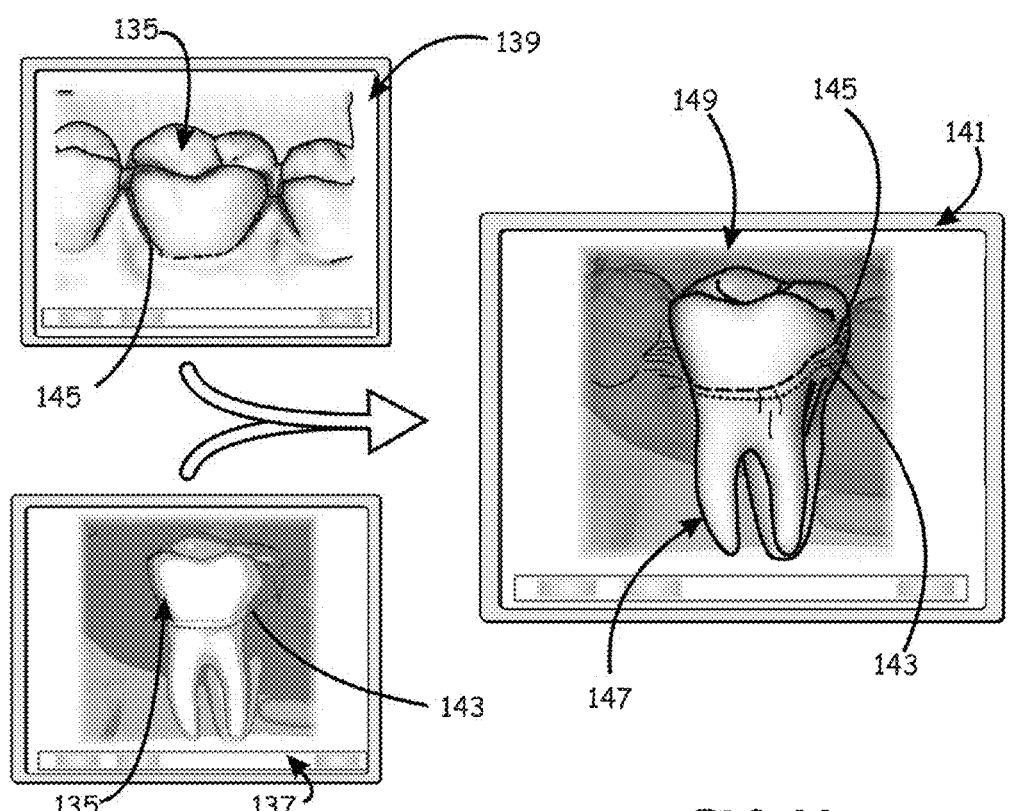
FIG. 22 illustrates numerically combining surface image data with an x-ray image data with the help of a computer to form a three-dimensional virtual model.

FIGS. 22-27 illustrate an example of a method of designing the "one-piece" dental implant 95 (shown in FIG. 19) formed of "two" major pieces to replace a non-functional natural tooth 135 positioned in a jawbone of a specific pre-identified patient. As shown in FIG. 22 the "one-piece" and "two-piece" design methods can include the steps of receiving data describing a three-dimensional X-ray image 137 of at least portions of the patient's dentition (x-ray image data), and receiving data describing a surface scan of a dental anatomy and/or a physical impression of the dental anatomy at 139, defining impression image data made prior to removal of the non-functional natural tooth from the jawbone of the specific patient. The steps can also include forming one or more three-dimensional virtual models at 141 of at least portions of the non-functional natural tooth 135, for example, by combining the x-ray image data of the x-ray image 137 (including the location of the bone crest line/bone-facing gum line 143) and impression image data of the surface impression image at 139 (including the location of the outer gum line 145), and forming the three-dimensional virtual model or models at 141 of the non-functional natural tooth 135 to include a modeled virtual root portion 147 and a modeled virtual crown portion 149 modeled or otherwise designed based upon to the x-ray image data of the x-ray image at 137 and the impression image data of the surface impression image at 139.

FIGS. 23-27 further detail exemplary steps of designing the one-piece dental implant based upon the three-dimensional virtual model 141 of at least portions of the non-functional natural tooth 135. The steps of designing the dental implant include the steps of forming a virtual dental implant body 151 (FIG. 27) modeling a physical dental implant body having a virtual prosthesis interface at 153 (FIG. 26) modeling a physical prosthesis interface of the physical dental implant body to receive an occlusally-facing dental prosthesis component 163. The step of forming a virtual dental implant body 151 can include forming the virtual prosthesis interface (at 153, FIG. 26) to have a three-dimensionally contoured implant body surface shape at least partially correlated to a surface shape of an occlusally-facing surface of the modeled virtual crown portion 149 and crown surface of the nonfunctional tooth 135.

Figure 23:
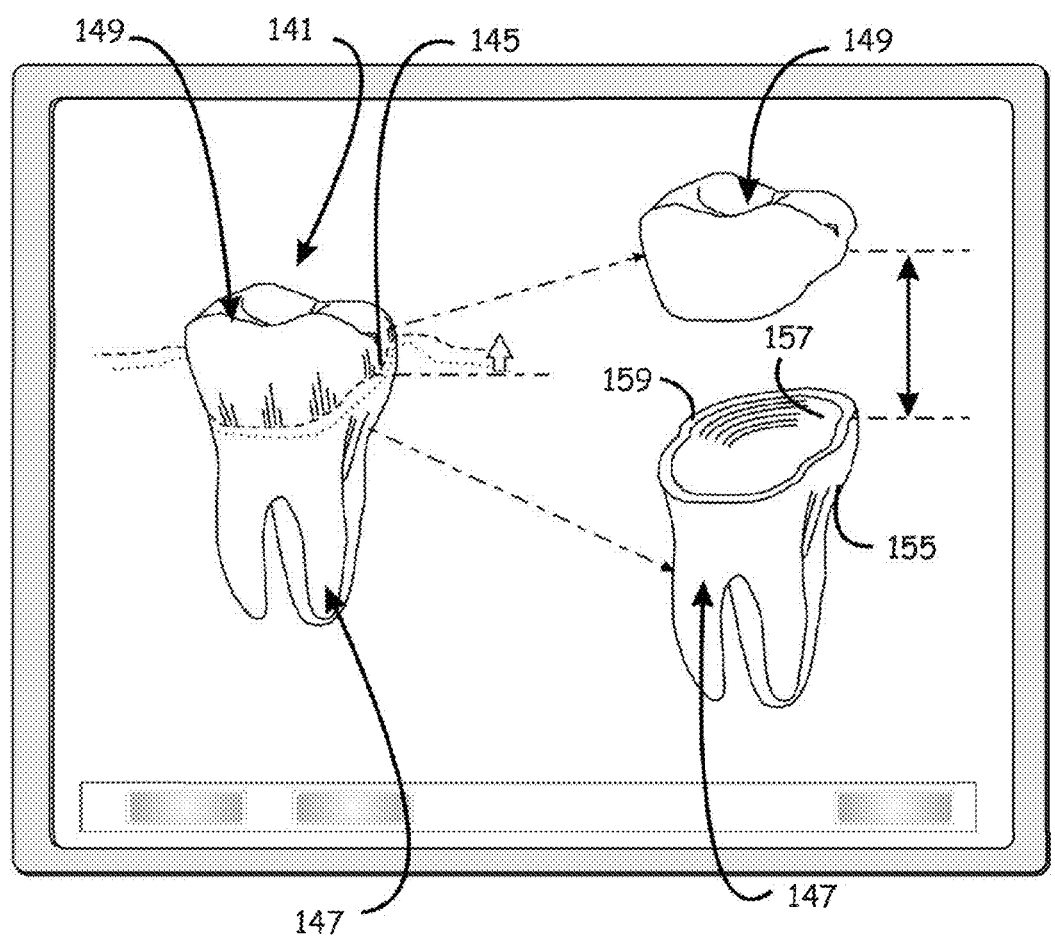
FIG. 23 illustrates the division or separation of parts of a virtual model.

As perhaps best shown in FIG. 22, according to an exemplary one-piece, two-part dental implant body configuration, the step of forming a virtual dental implant body 151 can include separating a portion of the three-dimensional virtual model (including the modeled virtual root portion 147 and modeled crown portion 149) along a virtual outer gum line representation 145. Note, according to the illustrated configuration, the separation/transformation procedure performed on virtual model at 141 can include both digital cutting and digital thickening of the components 147 and/or 149 to the inside while maintaining the dimensional integrity of the outer surface. For the two-piece example, this results in the root portion 147 having a non-infinitesimal thickness as shown, i.e., having a thickness of a substantial dimension. The virtual root portion 147 shown in FIG. 23 is represented in digital surface data format e.g., STL, is defined by an outer shell 155, an inner shell 157, and an occlusally-facing connecting surface 159. The design process step of thickening, generally employed in both two-piece and the three-piece configurations, creates an inner (smaller) second shell, and then generates the surface boundary that shows the thickness.

As perhaps best shown in FIGS. 24 and 26, the step of forming can also include copying at least portions of the modeled virtual crown portion 149 to form a base shape of the virtual prosthesis interface, reducing dimensions of the at least portions of the modeled virtual crown portion 149 to define a virtual prosthesis interface model at 161, and as shown in FIG. 26, combining the virtual prosthesis interface model 161 having reduced dimensions with the virtual root body portion 147 to form the virtual dental implant body 151 having a virtual prosthesis interface 153.

As shown in FIGS. 24-25, according to this configuration, the steps can also include forming the virtual occlusally-facing dental prosthesis component 163 (FIG. 27) modeling an occlusally-facing dental prosthesis component, such as, for example, a virtual crown component 163. According to such configuration, the step of forming the virtual crown component 163 includes forming a complementing virtual dental implant body-receiving (interface) surface 165 (FIG. 25) modeling a physical complementing interface surface to receive occlusally-facing portions 153 of the dental implant body 151 to create a form locking fit therebetween. This can be accomplished by copying at least portions of the modeled virtual crown portion 149 to form a base shape of the complementing interface surface 165 of the virtual crown portion 163, reducing dimensions of the at least portions of the modeled virtual crown portion 149 to form the complementing interface surface model shown at 167 (FIG. 24), and combining the virtual crown portion model 149 with the complementing interface surface model 167 as shown in FIG. 25 to form the virtual crown portion 163 shown in FIG. 27. Note, the virtual crown component 163 (FIG. 27) can extend in the apical direction to, for example, the virtual outer gum line representation 145 (FIG. 23). Also, the aforementioned step of combining the virtual crown portion model 149 with the complementing interface surface model 167 as shown in FIG. 25 to form the virtual crown portion 163 shown in FIG. 27, can include a design step to close potential gaps between the two outward-facing interface shells that form substantially the virtual crown component 163 (FIG. 27).

As shown in FIG. 24, the dimensions of the complementing interface surface model 167 is reduced by the material thickness of the crown cap (at least 0.5 mm in thickness in this example) to be by this amount smaller than the dimensions of the virtual crown portion 149, and the dimensions of virtual prosthesis interface model 161 is reduced to be smaller than the dimensions of the complementing interface surface model 167. These dimensional reductions in the three-dimensional size of the pairs of surfaces 167 and 161 that build an interface and/or form the form-locking fit, are to account for manufacturing tolerances and to account for a certain thickness of the layer of adhesive, cement or glass solder, etc., generally in the range of 50 to 300 micrometers, but preferably approximately 100 micrometers.

The Compound Dental Implant/Prosthesis

Figure 28:
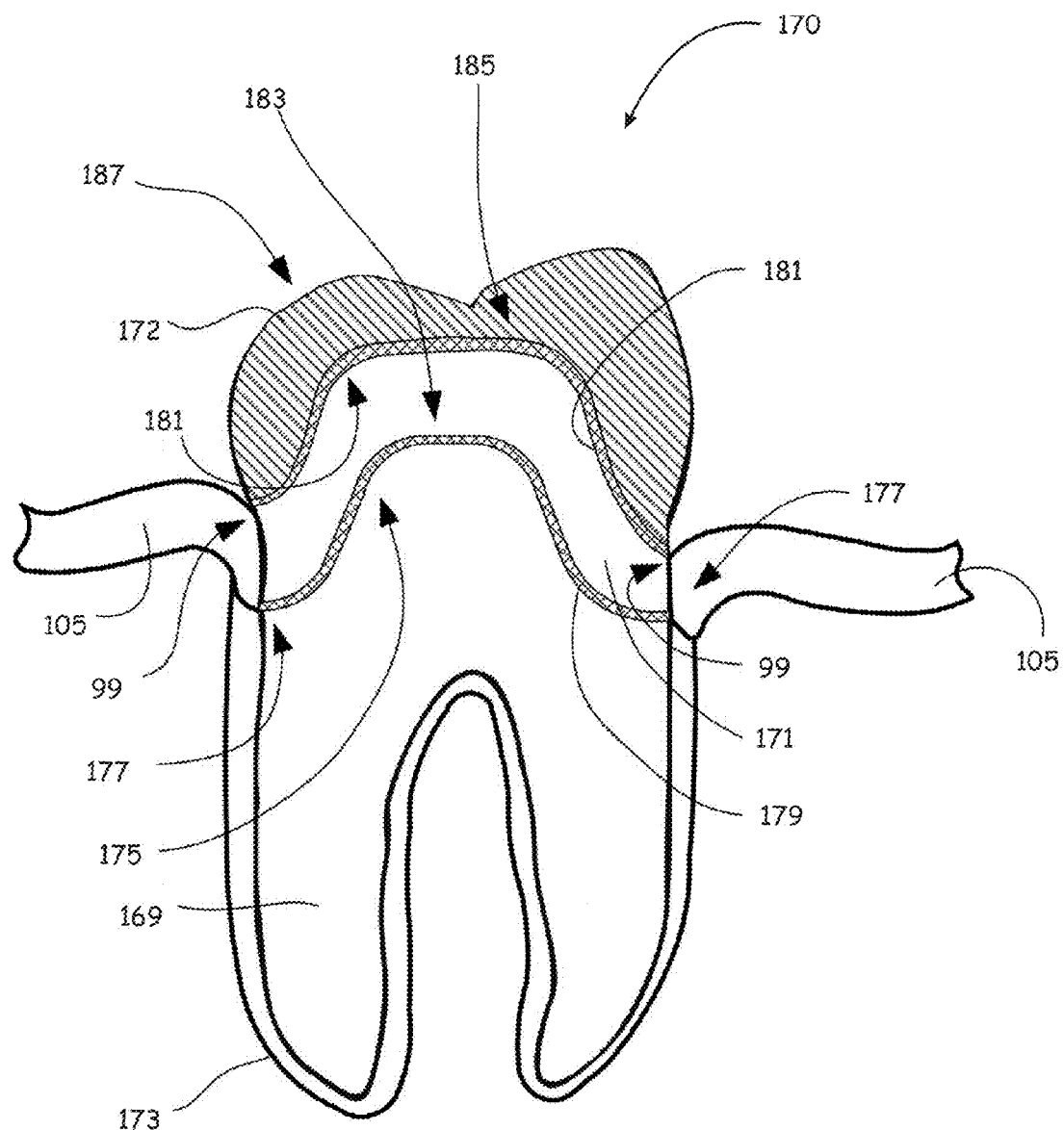
FIG. 28 illustrates a compound one-piece prosthesis with a first joint between an implant body and a transgingival cap and a second joint between the transgingival cap and a crown.

FIG. 28 shows a cross-sectional view of a single tooth prosthesis 170 which is a variant of the embodiment of the dental prosthesis shown and described in context of FIG. 19 and shows a compound one-piece prosthesis with a first joint between an implant body 169 and a transgingival cap 171 and a second joint between the transgingival cap 171 and a crown 172. The partially root-shaped implant body 169 matches the extraction socket 173 of a pre-identified patient, without interfering with or intruding into the surface socket itself. The implant body 169 is formed of, for example, commercially pure titanium (e.g., medical grade 2 commercially pure titanium) or a medical-grade titanium alloy (e.g., $Ti_6Al_4V$). The middle piece, the transgingival cap 171, is made, for example, of ceramic material e.g., Y-TZP zirconia or ATZ zirconia, and serves a similar purpose of an abutment in traditional dental implantology. In an exemplary embodiment, the transgingival cap 171 is favorably tooth colored, e.g., in its white body state, prior to final sintering by volumetric coloring (e.g., color liquid e.g., Zirkon B4; C3; D4, Zirkonzahn).

Further, in the exemplary embodiment, the implant body 169 and the transgingival cap 171 are fused together by the above described hot-bond technology, where the titanium surface of the interface 175 is first silcatized by a coating applied in a heating process (e.g., Hotbond Tizio silicate coating), then the two parts of interest 169 and 171 are glass soldered (e.g., Hotbond Plus, DCM), building together a fused extended implant body. In addition, the zirconia surface of the interface 183 can also be first silcatized by a coating applied in a heating process (e.g., Hotbond Zirconnect silicate coating). The outer joint line (shown as an edge 177) in the cross-sectional view of the joint 179 is subgingivally positioned (typically at bone crest level or even partially intra-crestal) and the transgingival cap or abutment portion 171 is permanently fused and sealed reducing significantly the risk of an opening or gaping under load, and of bacteria colonization at the interface, compared to traditional implants. The interface between the transgingival cap and the crown at 99 is discussed in the context of FIG. 19. Although state-of-the-art abutments are partially customized in its outer interface surface 181, it has not been recognized until now by the inventors that the interface pairs 175 and 183 at the junction 179 can be to the patient's needs individually designed in a computer and subsequently fabricated to numerical data derived from that virtual interface design.

The embodiment of FIG. 28 has two fully custom-shaped joints or interfaces, the one 179 positioned sub-ginivally, e.g., at the bone crest level, and the second 181 positioned iso- or supra-gingivally. Each pair of surfaces that build the two prosthetic interfaces (175 and 183) and (181 and 185) create a form locking fit. The respective three-dimensional surfaces (shown as cross-sectional view) dimensionally correlate with the outer three-dimensional shape 187 of the crown 172 and dimensionally correlate with each other. According to the exemplary configuration, the design of the shapes of both joints is created or originated in the virtual domain using the digital data representing the anatomical specifics of interest. There is a minimal thickness of 0.2 mm to 0.5 mm (typically 0.3 mm) to be considered for the middle-piece i.e., the transgingival cap 171. In the exemplary configuration, the outer joint line of the interface between the implant body 169 and the transgingival cap 171 (shown in the cross-sectional view as edges 177) follows the saddle shaped 3D curvature of the bone crest adjacent the anatomical socket, while the outer joint line of the interface between the transgingival cap 171 and the crown 172 shown in the cross-sectional view as edges 99 follows the saddle shaped 3D curvature adjacent the gum line of the gingiva 105.

Again, this is not a standard curvature of a cylindrical mass-produced implant. To the very contrary, this design is individually performed per specific tooth of a pre-identified patient. The shape data are derived from clinical images of the dental anatomy of such patent. In this specific context, the design takes into account, the anatomical cross-section of the implant body 169 substantially matching the shape of the extraction socket, or matching the root of the tooth being extracted, and substantially perpendicular to that cross-section, the 3D curvatures of the two joints between the three parts (e.g., made of different materials) in the longitudinal axis of the dental tooth prosthesis. The substantially parallel gap between the two adjacent surfaces that build the interface is between about 100 microns and 300 microns (typically 200 microns) to accommodate a minimal thickness of the glass solder for the sub-gingival joint and for the cement for the iso- or supra-gingival joint. In a further exemplary embodiment, the shape of the surfaces of each joint extend the outer joint line to the occlusal plane (i.e., in the direction of the tip of the crown 172) to accommodate for a maximum stability for the assembly to withstand mastication forces. Note, applicable descriptions of FIG. 19 apply to the descriptions of FIG. 28 and vice versa.

Figure 29:
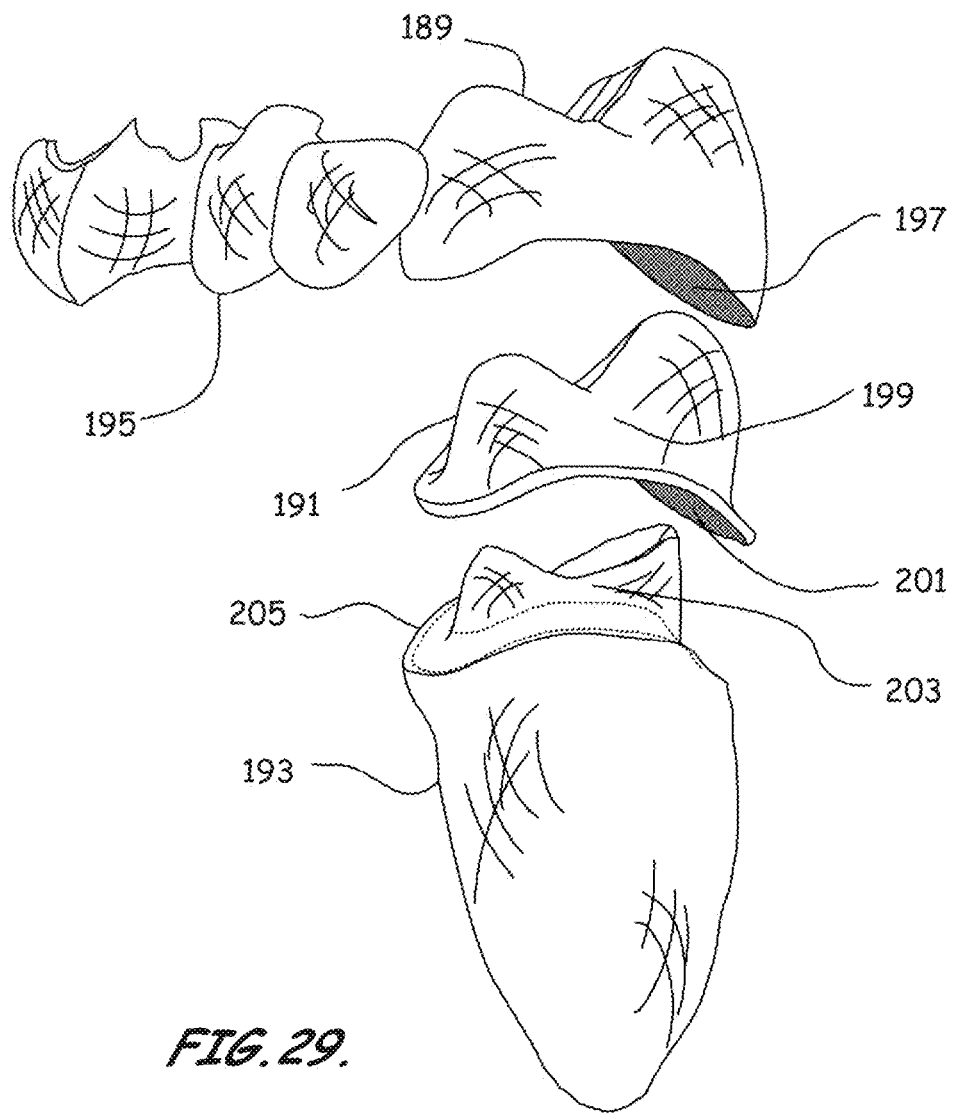
FIG. 29 illustrates an exploded view of a dental prosthesis consisting of a crown, a trans-gingival portion, an implant body, and a splint.

FIG. 29 shows an exploded view of a dental prosthesis having a crown 189, a trans-gingival portion 191, and an implant body 193, along with a splint 195. FIG. 29 further shows, for example, in principle, the three-dimensional extensions of the surfaces shown in cross-sectional view in FIG. 28 (although FIG. 28 represents exemplarily a dental prosthesis to replace a molar tooth, while FIG. 29 represents an exemplarily dental prosthesis to replace a premolar tooth). According to the illustrated configuration, each transversal and lateral cross-section of the components 189, 191, 193 and 195 are custom-shaped, having an individual three-dimensional shape that is substantial asymmetric, does not include generic concentric shapes, does not include generic symmetric shapes, and does not include convolutional shapes. The respective form-locking fit of the prosthetic interfaces between surfaces 197 and 199 and between surfaces 201 and 203 is clearly indicated for those skilled in the art. The outer circumferential edge 205 of the surface 203 varies in the direction of a mainly longitudinally axis of the implant body 193 and in transversal direction with respect to the distance to such longitudinal axis. For those skilled in the art, it is clearly indicated that the three-dimensional shapes of the aforementioned interface surfaces correlate with the outer surface of the crown 189 and with each other. The maximal transversal dimension of the implant body 193 adjacent the outer circumferential edge 205 is significantly bigger than the minimal transversal dimension of the implant body 193 adjacent the outer circumferential edge 205. In an alternative exemplary embodiment, the crown 189 and the splint 195 are integrated as one piece to form an integrated support device (described in detail later).

Figure 30:
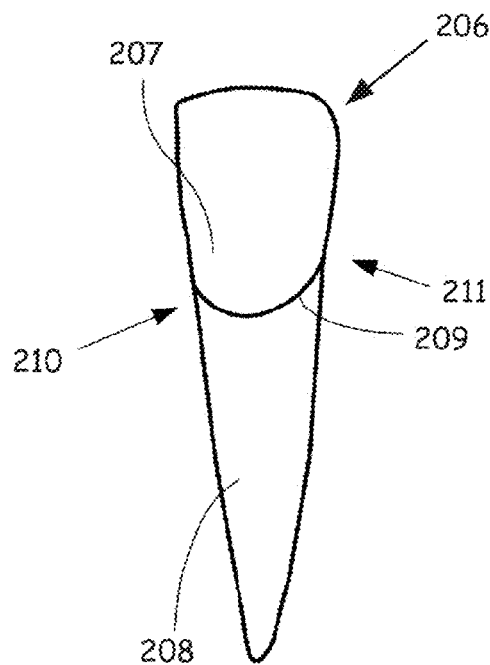
FIG. 30 illustrates labial view of a dental implant prosthesis.

FIG. 30 shows a labial view of a dental implant prosthesis 206 having an artificial crown portion 207 made of a translucent material colored at least similar to the color of a natural crown mimicking the shape of the natural enamel crown 81 of FIG. 18. The dental implant prosthesis 206 also has an artificial root portion 208 including an opaque material suitable for tissue integration and substantially mimicking the shape of the natural dentin root 83 of FIG. 18. The artificial crown portion 207 and artificial root portion 208 have a junction that shows in the view of the figure as a circumferential line 209 so that the runout of that juncture at 209 follows the natural juncture between dentin and enamel 85 shown in FIG. 18. In the labial view of the prosthesis 206, the circumferential line 209 is asymmetrical, having a substantially different slope or steepness in the direction of the proximal height of the line on one side 210 and to the slope or steepness in the direction of the proximal height on the other one side 211. In an alternative exemplary embodiment, the artificial crown portion 207 is in the form of either a temporary crown or a portion of an integrated support device (described in detail later) whereby the bonding wings to affix the integrated support device to one or more adjacent teeth are not shown.

Figure 31:
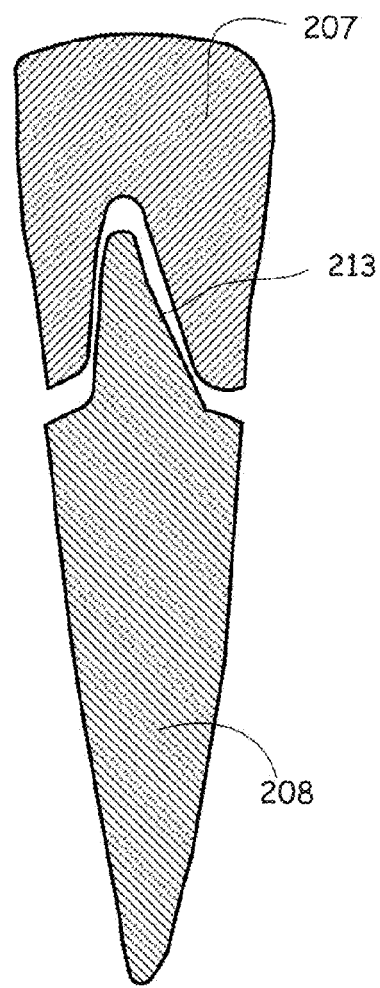
FIG. 31 illustrates cross-sectional labial view of a dental implant prosthesis.

FIG. 31 shows a cross-sectional lateral view of the dental implant prosthesis 206 having a crown portion 207 and a root portion 208 being shown separated at a junction 213. In the cross-sectional view of the prosthesis, the correlating surface lines that build the form locking fit of junction 213 are asymmetric, having a different slope or steepness on one side compared to the slope or steepness of the other one side.

Figure 32:
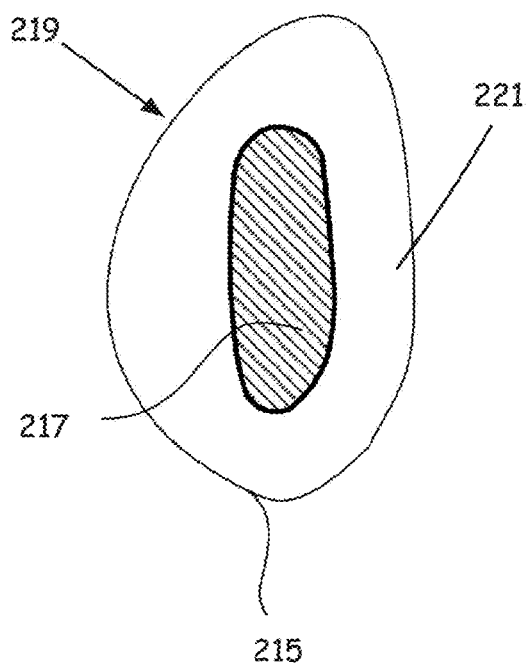
FIG. 32 illustrates a top view and a cross-sectional transversal view of a dental implant body.

FIG. 32 shows a top view 215 and cross-sectional transversal view 217 of a dental implant body 219. The maximal transversal dimension of the implant body shown in the top view is significantly bigger than the minimal transversal dimension of the implant body shown in the top view. Its outer circumferential contour is asymmetric as shown in top view. The cross-sectional view 217 indicates a transversal cross-section of the male portion surface 221, i.e., a positive rising, of the prosthesis interface that creates a form-locking fit to an occlusally facing prosthesis component (as shown for example, in FIG. 30). The maximal transversal dimension of the implant body shown in the cross-sectional view 217 is significantly bigger than the minimal transversal dimension of the implant body shown in the cross-sectional view. Its outer circumferential contour is asymmetric as shown in top view, and correlates in its shape and orientation to the outer shape of the top view 215.

Designing the Compound Dental Implant

FIGS. 33-39 illustrate an example of a method of designing the compound "one-piece" dental implant 170 (shown in FIGS. 28 & 39) formed of "three" primary pieces, based upon the three-dimensional virtual model 141 of at least portions of the non-functional natural tooth 135 (as already referenced in FIGS. 22 and 23). According to an example of the three-piece dental implant body configuration, as perhaps best shown in FIG. 33, the step of forming a virtual dental implant body 223 (FIG. 38) includes separating a portion of the three-dimensional virtual model 141 along the virtual bone-facing gum line representation 143 to form a modeled virtual root portion 225 and a first modeled virtual crown portion 227 (used to form the modeled transgingival cap portion), and copying a portion of the modeled crown portion of the virtual model 141 separated at the outer gum line 145 to form a second virtual crown portion model 229 modeling the physical crown.

Figure 34:
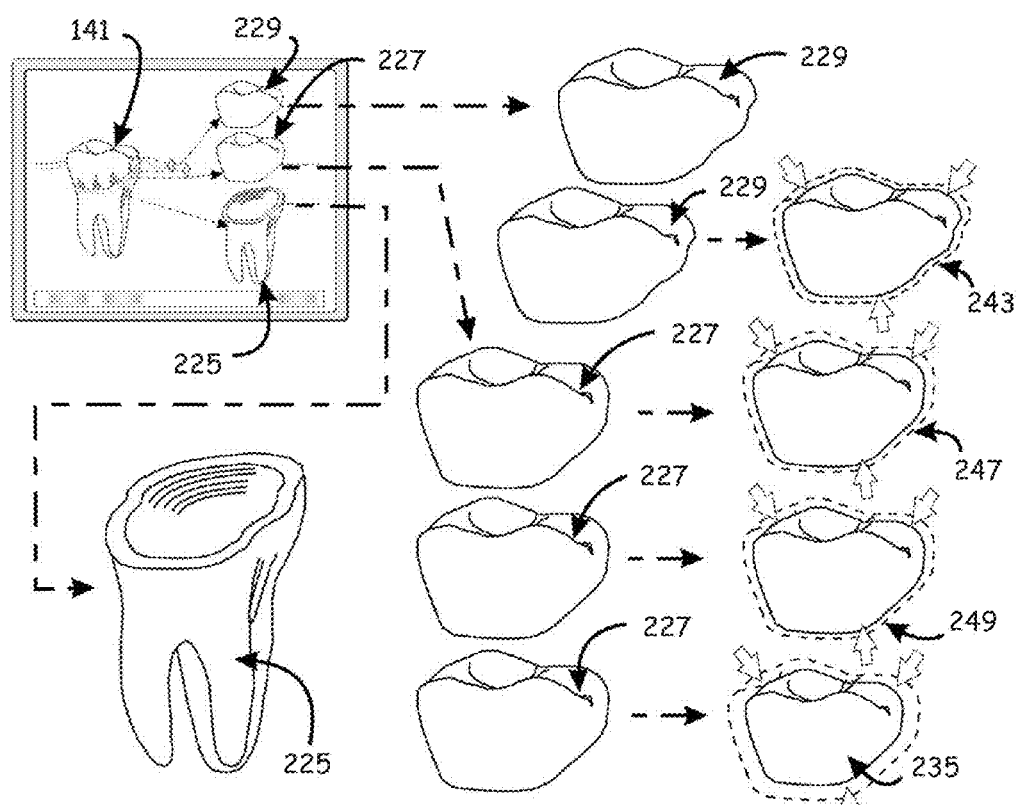
FIG. 34 illustrates copying of portions of the divided virtual model.

As perhaps best shown in FIG. 34, the step of forming the virtual dental implant body 223 (FIG. 38) further includes copying at least portions of the modeled first virtual crown portion 227 to form a base shape of the prosthesis interface 231 (FIG. 38 and reducing dimensions of the at least portions of the modeled first virtual crown portion 227 to define a prosthesis interface model 235. As shown in FIG. 35, the step of forming also includes combining the virtual prosthesis interface model 235 with the virtual root body portion model 225 to form the virtual dental implant body 223 (FIG. 38).

Figure 33:
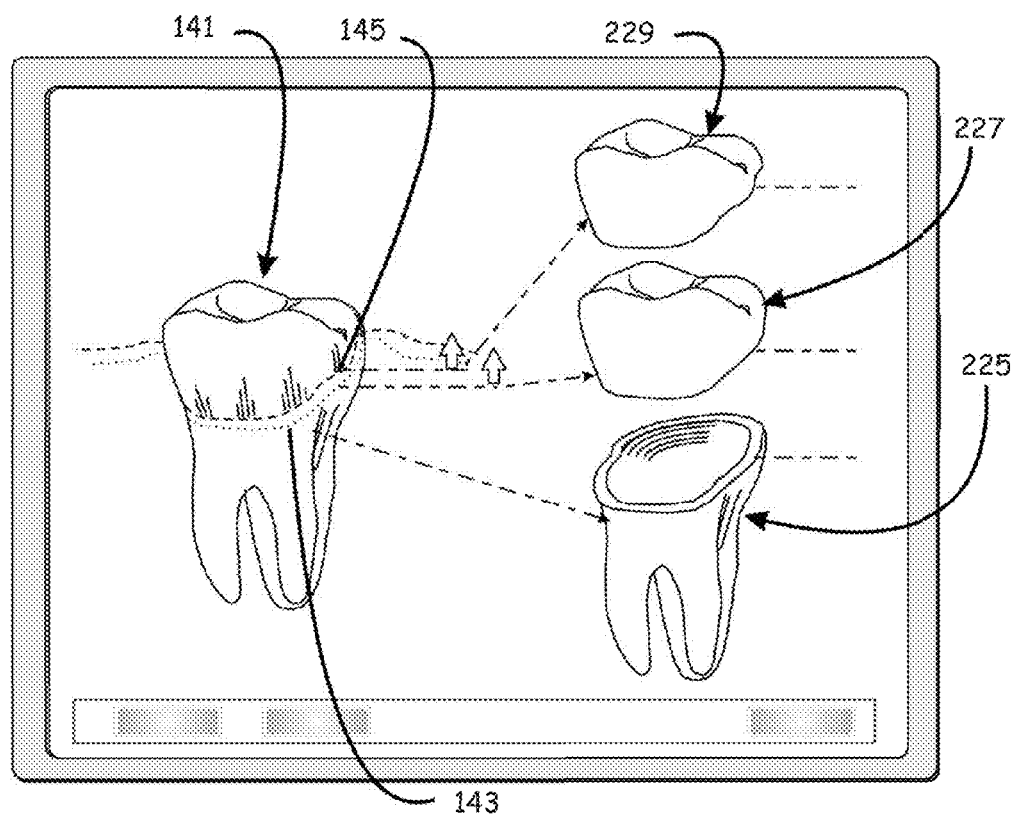
FIG. 33 illustrates the division or separation of parts of a virtual model.

As shown in FIGS. 34, and 36-38, the steps can also include forming a virtual occlusally-facing dental prosthesis component modeling an occlusally-facing dental prosthesis component, such as, for example, a virtual crown component 237 (FIG. 38) and/or a virtual transgingival cap component 239 (FIG. 38). The virtual crown component 237 can be formed by employing the procedures described with respect to forming the virtual crown component in the two-piece configuration, to include copying at least portions of the modeled virtual crown portion 229 to form a base shape of a complementing interface surface 241 (FIG. 37) of the virtual crown portion, reducing dimensions the modeled second virtual crown portion 229 to at least support minimal material thickness requirements of between approximately 0.2 mm to 0.5 mm (typically 0.3 mm) to form the complementing interface surface model shown at 243 (FIGS. 34 and 37, and as shown in FIG. 37, combining the virtual crown portion model 229 with the complementing interface surface model 243 to form the virtual crown portion 237 (FIG. 38). Note, the virtual crown component 237 (FIG. 38) extends in the apical direction to, for example, the virtual outer gum line representation 145 (FIG. 33). Note also, the aforementioned step of combining virtual crown portion 229 with the complementing virtual interface surface model 243 includes a design step to close potential gaps between the two outward-facing interface shells that form substantially the virtual crown component 237 (FIG. 38).

As shown in FIGS. 34 and 36, the transgingival cap can be formed using a similar set of procedures. For example, the step of forming the virtual transgingival cap component 239 (FIG. 38) can include forming a complementing virtual dental implant body receiving (interface) surface 245 (FIG. 36) modeling a complementing interface surface to receive occlusally-facing portions of the dental implant body, and forming a complementing virtual dental crown body receiving (interface) surface 247 (FIG. 36) modeling a complementing interface surface to receive apically-facing portions of the dental crown body. This can be accomplished by: copying at least portions of the first modeled virtual crown portion 227 (modeling the transgingival cap portion cut along the bone-facing gum line representation 143) and reducing dimensions of the at least portions of the modeled first virtual crown portion 227 to define an interface model 249 to form a base shape of the complementing interface surface 245 to thereby form the occlusally-facing surface of the virtual transgingival cap portion 239; reducing dimensions of the at least portions of the first modeled virtual crown portion 227 modeling the transgingival cap portion shown at 247 by reducing dimensions of the at least portions of the first modeled virtual crown portion 227; and combining the virtual transgingival cap model 247 with the complementing interface surface model 249 to form the virtual transgingival cap 239 (FIG. 38). Note, the virtual transgingival cap 239 (FIG. 38) extends in the apical direction to, for example, the bone-facing gum line representation 143 (FIG. 33). Note, the aforementioned steps of reducing the virtual transgingival cap model 247 and reducing the complementing virtual interface surface model 249 are coordinated to the extent to account for a minimal material thickness of approximately between 0.2 mm to 0.5 mm (typically 0.3 mm). Also, the aforementioned step of combining the virtual transgingival cap model 247 with the complementing virtual interface surface model 249 includes a design step to close potential gaps between the two outward-facing interface shells that form substantially the virtual transgingival cap 239 (FIG. 38).

Note, the dimensions of the transgingival cap portion model 247 is reduced to be smaller than the dimensions of complementing interface surface model 243, and the dimensions of virtual prosthesis interface model 235 is reduced to be smaller than the dimensions of the complementing interface surface model 249. These dimensional reductions in the three-dimensional size of the pairs of surfaces that build an interface and/or form the form-locking fit are to account for manufacturing tolerances and to account for a certain thickness of the layer of adhesive, cement or glass solder, etc., generally in the range of 50 to 300 micrometers, but preferably approximately 100 micrometers.

Interlocking Compound Dental Implant/Prosthesis

Figure 40:
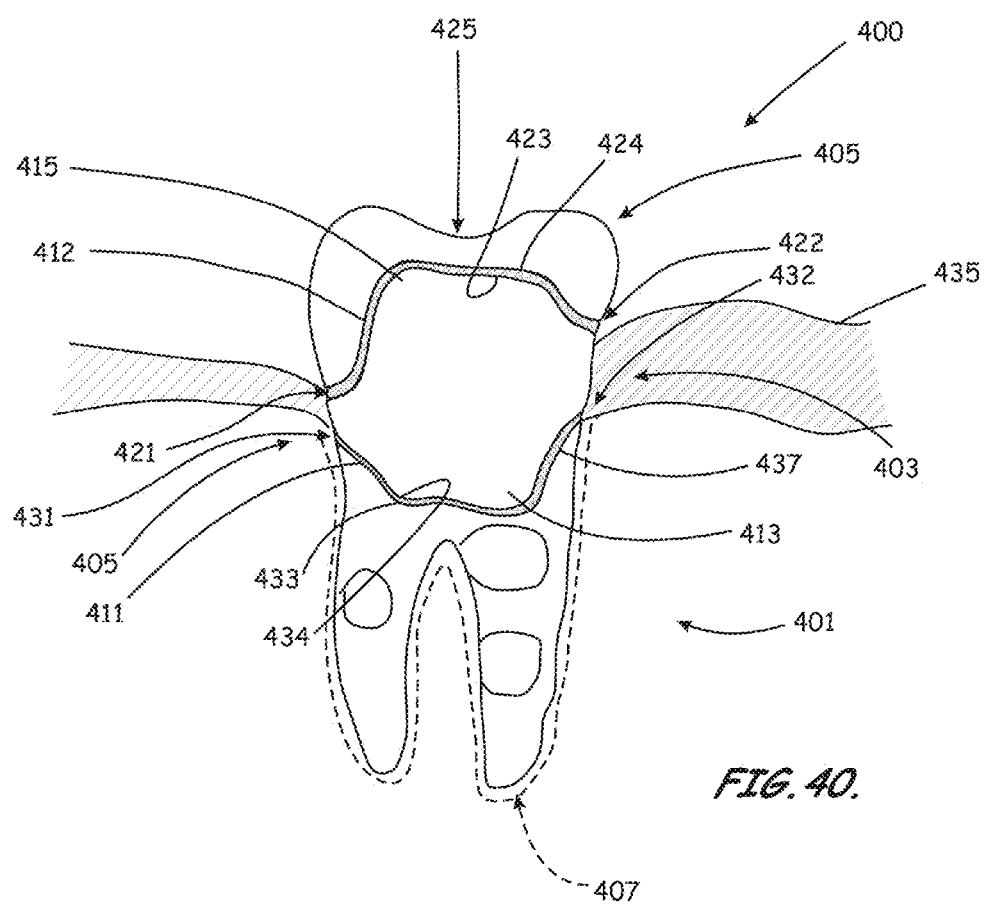
FIG. 40 is a partially cross-sectional view of an exemplary compound one-piece prosthesis showing a first joint between an implant body and a transgingival interlock abutment and a second joint between the transgingival interlock abutment and a dental prosthesis component or crown according to an embodiment of the present invention.
Figure 41:
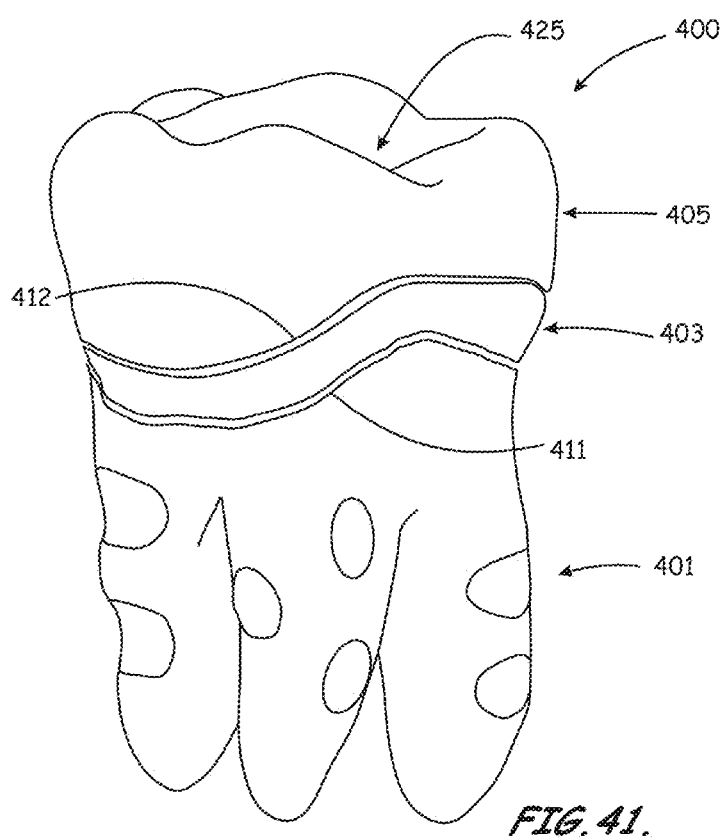
FIG. 41 is a perspective view of the exemplary compound one-piece prosthesis of FIG. 40 according to an embodiment of the present invention.

Various embodiments of the present invention include a single tooth prosthesis 400, shown in partially cross-sectional view in FIG. 40, and in perspective view in FIG. 41, which is a variant of the embodiment of the dental prosthesis shown and described in context of FIGS. 19, 21 and 28. According to the exemplary configuration, prosthesis 400 includes an implant body 401 (see also FIG. 42), a transgingival interlock abutment 403 (see also FIG. 43), and a occlusal-facing prosthesis component—e.g., a crown 405 (temporary and/or permanent) and/or an integrated support device (described later) or other dental prosthesis component. In the illustrated embodiment, the at least partially root-shaped implant body 401 at least substantially matches the extraction/implantation socket 407 of the jawbone of a pre-identified patient, generally without interfering with, or intruding into, the surface of the socket itself.

According to the exemplary embodiment, the implant body 401 is formed of, for example, commercially pure titanium (e.g., medical grade 2 commercially pure titanium) or a medical-grade titanium alloy (e.g., $Ti_6Al_4V$). According to the exemplary configuration, the middle piece, the transgingival interlock abutment 403, shown in perspective view in FIG. 41, is made, for example, of ceramic material e.g., yttria stabilized polycrystalline tetragonal zirconia (Y—TZP $ZrO_2$) or ATZ zirconia. In an exemplary embodiment, the transgingival interlock abutment 403 is favorably tooth colored, e.g., in its white body state, prior to final sintering by volumetric coloring (e.g., color liquid e.g., Zirkon B4; C3; D4, Zirkonzahn). The crown 405 can also be ceramic and/or ceramic having a layer simulating enamel as known to those of ordinary skill in the art. Other crown materials discussed above can be used alternatively.

According to the embodiment illustrated in FIGS. 40 and 41, the prosthesis 400 has two fully custom-shaped joints or interfaces 411 and 412. A first joint 411 located between the implant body 401 and the apical extending rising 413 of the transgingival interlock abutment 403 is generally positioned sub-gingivally, e.g., at the bone crest level, and the second joint 412 located between the occlusal extending rising 415 of the transgingival interlock abutment 403 and the crown 405 is generally positioned iso- or supra-gingivally, or adjacent to the outer gingival line at 421 and at 422, when the prosthesis 400 is operably positioned within the jawbone of the pre-identify patient. An advantage of such exemplary design or designs includes providing a ceramic abutment that is no longer a fragile, but rather, a massive solid. Additionally, an advantage includes an elimination of the risk that gray metal (titanium) shines through what would be a relatively thin crown portion.

The figure details an example of the contour lines of the apical and occlusal joints 411, 412, as presented in a cross-sectional view of the prosthesis 400. According to the illustrated embodiment, the cross-section of the occlusal joint 412 shows a rounded run-out 421, 422, at the perimeter of the joint facing bonding surfaces 423, 424, where the local cross-sections of the opposing parts perpendicular to the perimeter line have a stable material edge of approximately 90 degrees. The cross-section of the apical joint 411 shows an angled run-out 431, 432, at the perimeter of the joint facing bonding surfaces 433, 434, where the local cross-sections of the opposing parts perpendicular to the perimeter line have a stable not-sharp material edge of the ceramic part of more than 90 degrees, while the corresponding titanium implant body part has a sharp edge of less than 90 degrees—preferably 135 degrees for the ceramic part and 45 degrees for the titanium part. This can beneficially provide utmost fracture toughness for the ceramic part, while the titanium material is not undermined by the sharp run-out.

Further beneficially, each pair of surfaces that build the two prosthetic interfaces 423, 424 and 433, 434, each create a form locking fit. The respective three-dimensional surfaces 423, 424 (shown as cross-sectional view) dimensionally correlate with the outer three-dimensional shape of the crown 405 and dimensionally correlate with each other. The respective three-dimensional surfaces 433, 434 (shown as cross-sectional view) dimensionally correlate somewhat with the outer three-dimensional shape of the implant body 401 and dimensionally correlate with each other. According to the illustrated embodiment, the three-dimensional surface shape of the occlusal extending rising 415 includes a substantial asymmetric negative indent 425 recessed into the occlusal facing surface of the occlusal extending rising 415.

According to the exemplary configuration, the design of the shapes of both joints is created or originated in the virtual domain using the digital data representing the anatomical specifics of interest. In the exemplary configuration, the outer joint line of the interface between the implant body 401 and the transgingival interlock abutment 403 (shown in the cross-sectional view as edges at 431, 432) follows the saddle shaped 3D curvature of the bone crest adjacent the anatomical socket, while the outer joint line of the interface between the transgingival interlock abutment 403 and the crown 405 (shown in the cross-sectional view as edges a 421, 422) follows the saddle shaped 3D curvature adjacent the gum line of the gingiva 435.

Again, this is not a standard curvature of a cylindrical mass-produced implant. To the contrary, this design is individually performed per specific tooth of a pre-identified patient. The shape data are derived from clinical images of the dental anatomy of such patient. In this specific context, the design takes into account the anatomical cross-section of the implant body 401 to at least substantially match the shape of the extraction/implantation socket 407, or at least substantially match the root of the tooth being extracted, and have its upper rim 437 (see FIG. 42) substantially match the 3D curvatures of the bone crest, and its orientation match the orientation of the original tooth (not shown) and/or as desired to correct errors in the orientation of the original tooth.

Figure 42:
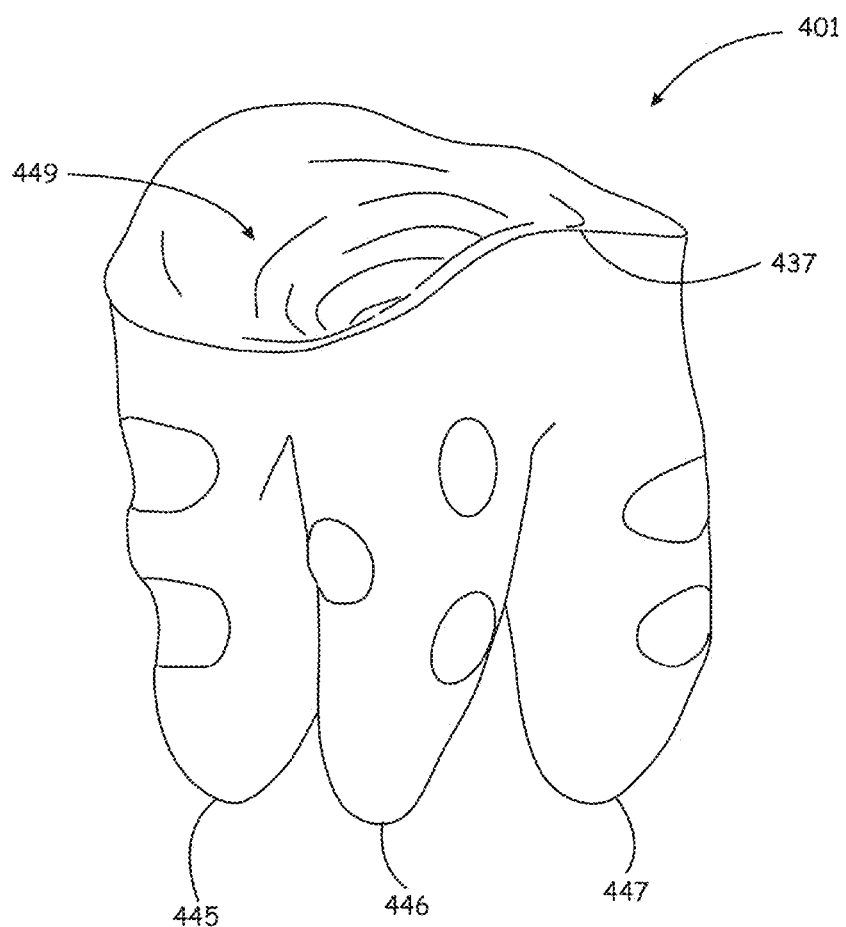
FIG. 42 is a perspective view of an implant body according to an embodiment of the present invention.
Figure 43:
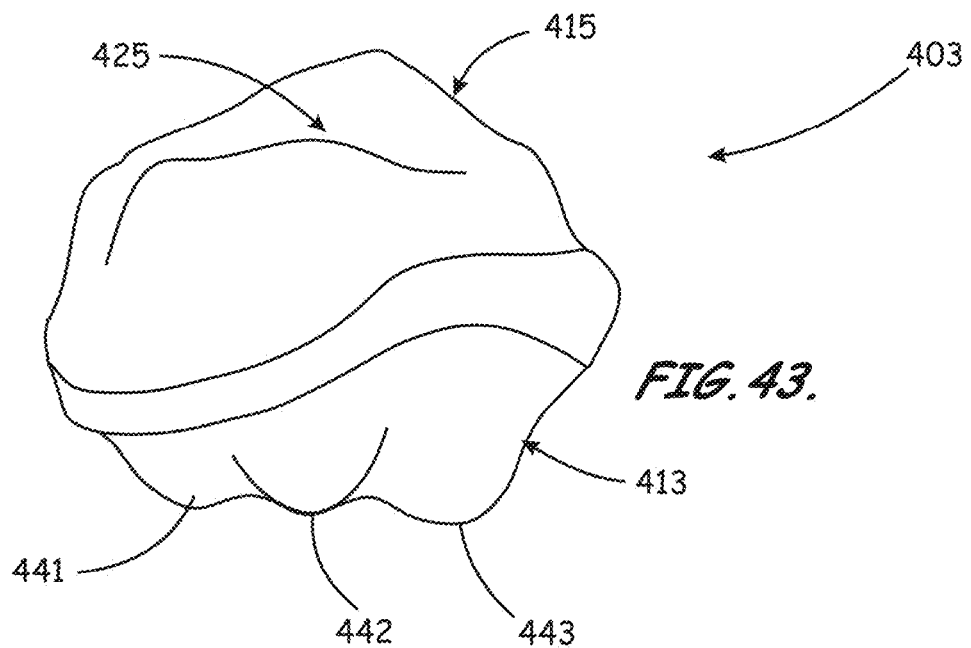
FIG. 43 is a perspective view of a transgingival interlock abutment according to an embodiment of the present invention.
Figure 44:
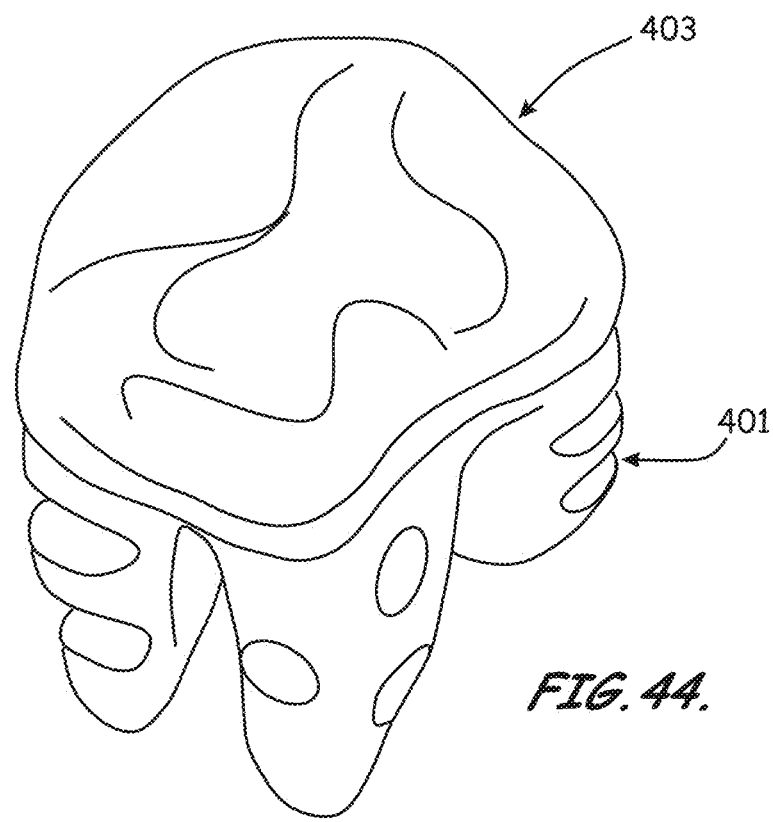
FIG. 44 is a perspective view illustrating the transgingival interlock abutment shown in FIG. 43 landed within the implant body shown in FIG. 42 according to an embodiment of the present invention.

As perhaps best shown in FIG. 43, the apical extending rising 413 of the transgingival interlock abutment 403 can have projections 441-443, that tend to follow the structure of the root projections 445-447 (FIG. 42), respectively. The shape of the joint 411 can be determined using various mathematical expressions known to those of ordinary skill in the art such as, for example, a three-dimensional moving average of points along the outer surface of the root structure of the implant 401. The substantially parallel gap between the two adjacent surfaces 433, 434, that build the joints 411, 412, is, in the illustrated configuration, about 150 micrometers to accommodate a minimal thickness of the glass solder for the sub-gingival joint 411 and for the cement for the iso- or supra-gingival joint. The apical joint 411 is assembled and temporarily fixated by resin or cement based adhesives or a combination thereof, having a thickness (coatings plus adhesives) between 50 and 250, preferably of 150 micrometers. FIG. 44 illustrates the transgingival interlock abutment 403 landed within a recess 449 (see FIG. 42) having an inner surface shape which complements the apical extending rising 413 extending therein.

In preparation of the assembly of the apical joint, the joint facing surfaces of the zirconia part and of the titan part (medical grade titanium alloy or medical grade commercially pure titanium) are each furnace-fired with a silicatised coating. The parts are fused with a glass-soldering material at about between 750 and 850 degrees Celsius scale, preferably at 800. The furnace-fired joint materials having a cumulated thickness (coatings plus solder) between 50 and 250, preferably of 150 micrometers; while the silicate coating shows an approx. thickness of 50 micrometers per surface.

The joint/interface between the transgingival interlock abutment 403 and the crown 405 was discussed previously in the context of FIG. 19. In preparation of the assembly of the occlusal joint 412, according to the exemplary embodiment, the joint facing surfaces of the zirconia parts, are furnace-fired with a silicatised coating that is roughened by sandblasting and/or acid etching, using a silan-coupling agent as a primer. The thicknesses of the coatings cumulate to an approx. thickness of 50 micrometers per surface.

FIG. 45 shows an exploded view of the dental prosthesis 400 shown in FIG. 41. FIG. 46 shows an exploded view of a dental prosthesis 400' having an implant body 401, a transgingival interlock abutment 403, and in place of the crown 405, an integrated support device (described later) for providing primary stability to implant body-abutment assembly or a version of the dental prosthesis 400 employing a temporary crown 405' having a reduced size to accommodate engagement with integrated support device.

Note, according to the illustrated configurations, each transversal and lateral cross-section of the components of the dental prosthesis 400, 400', are custom-shaped, having an individual three-dimensional shape that is substantial asymmetric, that does not include generic concentric shapes, that does not include generic symmetric shapes, and that does not include convolutional shapes. The respective form-locking fit of the prosthetic interfaces forming the joints 411, 412 are clearly indicated for understanding by those skilled in the art. The outer circumferential edges traveling with the contour of the joints 411, 412 varies in the direction of a longitudinally axis of the implant body 401 and in transversal direction with respect to the distance to such longitudinal axis. For those skilled in the art, it is clearly indicated that the three-dimensional shapes of the aforementioned interface surfaces correlate with the outer surface of the crown/root, respectively, and with each other. Further, in a tooth such as an incisor, for example, the maximal transversal dimension of the implant body 401 adjacent the outer circumferential edge 437 (see, e.g., FIG. 42) is significantly bigger than the minimal transversal dimension of the implant body 401 adjacent the outer circumferential edge 437 (FIG. 42 as well).

Designing the Interlocking Compound Dental Implant

FIGS. 47-56 illustrate an example of a method of designing the interlocking compound "one-piece" dental prosthesis 400 (shown in FIGS. 40 & 41) formed of "three" primary pieces, based upon the three-dimensional virtual model 451 of at least portions of the non-functional natural tooth (best shown in FIG. 1 on the left hand side). According to an example of the three-piece dental prosthesis configuration, as perhaps best shown in FIG. 47, the step of forming a virtual model of a dental prosthesis 453 (FIG. 56) includes separating a portion of the three-dimensional virtual model 451 along the virtual bone-facing gum line representation 457 to form a modeled virtual root portion 459, and separating the remaining portion of the model at the outer gum line 461 to form a virtual midline portion 463 of the virtual model of the transgingival interlock abutment of the virtual model of the dental prosthesis 453 (FIG. 56) and to form the virtual crown portion model 465 modeling the outer surface of the physical crown, e.g., crown 405 (best shown in FIG. 41) or an outer surface portion of the integrated support device (described later) 405' (FIG. 46).

Figure 47:
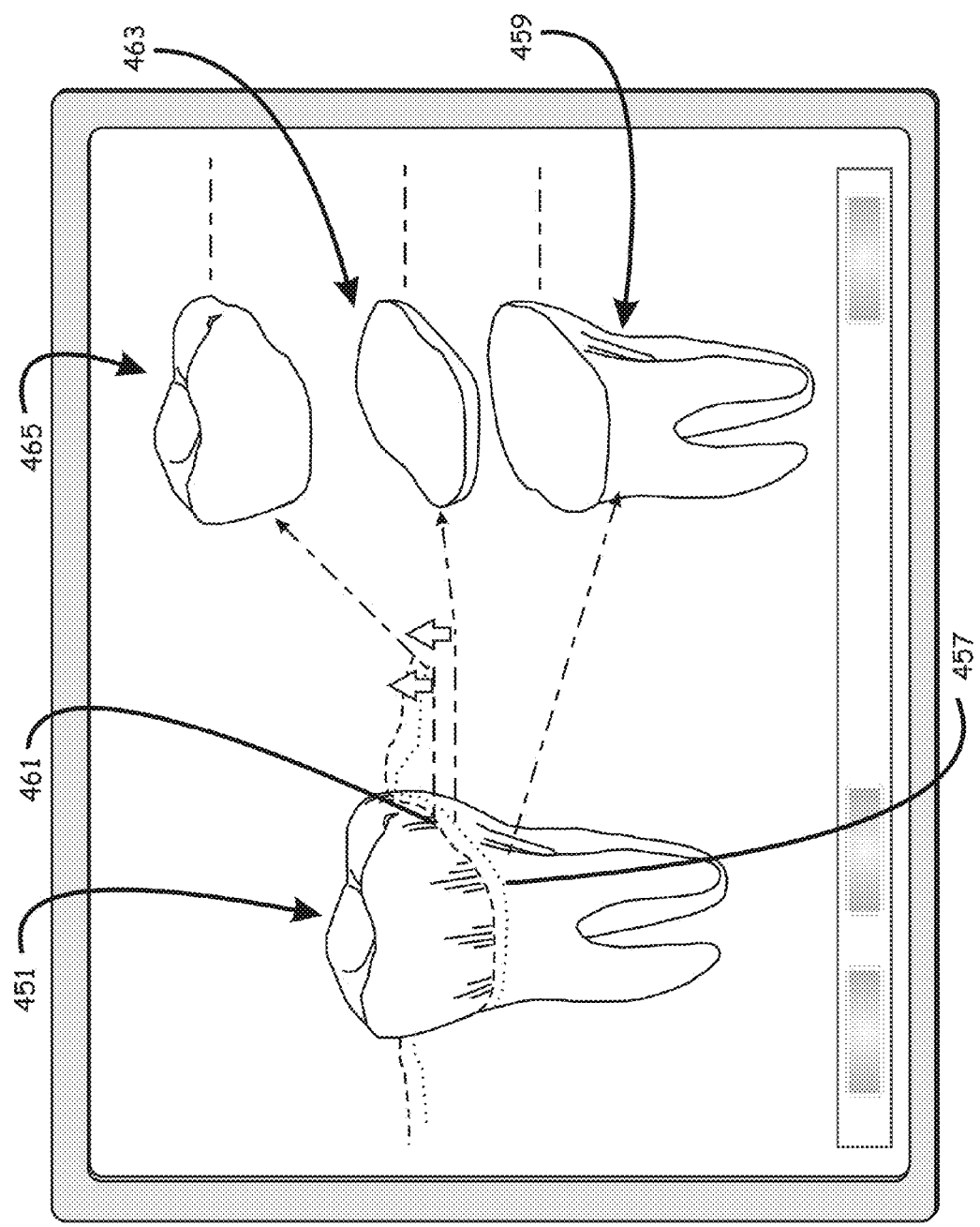
FIG. 47 is a part perspective view illustrating division of a virtual model into separate parts according to an embodiment of the present invention.
Figure 48:
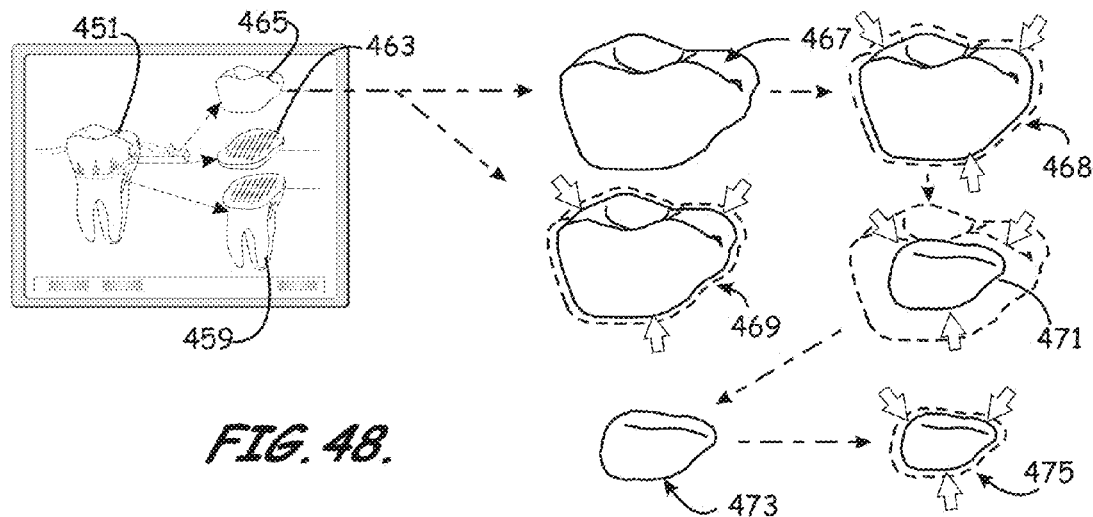
FIG. 48 is a sectional view illustrating copying and restructuring of parts of a virtual model according to an embodiment of the present invention.

According to the illustrated embodiment shown in FIG. 47, the modeled virtual crown portion 465 models a crown having a full-size shape. As perhaps best shown in FIG. 48, if it is desired to manufacture a temporary crown such as, for example, one having a slight infra-occlusion designed to avoid occlusal contacts with an opponent tooth during the healing phase, the step of forming the virtual dental prosthesis 453 can also include copying the modeled virtual crown portion 465 to form a virtual crown component 467 and reducing the dimensions of at least portions of the virtual crown component 467 to form the outer surface of the virtual temporary crown 468.

Figure 56:
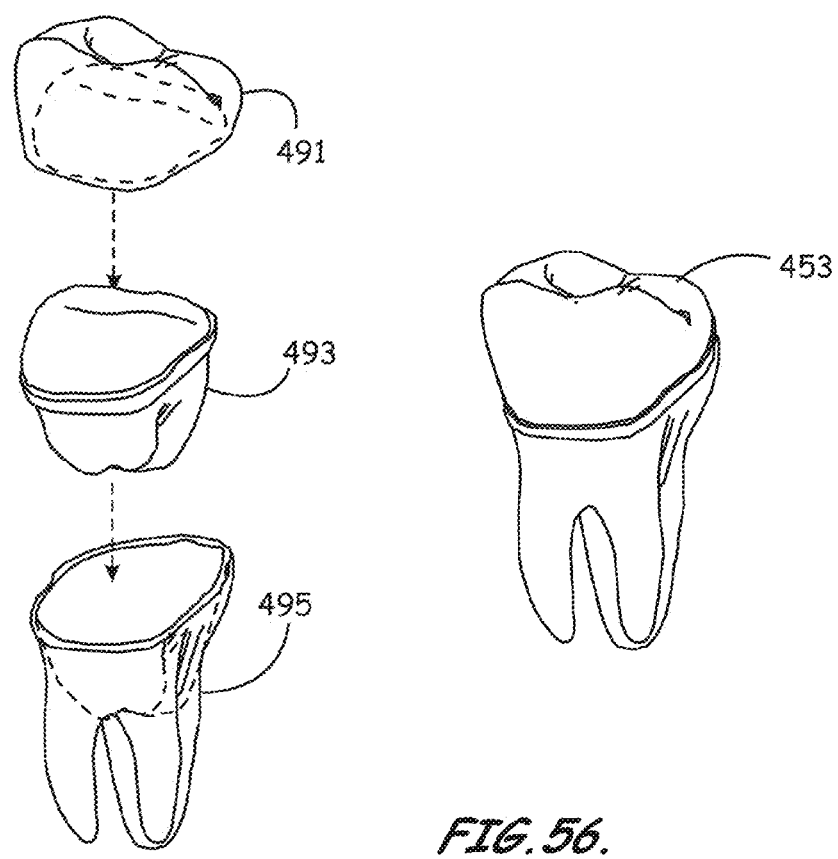
FIG. 56 is a sectional view illustrating the combining of virtual models to form a virtual dental prosthesis according to an embodiment of the present invention.

If the goal is to model a dental prosthesis having a reduced-size (e.g., temporary) crown, according to the exemplary embodiment, the step of forming the virtual dental prosthesis 453 (FIG. 56) also includes copying at least portions of the virtual occlusally facing crown component 467 (or virtual crown portion 465) to form a virtual occlusally facing crown component 469. The step also includes reducing the dimensions of at least portions of the modeled virtual occlusally facing crown component 469; and in the exemplary configuration which provides enhanced structural stability, smoothing/adjusting the contours to form a virtual occlusal extending rising interface 471. The step can also include copying the virtual occlusal extending rising interface 471 to form a virtual apical facing crown component 473 and reducing the dimensions to form a virtual occlusal extending rising 475 modeling the occlusal extending rising 415 (see, e.g., FIG. 43) of the virtual transgingival interlock abutment 493 (FIG. 56).

Figure 49:
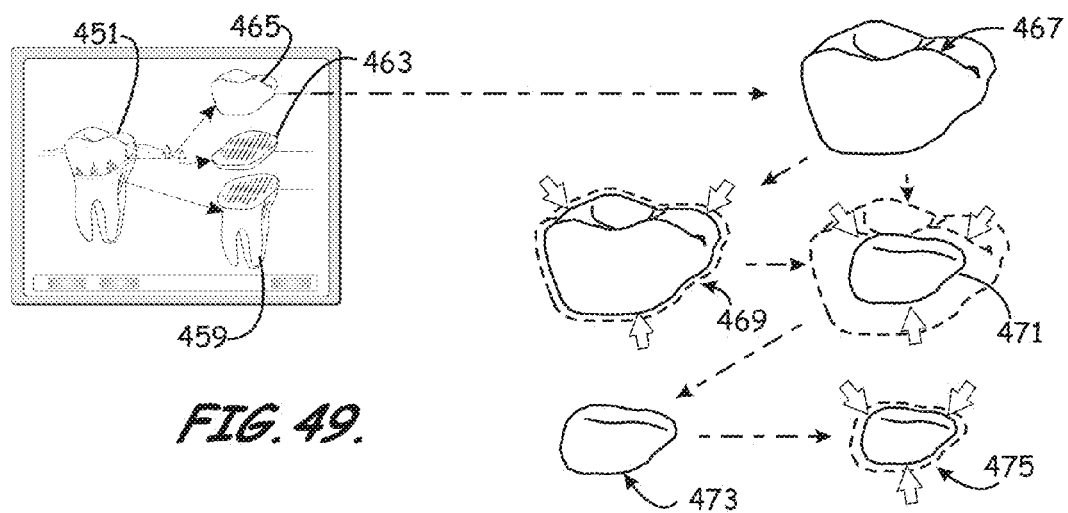
FIG. 49 is a sectional view illustrating copying and restructuring of parts of a virtual model according to an embodiment of the present invention.

If the goal is to model a dental prosthesis having full-size crown, as perhaps best shown in FIG. 49, according to the exemplary embodiment, the step of forming the virtual dental prosthesis 453 (FIG. 56) includes copying at least portions of the modeled virtual occlusally facing crown portion 465 to form the virtual occlusally facing crown component 467. Note, this embodiment, the virtual occlusally facing crown component 467 also models the physical crown surface. The step also includes copying at least portions of the modeled occlusally facing virtual crown portion 465 or virtual occlusally facing crown component 467 to form the virtual crown component 469. The step also includes reducing the dimensions of at least portions of the modeled virtual occlusally facing crown component 469; and in the exemplary configuration which provides enhanced structural stability, smoothing/adjusting the contours to form the virtual occlusal extending rising interface 471. The step also include copying the virtual occlusal extending rising interface 471 to form a virtual apical facing crown component 473 and reducing the dimensions to form the virtual occlusal extending rising 475 modeling the occlusal extending rising 415 (e.g., FIG. 43) of the virtual transgingival interlock abutment 493 (FIG. 56).

Figure 50:
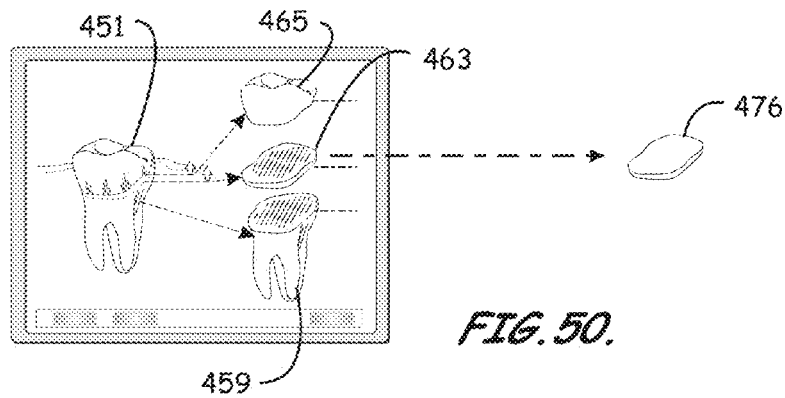
FIG. 50 is a sectional view illustrating copying of part of a virtual model according to an embodiment of the present invention.

As perhaps best shown in FIG. 50, the step of forming the virtual dental prosthesis 453 (FIG. 56) includes the step of copying at least portions of the virtual midline portion 463 to form a virtual midline component 476, alternatively, dragging the virtual midline portion 463 to be used in constructing the virtual dental prosthesis 453, as will be described later. Note, the virtual midline portion 463 is an outward facing shell, most typically having a non-flat occlusally facing extension at virtual outer gum line 461 and a non-flat apically facing extension at the virtual bone-facing gum line representation 457. Both typically follow an individual saddle contour line of the occlusally facing edge at least partially matching the contour of the outer virtual gum line, and the apical facing edge at least partially matching the contour of the virtual bone crest line adjacent the extraction socket.

According to the illustrated embodiment shown in FIG. 47, the modeled virtual root portion 459 models a root of an existing non-functional tooth of the specific patient. As perhaps best shown in FIG. 51, if it is desired to manufacture an implant body having a larger size, such as, for example, to enhance osseointegration, or a smaller size to provide for additional coating layers or to enhance perio-type integration, the step of forming the virtual dental prosthesis 453 (FIG. 56) can also include copying the modeled virtual root portion 459 to form a virtual root component 477 and either reducing or enlarging the dimensions of at least portions of the virtual root component 477, as desired, to form an outer surface of a virtual implant body 478.

Figure 51:
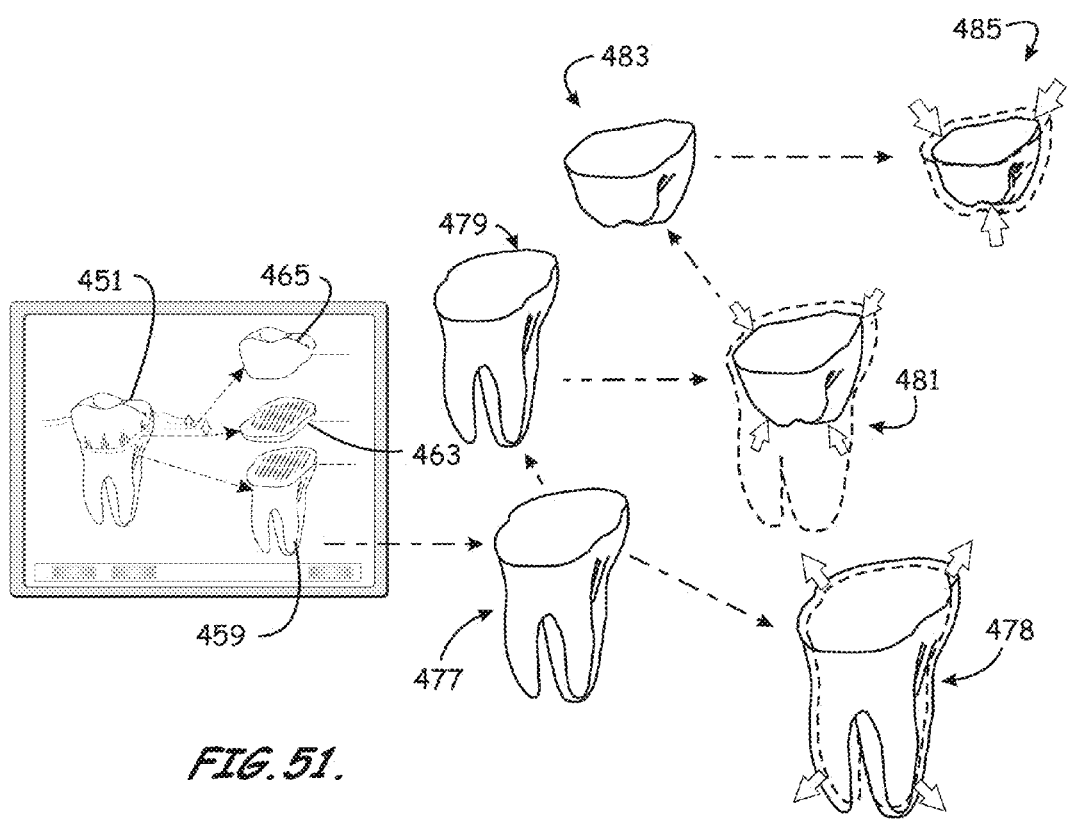
FIG. 51 is a sectional view illustrating copying and restructuring of parts of a virtual model according to an embodiment of the present invention.

If the goal is to model a dental prosthesis having an implant body having a larger or smaller root design, according to the exemplary embodiment shown in FIG. 51, the step of forming the virtual dental prosthesis 453 (FIG. 56) includes the steps of copying at least portions of the virtual root component 477 (or virtual root portion 459) to form virtual root component 479. The step also includes reducing the dimensions of at least portions of the modeled virtual root component 479; and in the exemplary configuration which provides enhanced structural stability, smoothing the contours to form the virtual apical extending rising interface 481. The step can also include copying the virtual apical extending rising interface 481 to form a virtual occlusally facing root component 483 and reducing the dimensions to form the virtual apical extending rising 485 modeling the apical extending rising 413 (see, e.g., FIG. 43) of the virtual transgingival interlock abutment 493 (FIG. 56).

Figure 52:
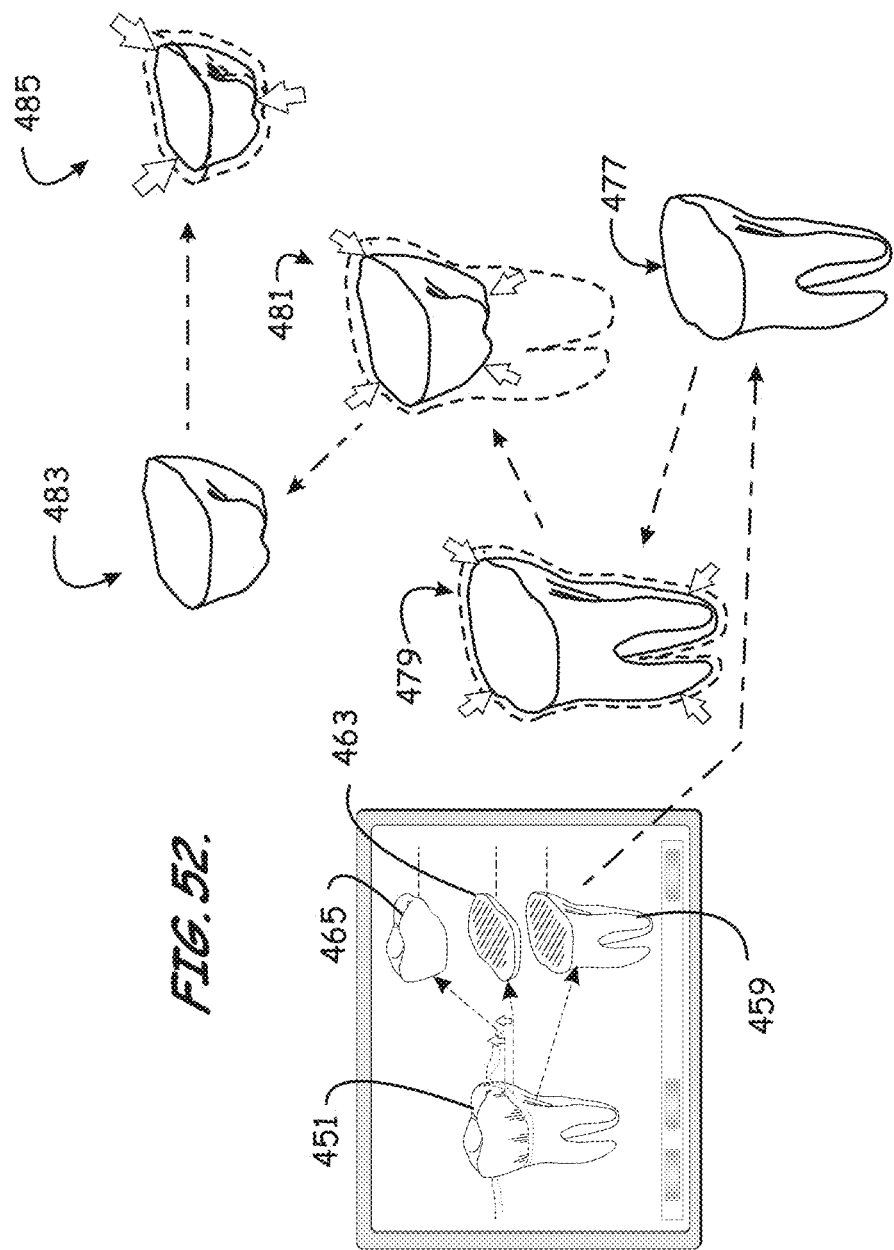
FIG. 52 is a sectional view illustrating copying and restructuring of parts of a virtual model according to an embodiment of the present invention.

If the goal is to model a dental prosthesis having an implant body having a substantially matching root design, as perhaps best shown in FIG. 52, the step of forming the virtual dental prosthesis 453 (FIG. 56) includes the steps of copying at least portions of the modeled virtual root portion 459 to form the virtual root component 477. Note, this embodiment, the virtual root component 477 also models the physical root surface. The step also includes copying at least portions of the virtual root component 477 (or virtual root portion 459) to form a virtual root component 479. The step further includes reducing the dimensions of at least portions of the modeled virtual root component 479; and in the exemplary configuration which provides enhanced structural stability, smoothing the contours to form a virtual apical extending rising interface 481. The step also includes copying the virtual apical extending rising interface 481 to form a virtual occlusally facing root component 483 and reducing the dimensions to form a modeled virtual apical extending rising 485 modeling the apical extending rising 413 (see, e.g., FIG. 43) of the virtual transgingival interlock abutment 493 (FIG. 56).

Note, although the illustrations describe a root portion matching the root of a non-functional tooth, one of ordinary skill in the art would recognize that the modeled virtual root portion 459 can instead represent an alternative portion of the dental anatomy including the shape of the cavity to receive the physical implant body 401 of the dental prosthesis 400 (see, e.g., FIG. 41).

Figure 53:
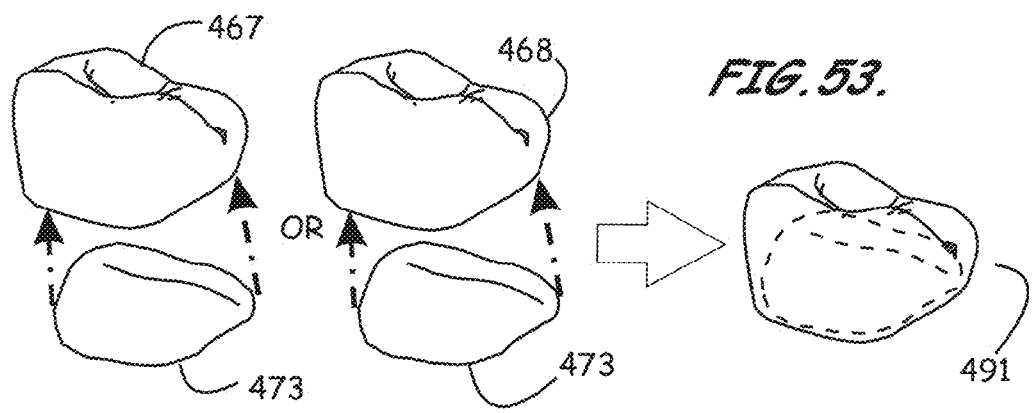
FIG. 53 is a sectional view illustrating the combining of virtual models to form a virtual crown portion according to an embodiment of the present invention.

As shown in FIG. 53, the step also includes combining the modeled virtual crown component 467 or modeled virtual crown portion 465 (see, e.g., FIG. 47, for same-size modeling) or virtual crown component 468 (e.g., for reduced/enlarged size modeling) with the virtual apical facing crown component 473 to form a virtual crown model 491 of the virtual dental prosthesis model 453 (FIG. 56), e.g., modeling a physical crown 405 (see FIGS. 40-41). Note, the aforementioned reductions to derive the virtual occlusally facing crown component and the virtual apical facing crown component should be/need to be coordinated to guarantee a minimal numerical and subsequently minimal physical thickness of between approximately 0.3 mm to 0.7 mm (typically 0.4 mm) of the physical crown cap 405 (best shown in FIG. 45) for stability reasons.

Figure 54:
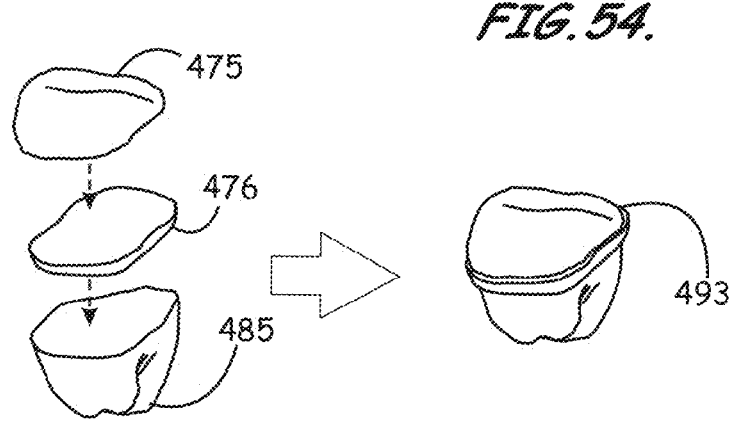
FIG. 54 is a sectional view illustrating the combining of virtual models to form a virtual trans-gingival interlock abutment portion according to an embodiment of the present invention.

As shown in FIG. 54, the step also includes combining the virtual occlusal extending rising 475, the virtual midline component 476 (or virtual midline portion 463), and the virtual apical extending rising 485 to form a transgingival interlock abutment model 493 of the virtual dental prosthesis model 453 (FIG. 56), e.g., modeling a physical abutment 403 (see FIGS. 40-41 and 43).

Figure 55:
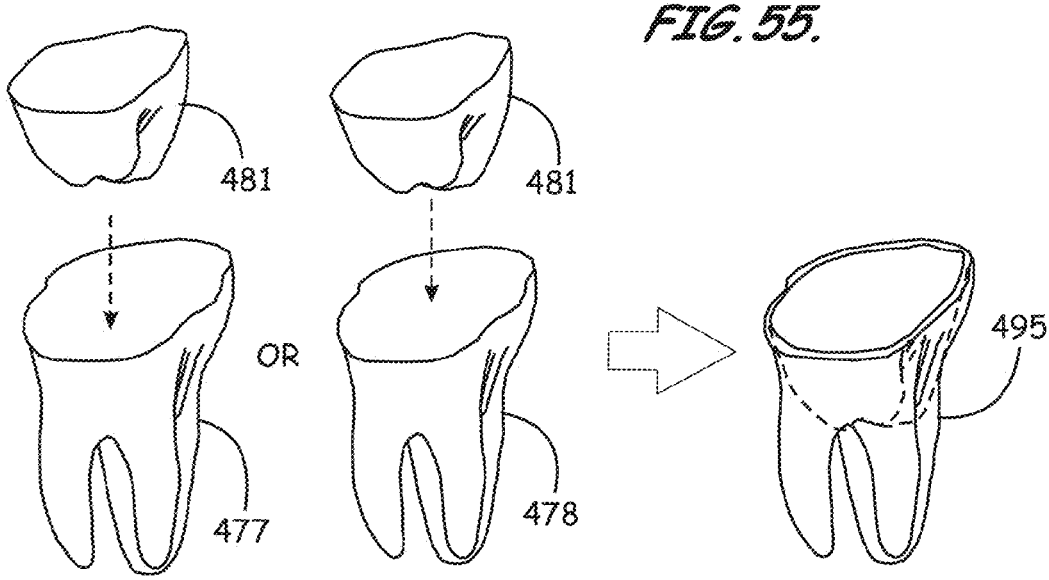
FIG. 55 is a sectional view illustrating the combining of virtual models to form a virtual dental implant body portion according to an embodiment of the present invention.

As shown in FIG. 55, the step also includes combining the virtual root component 477 or modeled virtual root portion 459 (see, e.g., FIG. 47, for same-size modeling) or virtual root (apical facing) component 478 (e.g., for reduced/enlarged size modeling) with the virtual occlusally facing root component 483 to form a virtual root component model 495 of the virtual dental prosthesis model 453 (FIG. 56), e.g., modeling a physical implant body 401 (see FIGS. 40-41 and 42). Note, the aforementioned reductions to derive the virtual occlusally facing root component and the virtual root component apical facing root component should be/need to be coordinated to guarantee a minimal numerical and subsequently a minimal physical thickness of between approximately 0.2 mm to 0.7 mm (typically 0.3 mm) of the physical implant body (best shown in FIG. 42) for stability reasons.

As shown in FIG. 56, the step also includes combining the virtual crown model 491, the transgingival interlock abutment model 493, and the root component model 495 to form the virtual dental prosthesis model 453, e.g., modeling a physical dental prosthesis 400 (see FIGS. 40, 41 and 45) or a physical dental prosthesis 400' (see FIG. 46).

Note, the dimensions of the virtual occlusal extending rising 475 is reduced to be smaller than the dimensions of the virtual apical facing crown component 473, and the dimensions of the virtual apical extending rising 485 is reduced to be smaller than the dimensions of the virtual occlusally facing root component 483. These dimensional reductions in the three-dimensional size of the pairs of surfaces that build an interface and/or form the form-locking fit are to account for manufacturing tolerances and to account for a certain thickness of the layer of adhesive, cement or glass solder, etc., generally in the range of 50 to 300 micrometers, but preferably approximately 100 micrometers. Further, the smoothing can be performed using various mathematical functions known to those of ordinary skill in the art to enhance structural stability at the component interfaces. Note, that all combinations of surface shells mentioned in the preceding paragraphs can include a design step of closing potential gaps while patching the surface components known to those of ordinary skill in the art to build numerically tight 3D surface objects used for further CAD/CAM processing.

Integrated Support Device

Component Description of the Integrated Support Device

According to various embodiments of the present invention, primary stability is favorably achieved by a custom made integrated support device that connects parts of a dental prosthesis with an adjacent tooth or teeth or other dental structures like existing implants, bridges and the like. The concept of a support device that is custom made in the laboratory in advance serves two purposes, the correct positioning of the prosthesis and the achievement of reasonable primary stability. After the dental implant is healed in, the integrated support device is to be clinically detached from the implants body (that may include an abutment portion) so that the implant body can receive a definite crown. In an embodiment of this invention, the definite crown is manufactured prior to the detachment of integrated support device, based on the design data of the dental prosthesis according to the exemplary embodiment of the present invention.

Figure 57:
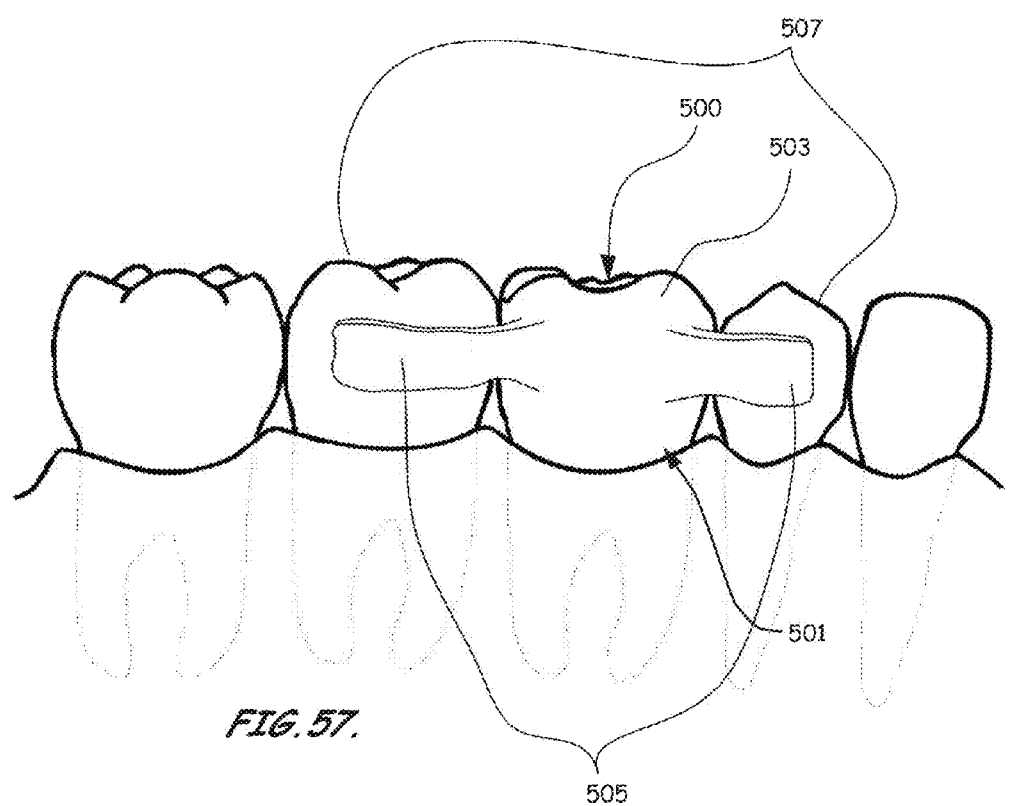
FIG. 57 is an environmental view illustrating a prosthesis with a crown portion body forming one part with bonding wings according to an embodiment of the present invention.

In an exemplary embodiment of the present invention, a dental prosthesis 500 is provided as depicted in FIG. 57. In the shown embodiment, and integrated support device 501 including a temporary crown portion body 503 and bonding wings 505 form one part, i.e., the crown portion body 503 entails wings 505 that attach to the adjacent teeth 507.

Figure 58:
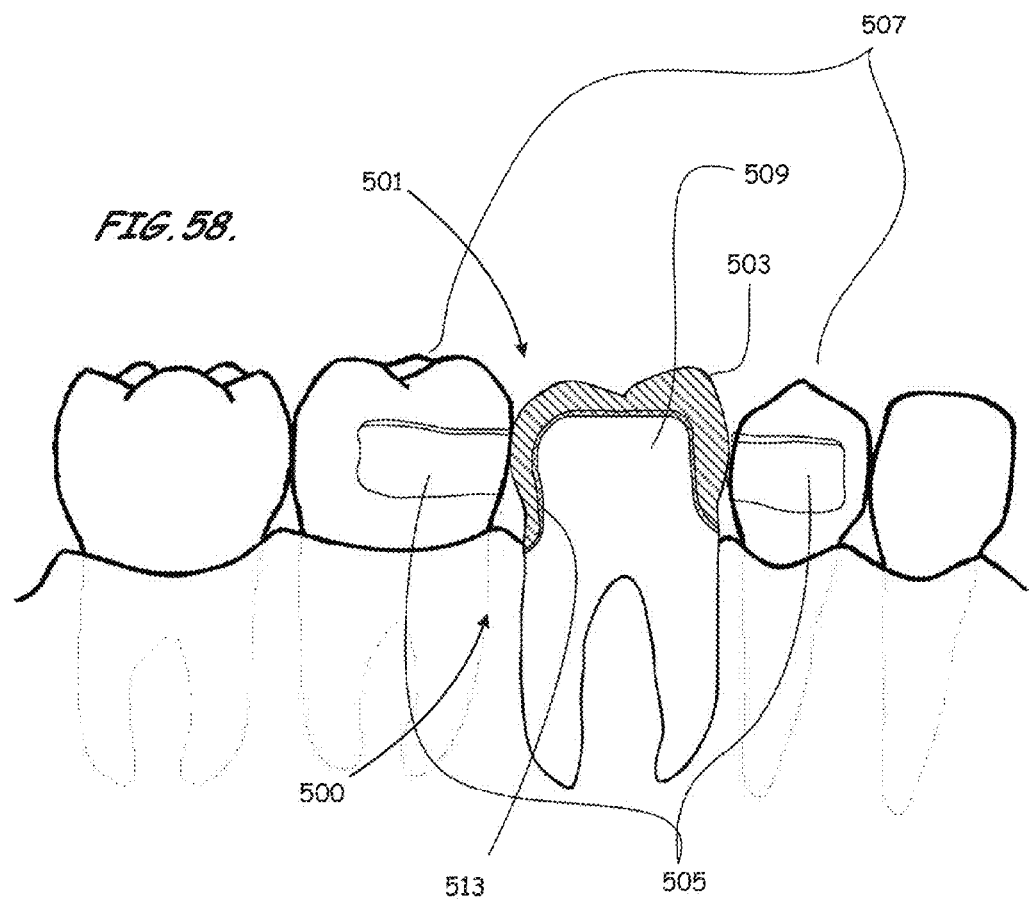
FIG. 58 is a sectional (cut away) view of the prosthesis with a crown portion body forming one part with the bonding wings illustrated in FIG. 57 according to an embodiment of the present invention.
Figure 61:
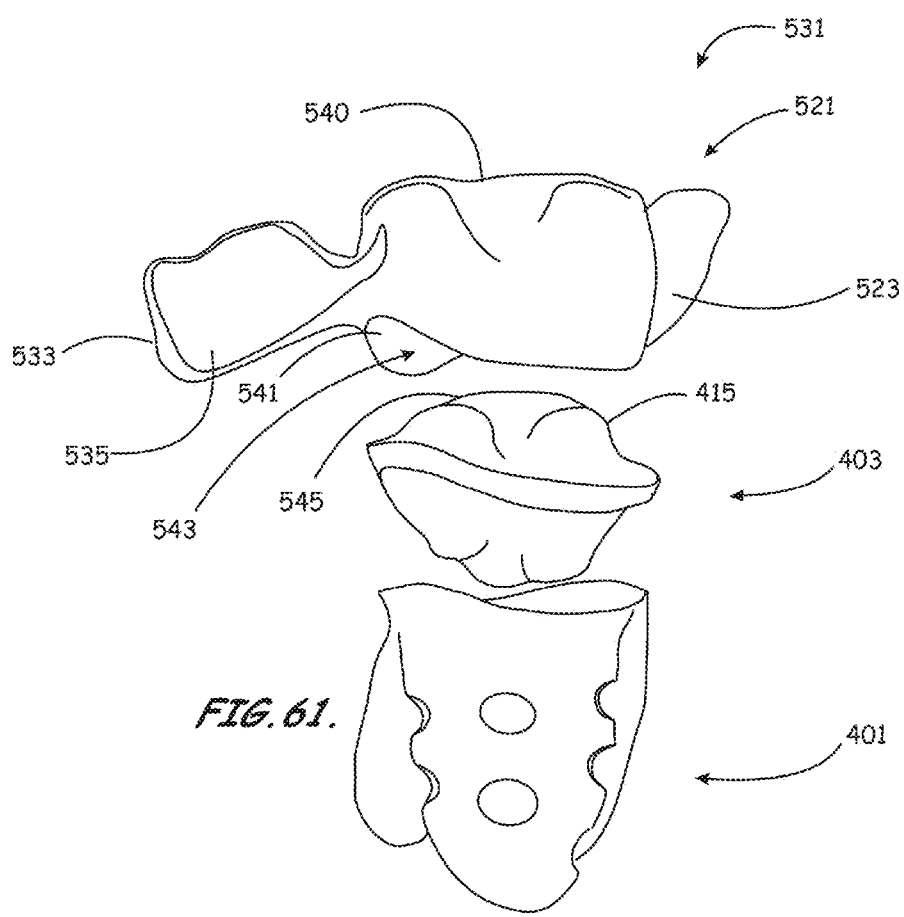
FIG. 61 is an exploded view of the integrated support device shown in FIG. 59 connected to portions of the exemplary prosthesis shown in FIG. 44 according to an embodiment of the present invention.
Figure 62:
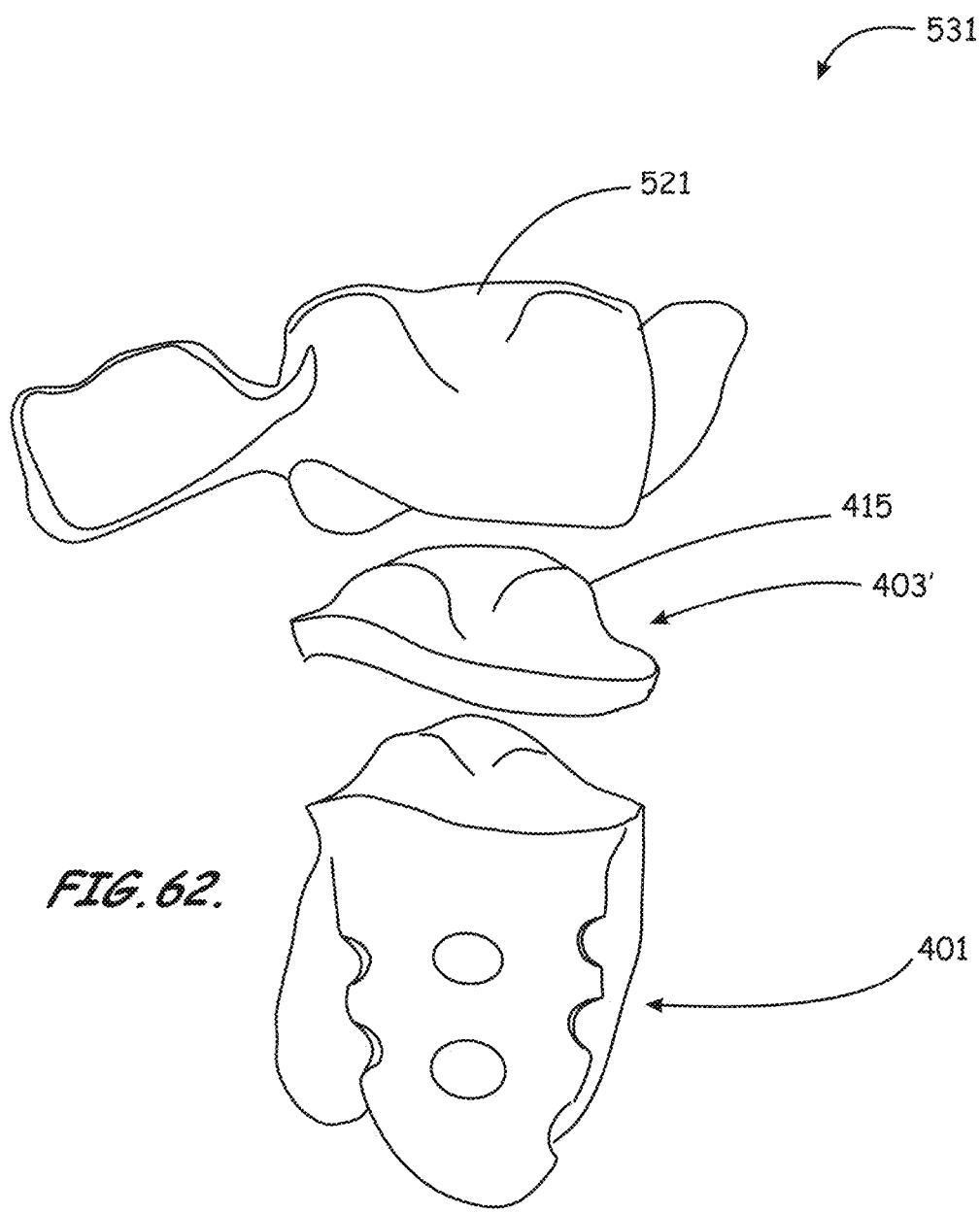
FIG. 62 is an exploded view of the integrated support device shown in FIG. 59 connected to portions of an exemplary prosthesis according to an embodiment of the present invention.
Figure 63:
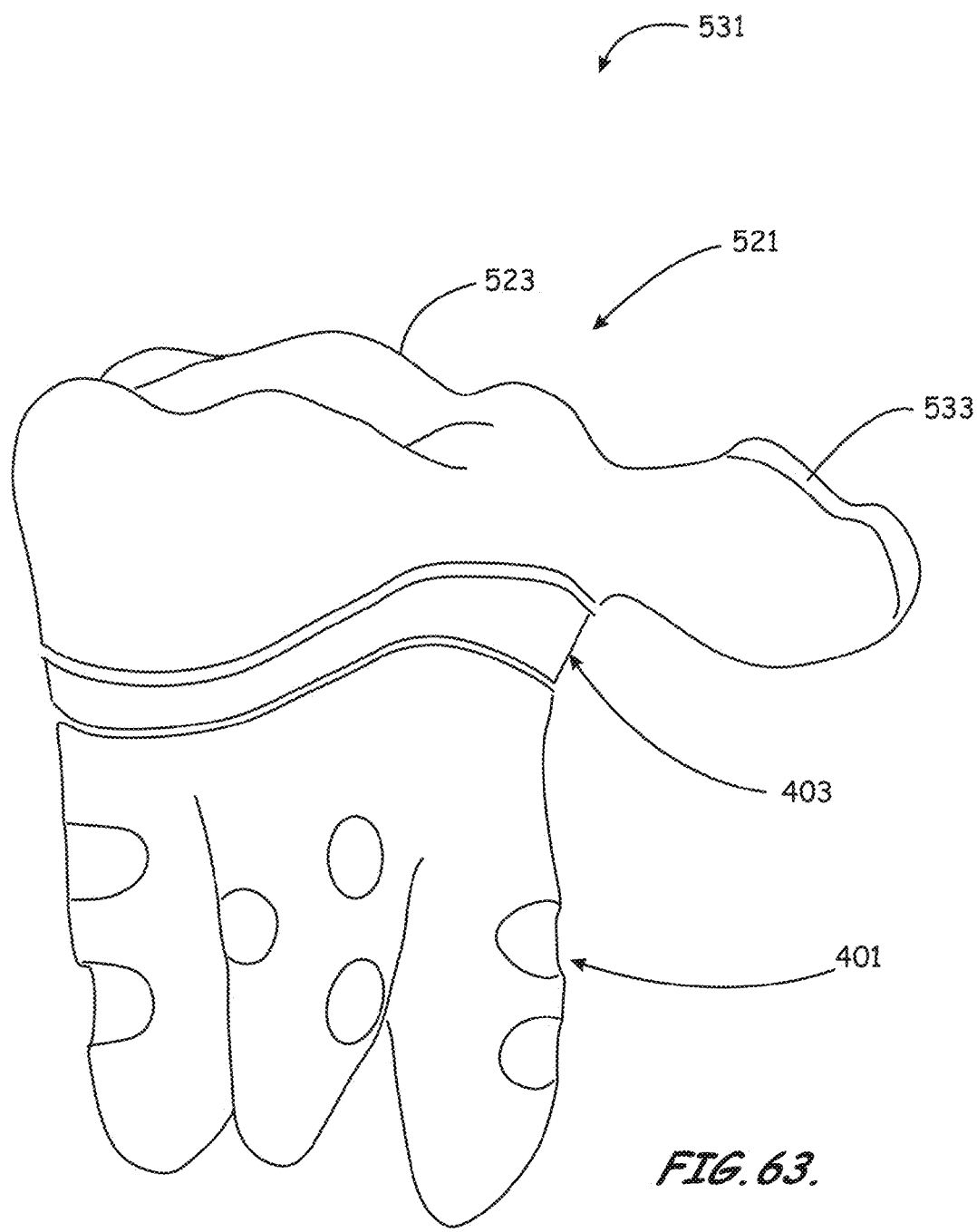
FIG. 63 is a perspective view of the integrated support device shown in FIG. 59 connected to portions of the exemplary prosthesis shown in FIG. 44 according to an embodiment of the present invention.
Figure 64:
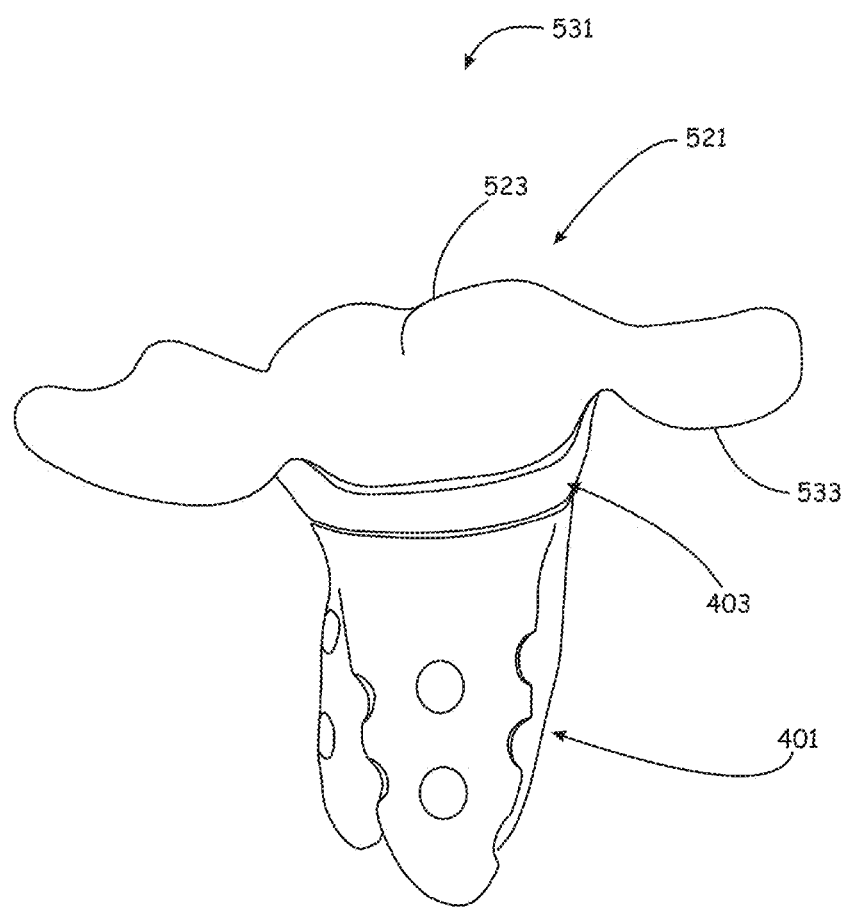
FIG. 64 is a perspective view of the exemplary prosthesis shown in FIG. 62 according to an embodiment of the present invention.

A cut away view of this prosthesis 500 is depicted in FIG. 58. In this view, it can be seen that the prosthesis 500 includes a one-part implant 509 (e.g., combined abutment and implant body) and a temporary crown portion body ("cap") 503 forming one part with its wings 505 attaching to the adjacent teeth 507. The cap 503 can be attached to the one-part implant 509 with adhesive means such as cement. However, a partially adhesive silicone 513 can also be used for attaching the cap 503 to the one-part implant 509. This provides the advantage that micro-movements of the cap 503 and wings 505 (as one part) are damped. This reduces the micro-movements of the implant 509, and thereby enhances the integration of the implant 509 into the extraction socket.

FIGS. 59-66 illustrate another embodiment of an integrated support device 521, which can be applied in place of the crown 405 (see, e.g., FIG. 41) to stabilize and provide primary stability to the dental implant 401 and to maintain the abutment 403, and through that, the dental implant 401, at a user desired position and inclination when positioned within and being integrated into the jawbone cavity of the pre-identified patient. According to the illustrated example, the integrated support device 521 (see, e.g., FIGS. 59 and 60) includes a prosthesis interface member 523, e.g., in the form of a temporary crown, configured to engage and land atop and surround substantial portions of an occlusal extending rising 415 of an abutment 403 connected to a dental implant 401 of a dental prosthesis 400 (see, e.g., FIGS. 44 and 61-64 positioned within a jawbone cavity of a pre-identified patient. Alternatively, the prosthesis member 523 can be connected to rising 181 of FIG. 28, 199 of FIG. 29, 213 of FIG. 31, 217 of FIG. 32, 423 of FIG. 40; 101 of dental implant 91 (see FIG. 19); or further alternatively, rising 117 of FIG. 20B, or indent 133 of FIG. 21, with modification. The integrated support device 521 also includes at least one, but more typically a pair of bonding wings 533 connected to or integral with the prosthesis interface member 523 and configured to bond to corresponding adjacent functional teeth (e.g., teeth 507, FIG. 65) when operably positioned thereon.

Figure 65:
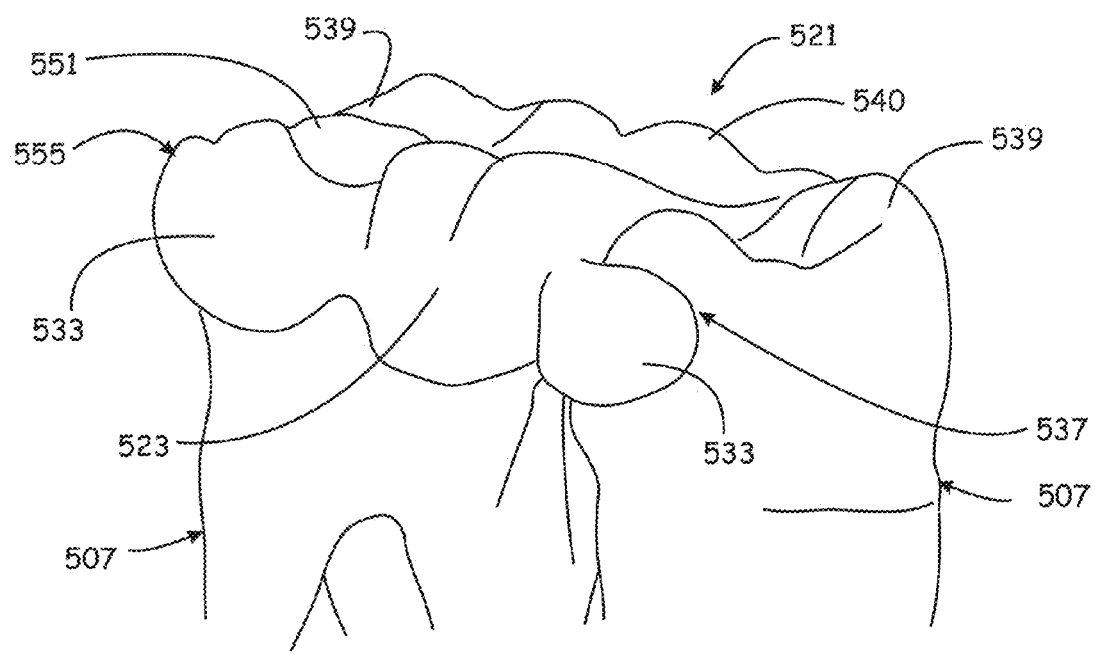
FIG. 65 is a perspective environmental view of an integrated support device connected to adjacent functional teeth according to an embodiment of the present invention.
Figure 66:
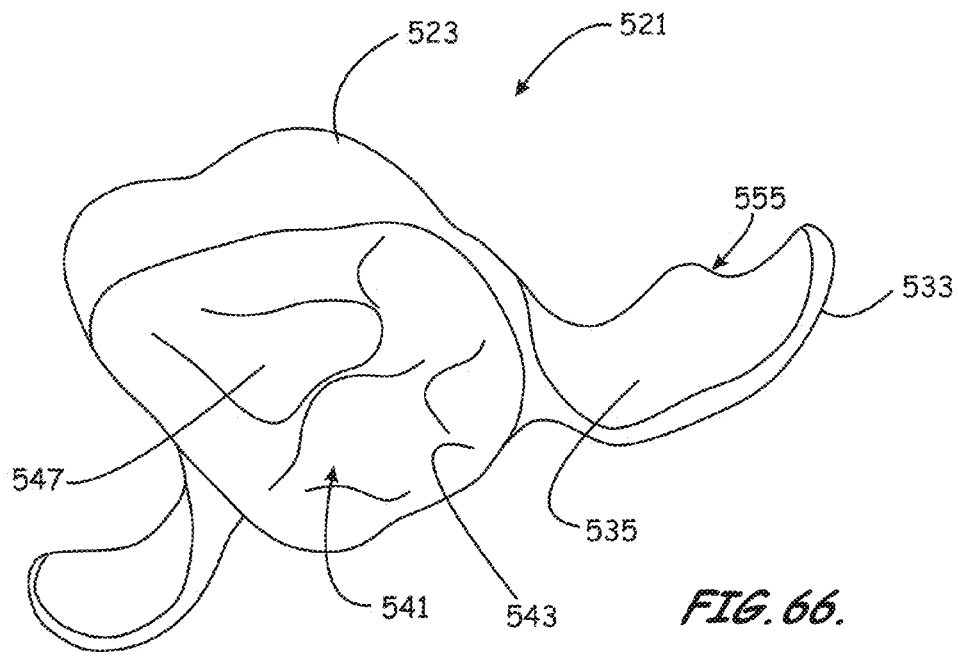
FIG. 66 is a perspective view of an integrated support device according to an embodiment of the present invention.
Figure 67:
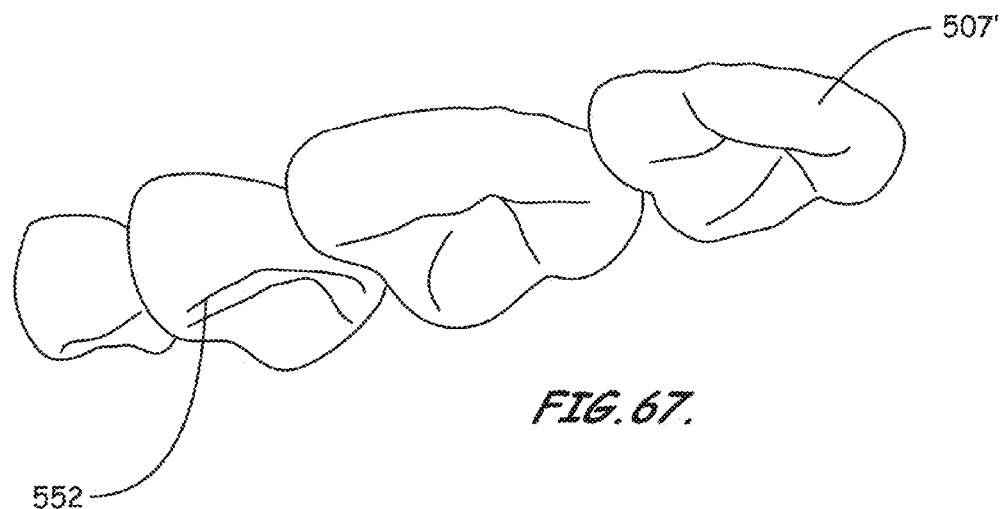
FIG. 67 is a perspective view of an occlusal portion of the crown surfaces of natural opposing teeth.
Figure 68:
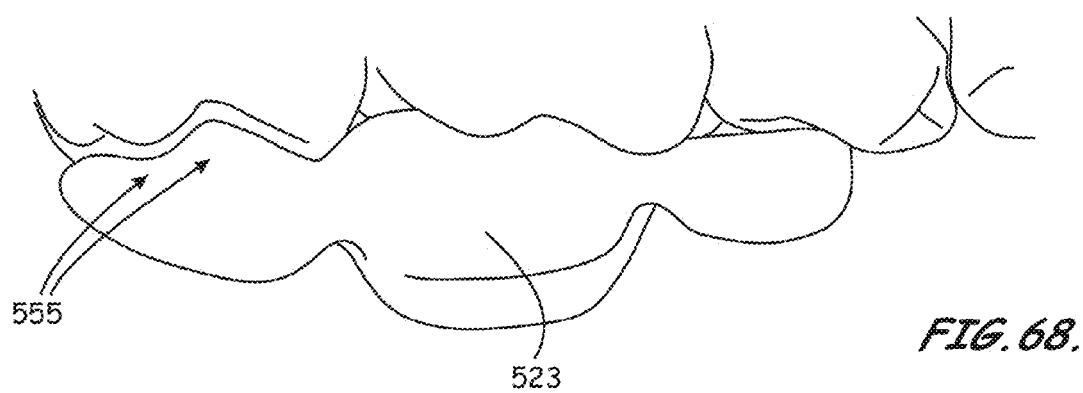
FIG. 68 is a perspective lingual view of an integrated support structure together with opposing crown portions illustrating the comparative shape of the bonding wings and illustrating that although covering the lingual and even an occlusally reaching portion from the adjacent teeth, the bonding wings can avoid an occlusal biting interference with opposing teeth according to an embodiment of the present invention.
Figure 69:
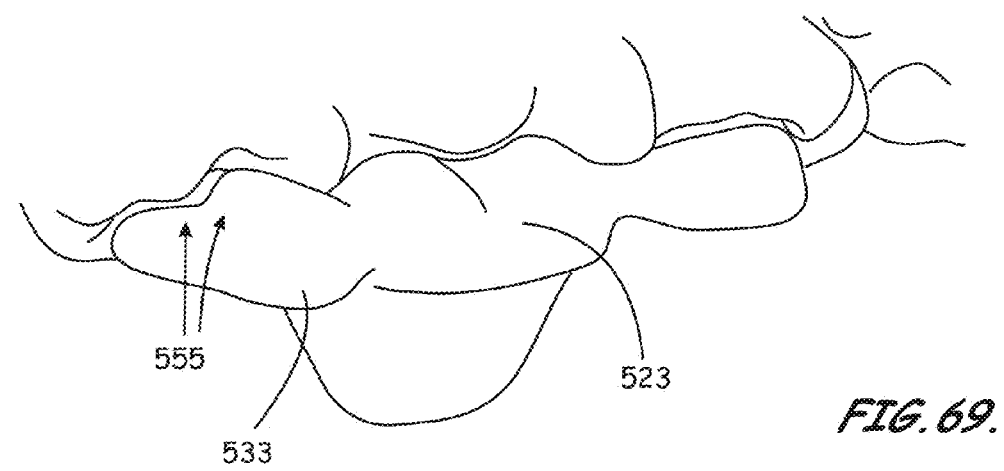
FIG. 69 is a perspective lingual view illustrating the integrated support structure of FIG. 68 at a different vertically angled lingual view according to an embodiment of the present invention.
Figure 70:
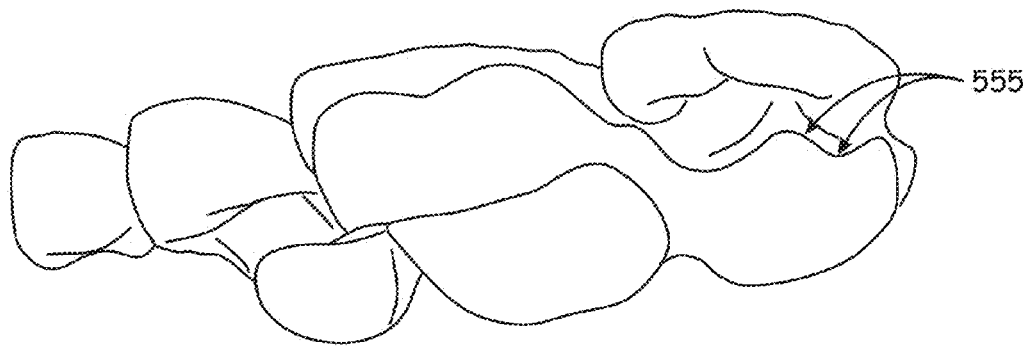
FIG. 70 is a perspective buccal view illustrating the integrated support structure according to an embodiment of the present invention.

As perhaps best shown in FIGS. 65 and 66, according to the exemplary configuration, each of the bonding wings 533 includes a tooth-facing outer surface portion 535 adapted to adhesively bond to an outer surface portion 537 of a crown 539 of the adjacent functional tooth 507. Beneficially, through an at least substantially rigid/semi-rigid connection of the prosthesis interface member 523 to an adjacent tooth or the adjacent teeth 507 (FIG. 65) via the respective bonding wing or wings 533 (see, e.g., FIGS. 59 and 66) and as best shown in the explosion view of FIG. 61 the at least substantially rigid/semirigid connection to the occlusal extending rising 415, the integrated support device 521 functions to at least substantially rigidly fixate the prosthesis interface member 521 to stabilize and provide primary stability to the dental implant 401 during the healing period and to maintain the assembly including the abutment 403 and the dental implant 401 at a user desired position and inclination.

According to the exemplary configuration, the user desired position and inclination reflects a geometrical relation to the one or more adjacent functional teeth 507 located adjacent the jawbone cavity and the dental implant 401 (see FIG. 64), determined via imaging data as understood by those of ordinary skill in the art. Additionally, according to such configuration, the outline of a cross-section of the crown portion 540 (FIG. 65) of the prosthesis interface member 523 correlates to an outline of a corresponding cross-section of the occlusal extending rising/portion 415 of the dental prosthesis 531 (shown in FIGS. 62 and 63). According to the exemplary configuration, the crown portion 540 of the prosthesis interface member 523 is custom manufactured for the specific pre-identified patient receiving the dental prosthesis 531. This can beneficially provide a higher quality custom device and/or provide for manufacturing a set or kit of devices including both temporary and permanent crown portions and the necessary primary support structure device or devices, ready for application with minimum effort on the part of the dental practitioner.

As perhaps best shown in FIG. 66, according to an exemplary configuration, in order to enhance the connection to the occlusal extending rising/portion 415 of the dental prosthesis 531 (see, e.g., FIG. 61), the prosthesis interface member 523 includes an occlusal extending recess 541 extending substantially into a body of the prosthesis interface member 523 to define a complementing interface surface 543. Beneficially, the occlusal facing surface 545 of the occlusal extending rising 415 and the complementing interface surface 543 of the prosthesis interface member 523 together create a form-lock fit when the occlusal facing surface 545 of the occlusal extending rising/portion 415 is operably positioned within the occlusal extending recess 541. According to the illustrated configuration, the occlusal facing recess 541 extending into the body of the prosthesis interface member 523 has an asymmetrical custom three-dimensional surface shape substantially directly correlated with an asymmetrical custom three-dimensional surface shape of the occlusal extending rising/portion 415 of the abutment 403. According to the illustrated configuration, the complementing interface surface 543 can also include a substantial asymmetric apical-facing indent 547 extending into the recess 541 (FIG. 66), which reflects, for example, a direct correlation with the surface shape of a medial section of the crown portion 540 (FIG. 65) of the prosthesis interface member 523.

As perhaps best shown in FIGS. 65 and 66, in order to improve positioning and/or to provide for manual positioning without the necessity for custom application tools, and to reduce the amount of structure of the bonding wings 533 extending lingually, as noted above, the bonding wings 533 can have a custom three-dimensional surface shape dimensioned to substantially match a three-dimensional shape of the outer surface portion 537 of the crown 539 of the adjacent functional tooth/teeth 507. The custom three-dimensional surface shape can beneficially be provided, for example, at the manufacturing facility prior to insertion of the dental implant 401 into the jawbone, and thus, prior to application of bonding material to the tooth-facing outer surface portion 535, and prior to bonding attachment of the tooth-facing outer surface portion 535 to the outer surface portion 537 of the crown 539 of the respective adjacent functional tooth 507, determined, for example, using imaging data. The imaging data can be obtained through various methodologies understood by those of ordinary skill in the art.

Figure 71:
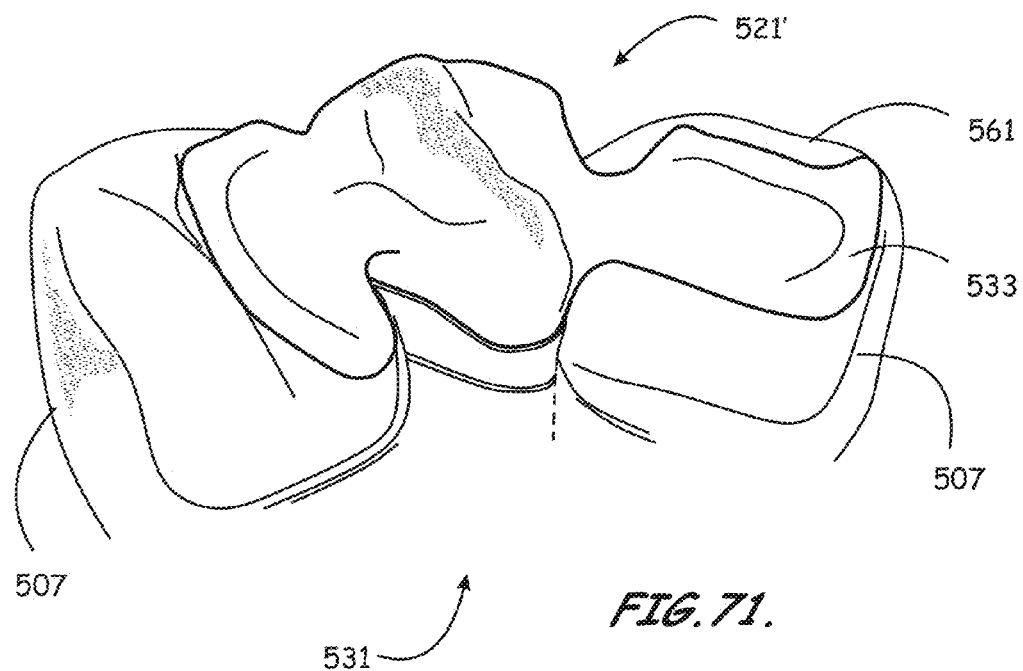
FIG. 71 is a perspective lingual view illustrating an integrated support structure adapted for application on natural anterior teeth according to an embodiment of the present invention.

As shown in FIGS. 65-70, beneficially, the bonding wings 533 can be dimensioned to be sufficiently small so as to not extend atop the portion of an occlusal surface 551 (FIG. 65) of the respective adjacent functional tooth or teeth 507 that is normally aligned to contact an occlusal surface 552 (FIG. 67) of a corresponding opposite-facing functional tooth 507' (when the respective tooth is a posterior tooth). That is, in order to improve alignment positioning, portions 555 of the bonding wings 533 (see, e.g., FIGS. 65-66 and 68-70) can extend atop portions of the adjacent functional teeth 507 with a low enough profile and in natural fissures or gaps so that they are not engaged by opposite facing teeth 507' when the jaws of the patient are in a normal closed position (see, e.g., FIGS. 68-70). Note, as perhaps best shown in FIG. 71, the bonding wings 533 of the integrated support device 521' are correspondingly also dimensioned so as to not extend atop a portion of an incisal surface 561 of a respective adjacent functional tooth 507 that would be normally aligned to contact a surface of a corresponding opposite-facing functional tooth (not shown) when the respective tooth is an anterior tooth.

Figure 72:
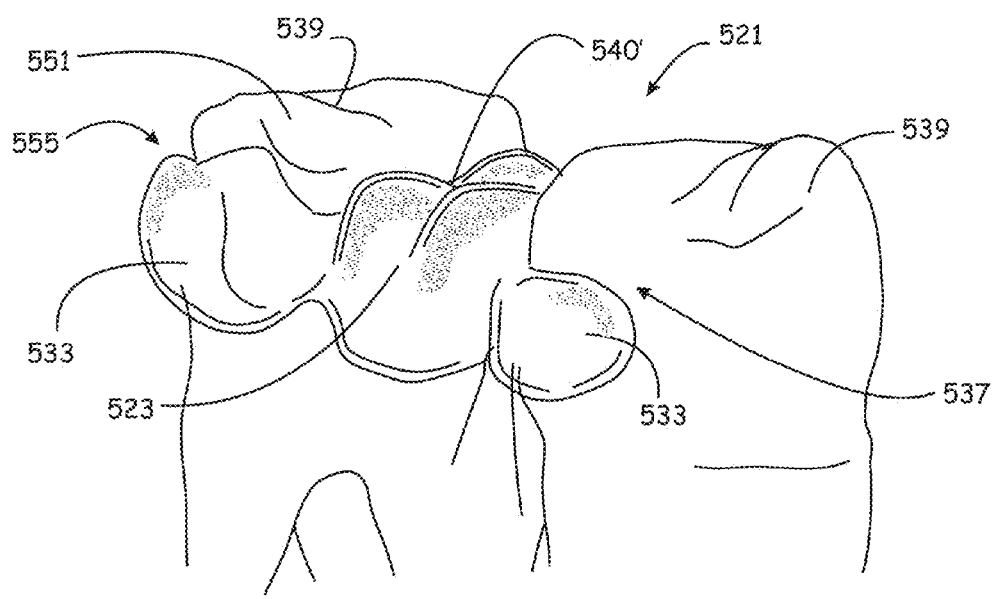
FIG. 72 is a perspective environmental view of an integrated support device connected to natural adjacent functional teeth according to an embodiment of the present invention.

Additionally, according to an exemplary configuration, the prosthesis interface member 523 provides a temporary crown portion 540' (FIG. 72), e.g., having an infra-occlusion to thereby avoid occlusal contacts with an opponent tooth when operably positioned.

Designing the Integrated Support Device

According to a preferred configuration, manufacturing of the integrated support device 521 is performed using various computer controlled machines and/or rapid prototyping as would be understood by those of ordinary skill in the art. Accordingly, to provide a truly custom integrated support device 521, a virtual model is first developed which can be utilized to provide the necessary data to control the various machines.

Figure 73:
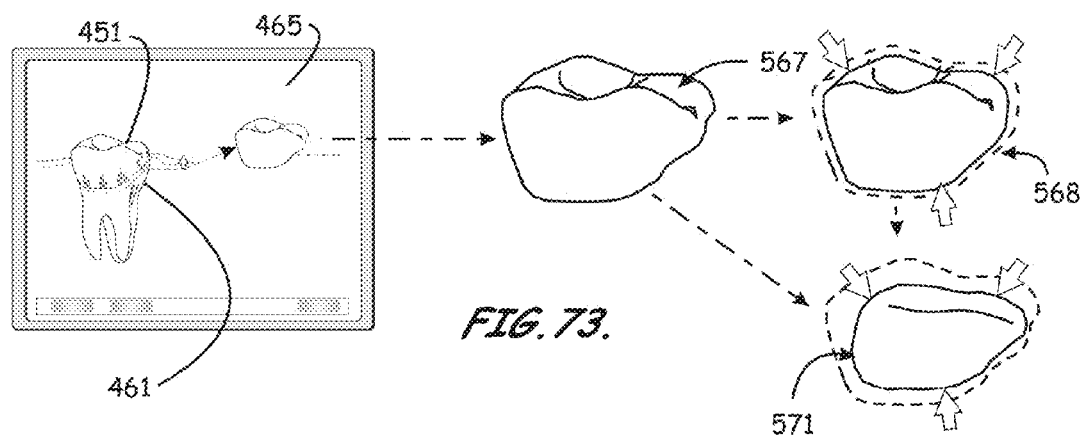
FIG. 73 is a sectional view illustrating copying and restructuring of parts of a virtual model according to an embodiment of the present invention.

As shown in FIG. 73, the step of forming a virtual model 553 (FIG. 77) of an integrated support device 521 such as that shown, for example, in FIG. 66 includes separating a portion of the three-dimensional virtual model 451 along the outer gum line 461 to form a virtual crown portion model 465 modeling the outer surface of the physical prosthesis interface member 523 (FIG. 66).

According to the illustrated embodiment, the modeled outer surface 568 of the virtual prosthesis interface member 591 (see, e.g., FIG. 75) models a prosthesis interface member 523 having a full-size crown portion (see, e.g., FIG. 65). If it is desired to manufacture a crown portion having a slight infra-occlusion designed to avoid occlusal contacts with an opponent tooth during the healing phase (see, e.g., FIG. 72), the step of forming the virtual integrated support device model 553 (FIG. 77) can also include copying the modeled virtual crown portion 465 to form an outer surface model 567 of the virtual prosthesis interface member 591 and reducing the dimensions of at least portions of the outer surface model 567 of the virtual prosthesis interface member 591 (FIG. 75) to form the infra-occlusal outer surface model 568 of the virtual prosthesis interface member 591.

As noted above, if the goal is to model a virtual prosthesis interface member outer surface 568 having a crown portion of reduced (or enlarged) size, according to the exemplary embodiment, the step of forming the virtual integrated support device model 553 also includes copying at least portions of the outer surface model 567 of the virtual prosthesis interface member 591 (or virtual crown portion 465 or outer surface model 568) and reducing the dimensions of at least portions of the respective model; and in the exemplary configuration which provides enhanced structural stability, smoothing/adjusting the contours to form a virtual occlusal extending rising interface model 571.

Figure 74:
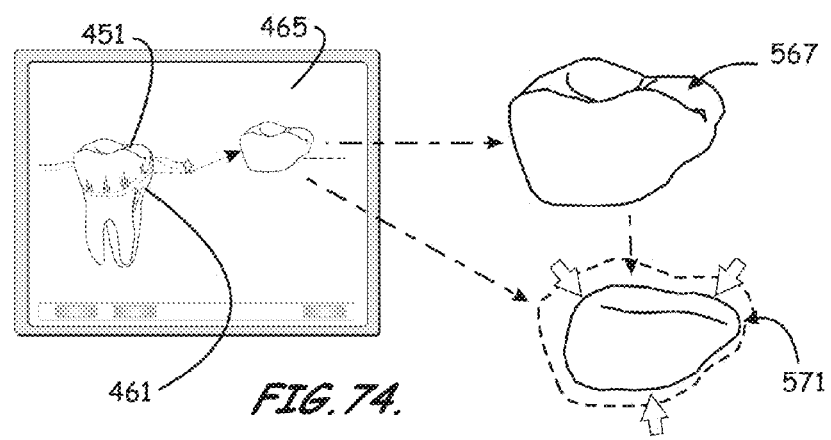
FIG. 74 is a sectional view illustrating copying and restructuring of parts of a virtual model according to an embodiment of the present invention.
Figure 75:
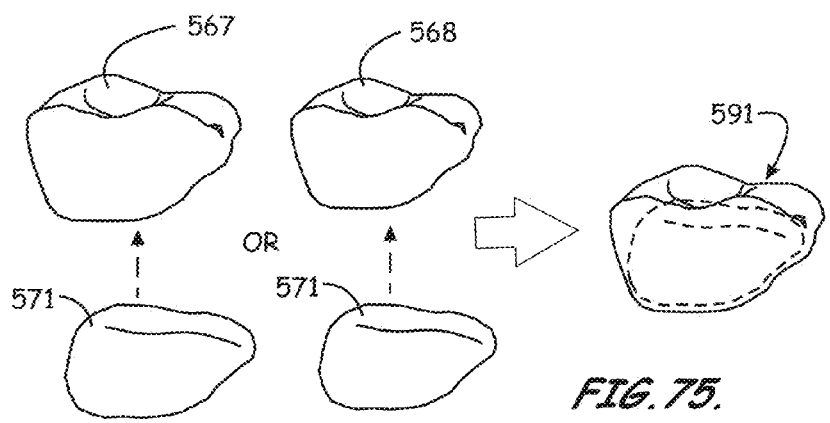
FIG. 75 is a sectional view illustrating the combining of virtual models to form a virtual prosthesis interface member model according to an embodiment of the present invention.

If the goal is to model a dental prosthesis having full-size crown, as perhaps best shown in FIGS. 74 and 75, according to the exemplary embodiment, the step of forming the virtual integrated support device model 553 (FIG. 77) includes copying at least portions of the modeled virtual crown portion 465 to form the virtual outer surface model 567 of the virtual prosthesis interface member 591. The step also includes copying at least portions of the modeled virtual crown portion 465 or outer surface model 567 of the virtual prosthesis interface member 591 and reducing the dimensions of at least portions of the respective model; and in the exemplary configuration which provides enhanced structural stability, performing the step of smoothing/adjusting the contours to form the virtual occlusal extending rising interface model 571.

As shown in FIG. 75, the step also includes combining the modeled outer surface model 567 of the virtual prosthesis interface member 591 or modeled virtual crown portion 465 (e.g., for same-size modeling) or outer surface model 568 (e.g., for reduced/enlarged size modeling) with the virtual occlusal extending rising interface 571 to form a virtual prosthesis interface member 591 of the virtual dental prosthesis model 453 (FIG. 56), e.g., modeling a physical crown 405 (see FIGS. 40-41).

As shown in FIG. 76, forming a virtual bonding wing model 592 modeling a bonding wing 533 having a tooth-facing surface configured to bond to a corresponding adjacent functional tooth and combining the prosthesis interface member landing surface of the virtual bonding wing model 592 with the corresponding surface of the virtual prosthesis interface member 591 to form the interim model 593. The virtual bonding wing model 592 can be produced by slicing a skin portion of a model of the adjacent functional teeth 507 (FIG. 65) and the non-functional tooth, if available. Note, the skin portions can be defined and virtually combined by free-form surfaces (e.g. stitched together) in the virtual domain with a surface modeling CAD software (e.g. Geomagic STUDIO 11) running on a computer.

As shown in FIG. 77, the step also includes combining the virtual bonding wing model portion of interim model 593 with a duplicate copy 595 of the virtual bonding wing model 592 to provide a desired thickness to the bonding wing model portion to form the virtual integrated support device model 553, e.g., modeling a physical integrated support device 521 (see FIGS. 59-60 and 65). Note, the thickness of the virtual bonding wing model 592 can be uniformly defined, but also non-uniformly distributed, so that, for example, the wings portions of the models are designed to have a reasonable stability to thereby provide primary stability when the physical integrated support device 521 is fabricated with respect to the virtual integrated support device model 553 and assembled with the transgingival interlock abutment 403 (FIG. 64) and the implant body 401 (FIG. 64) and bonded to the corresponding adjacent functional teeth (e.g., teeth 507, FIG. 65) when operably positioned thereon. The thickness of a substantial part of each wing portion of the virtual bonding wing model 592 should be in a range of between approximately 0.3 mm and 2 mm, preferably approximately 0.8 mm, while the middle portion can be, for example, infinitesimal small or not existent as long as each of the aforementioned wing portions of the virtual bonding wing model 592 intersect or otherwise virtually connect with a substantial thickness to the virtual prosthesis interface member 591, when virtually combined or superposed to the physical integrated support device 521.

Note, that all combinations of partial surface shells described in this specification can include a design step of closing potential gaps between adjacent shell portions while patching the surface components, as such design step is understood by those of ordinary skill in the art to build numerically definite 3D surface objects i.e. virtual models of physical parts used for further CAD/CAM processing. Note also, that any and all virtual partial models described in this specification can be combined (e.g. merged by Boolean 3D combination or stitched together) in the virtual domain, and/or simply superposed when displayed, and/or considered in addition to each other when considered in subsequent computer aided manufacturing (CAD) process when actually fabricating the physical parts from or at least responsive to the combined model or the superposed or otherwise additionally considered partial models. As known to those of ordinary skill in the art, however, it is sufficient when the models have adjacent, identical surfaces or surfaces that intersect (or any combination thereof) in order to be combined or superposed in the virtual domain or when considered in addition to each other when actually fabricating the physical parts that represents the merged model or the superposed or adjacently considered partial models.

Customized Tooth-Conforming Splint

According to various embodiments of the present invention, primary stability is favorably achieved by a custom made splint that connects parts of a dental prosthesis with an adjacent tooth or teeth or other dental structures like existing implants, bridges and the like. The concept of a splint that is custom made in the laboratory in advance serves two purposes, the correct positioning of the prosthesis and the achievement of reasonable primary stability.

Figure 78B:
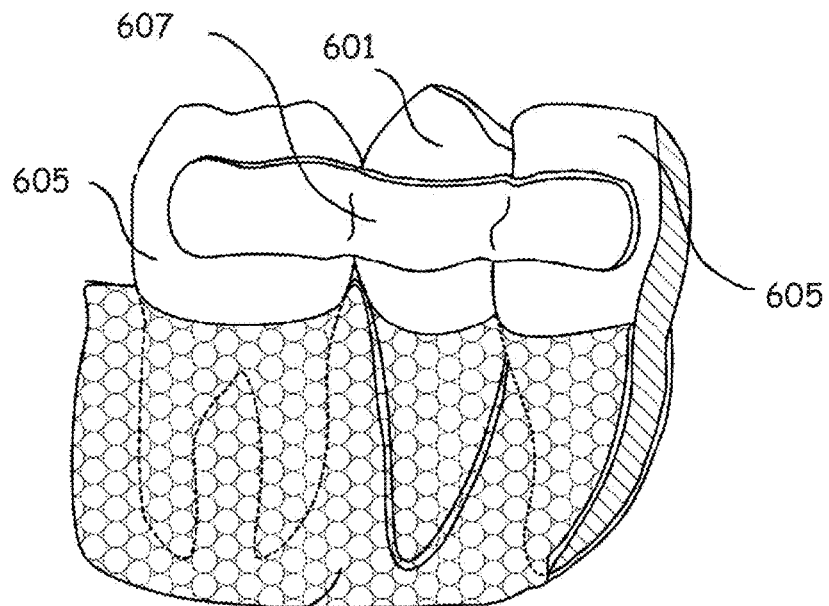
FIGS. 78A-78B each illustrate a single-tooth prosthesis and a custom-made splint for positioning and fixation of such to the adjacent dental structure, according to an embodiment of the present invention.
Figure 78A:
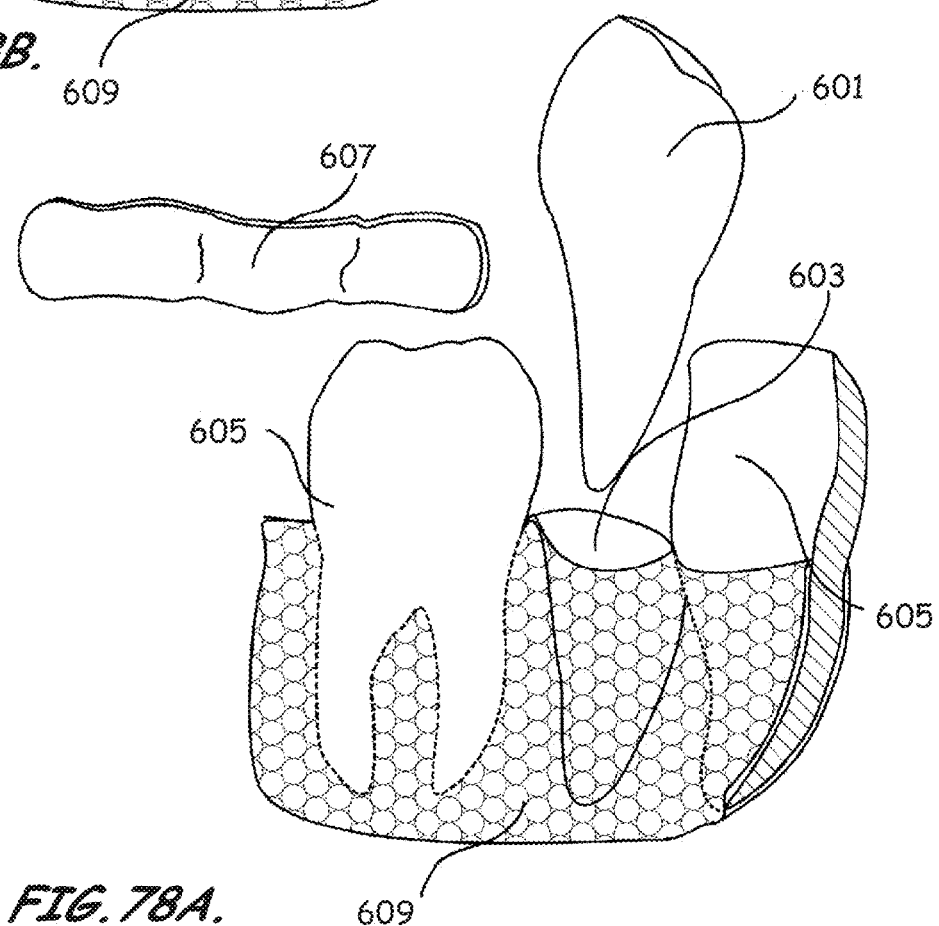

FIGS. 78A-78B illustrate a single-tooth prosthesis 601, having a manufactured crown portion and a manufactured root portion. The shape of each is derived, for example, from in-vivo imaging data prior to the extraction of the tooth to be replaced. By extraction of said tooth to be replaced, the extraction void 603 was created. The adjacent teeth (mesial and distal of the extraction socket) are healthy natural teeth 605. The extraction was indicated, for example, due to a serious porosity of the root of the extracted tooth. The extraction socket was partially curetted by the doctor of record, removing damaged soft tissue. Antibiotic tablets are given orally to the patient in advance to suppress the inflammation and to avoid additional infection as a result of the clinical trauma of removing the tooth. The crown and the root shape are derived from the imaging data. In addition, the crown shape of the adjacent teeth 605 and a desired position and inclination of the prosthesis are derived from the imaging data. Based on all this data a custom-shaped splint 607 is designed and fabricated. The splint is used to position and orient the prosthesis 601 in the dental structure 609 building the extraction void in geometrical relation to the adjacent teeth 605. Being held in the desired position and orientation, the custom-shaped splint 607 is connected with adhesive means to the prosthesis 601 and the adjacent teeth 605. For example, light curing adhesives are used in that context. Alternatively, dual curing (light and chemical curing after mixing two components) adhesives can be used. In an exemplary clinical process, a moist-tolerant resin enforced cement (e.g. GC Fuji ORTHO SC) is used.

Finally, the prosthesis 601 is fixated in its desired position and the crown portion, is thereby integrated into the occlusion and articulation of the patients dental anatomy. Slight corrections performed by the doctor of record with a high-speed rotating instrument may be necessary to optimize the occlusal contact points. The prosthesis can be immediately loaded by the patient for the day-to-day use of mastication, since the splint distributes the functional load from the dental prosthesis 601 to the adjacent teeth 605. With that, the custom splint connected to a prosthesis and adjacent teeth or other dental structures provides the primary stability while either the perio-type integration or the osseointegration takes place.

According to various embodiments of the present invention, and each of the methods described above, the dental prosthesis 601 (FIGS. 78A and 78B), or respectively the dental prosthesis 602 (FIG. 79), can have a three-dimensional surface shape matching, or at least substantially matching, that of the side-crown portion of the tooth to be replaced. Correspondingly, the portions of the splint 607 shaped to connect to the dental prosthesis 601/602 can have a complementary three-dimensional surface shape matching, or at least substantially matching the surface shape of the corresponding side-crown portion of the dental prosthesis. Additionally, the one or both portions of the splint 607 shaped to connect to the adjacent tooth or teeth 605, respectively, can have a complementary three-dimensional surface shape matching, or at least substantially matching that of the side crown portion of the respective adjacent tooth or teeth 605.

According to an embodiment of the invention, the splint 607 can also have an extension that covers, for example, not only the lingual crown portions of the prosthesis and of the adjacent teeth 605, but includes also incisal edges in the event anterior teeth are affected or cusps in the event posterior teeth are affected, preferably shaped in such a manner that the extension does not to interfere with the occlusion of the upper and lower dentition of the patient receiving the appliance when inserted. In a further embodiment, the extension is shaped in such a manner that significant occlusal surfaces of the teeth of interest can also be covered by the splint. According to an embodiment of configuration, the extension does not, however, extend beyond the occlusal or incisal surfaces to engage the buccal or labial surface (for lingual-positioned splints). In an exemplary embodiment, the design and the fabrication of the splint 607 may include such contours covering additional surfaces or portions thereof to enable better positioning of the prosthesis, with such contours to be physically removed after bonding in the patient's mouth by the doctor of record.

Figure 79:
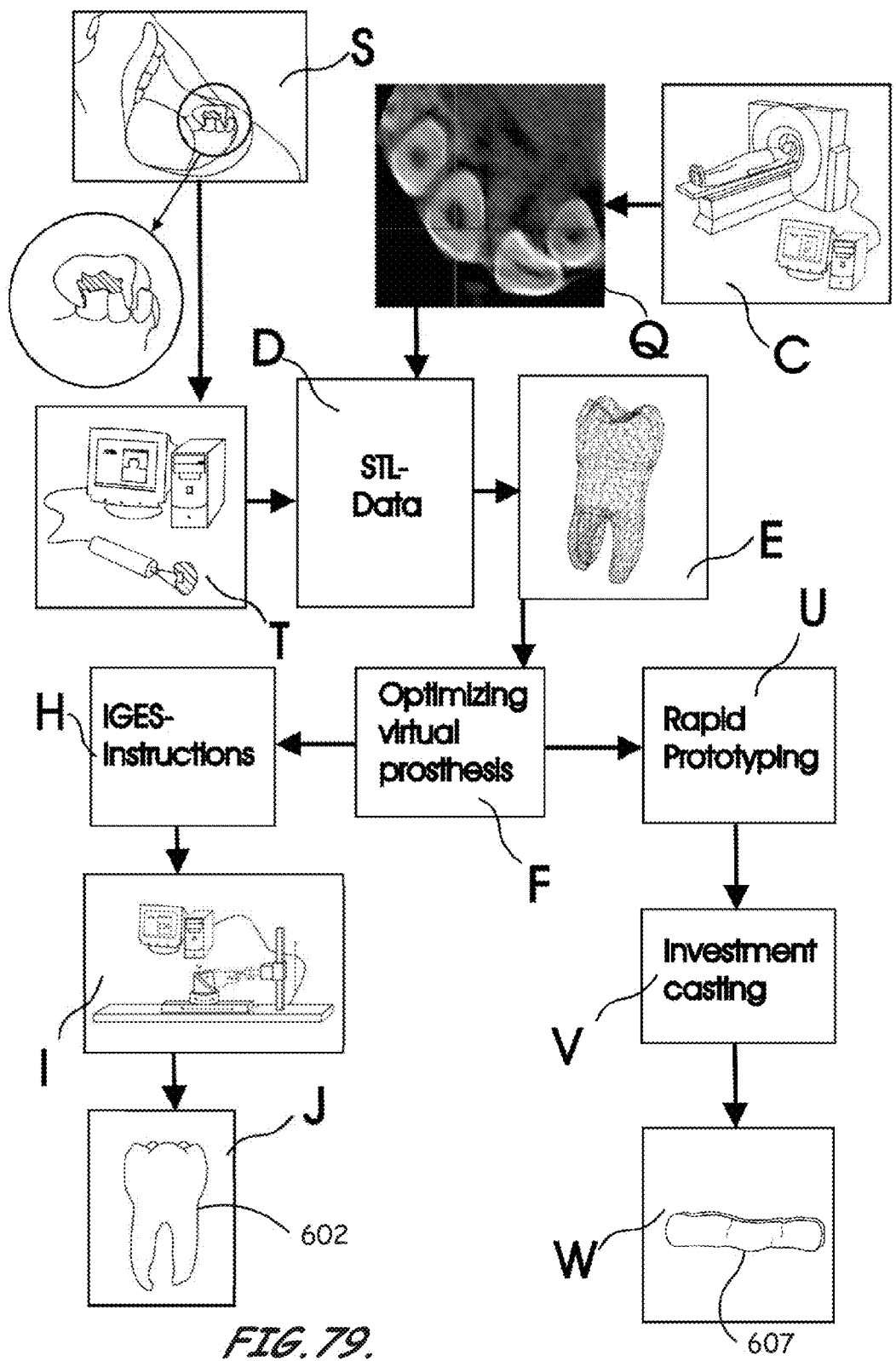
FIG. 79 illustrates the process steps of fabricating a one-piece prosthesis partially from in-vivo imaging data and partially from imaging data of impressions, merging those imaging data, design a prosthesis and a custom splint, and fabricating the prosthesis and the splint by computer numerical control (CNC) machining, according to an embodiment of the present invention.

In the context of the aforementioned custom splint, FIG. 79 shows, for example, the process steps of fabricating a prosthesis 602 and such a splint 607. A partial silicone impression is taken from the mouth of the patient representing the dental (occlusal) crown anatomy in the neighborhood where a prosthesis will be integrated (step S). The silicone impression can include, for example, not only the crown and gingival situation of the jaw of interest, but also the occlusal situation of the corresponding crowns of the opponent jaw (see, e.g., 507' and 552 of FIG. 67). It is also possible that the situation is defined by more than one silicone impression, impressions made from other materials than silicone (e.g. alginate), or that the impressions include a wax bite that defines the upper to lower jaw relationship. The impression is (or the impressions are) scanned and three-dimensional STL data of the shape are derived representing the crown geometry of the tooth to be extracted, the crown geometry of the adjacent teeth (and, in an exemplary embodiment, of the opponent teeth), and the geometrical relation between those crown data (step T). Additionally, the patient's dental anatomy is imaged with a computed tomography device (step C). Computed tomography (CT) is a medical imaging method employing tomography where digital geometry processing is used to generate a three-dimensional volumetric image of the internals of an object that can be displayed as a large series of layered two-dimensional grey scale X-ray images. The layered grey scale X-ray data in digitized format is then computer analyzed and three-dimensional STL data are derived representing the dental anatomy of the patient (step Q). All aforementioned STL data can be scaled, merged and/or combined (step D) to generate accurate three-dimensional shape data from tooth to be replaced and the adjacent (and opposing) dental anatomy (step E). Boolean algorithms can be used to generate combined data of high-quality. In a first design of the prosthesis, its position and orientation within the adjacent (and opposing) dental anatomy, especially in relation to the crown portions of the adjacent teeth, and a second design of a custom shaped splint that includes shape portions of the crown of the prosthesis and of the crowns of the adjacent teeth, are derived. The first and the second design may be modified and optimized (step F). This can be done automatically or interactively by having a technician operating the respective computer equipment. Computer numerical control data (CNC), for example, in IGES format for computer aided manufacturing (CAD) devices are derived from the final three-dimensional design data (step H). Usually rapid prototyping equipment is having the aforementioned step already integrated. The prosthesis is fabricated in response to the IGES data, for example, by a CAM high-speed 5-axis milling/grinding machine (step I and J). Additionally, the rapid prototyping machine, such as, for example, a layer-by-layer wax printing machine, is fabricating a three-dimensional wax representation (sample) from the three-dimensional design data (step U). The sample is prepared and embedded for lost wax investment casting, whereby the wax sample is burned out and the investment mould is filled with liquid precious metal (e.g., dental gold alloy; step V). After cooling down to room temperature, the embedding material is removed, the runner is cut-off and the splint is polished and surface prepped for bonding (step W). It should be noted that while FIG. 79 contemplates possibly interaction with an operator, one skilled in the art would readily appreciate that certain steps are combined, further differentiated, and that this functionality may be partially or fully automated. The aforementioned CAD/CAM machining and the rapid prototyping are exemplary embodiments. It would also be possible to employ CAD/CAM machining to fabricate the splint and/or to use rapid prototyping to fabricate the dental prosthesis; or if the dental prosthesis is designed as an assembly of parts or components, any combination thereof.

Figure 80:
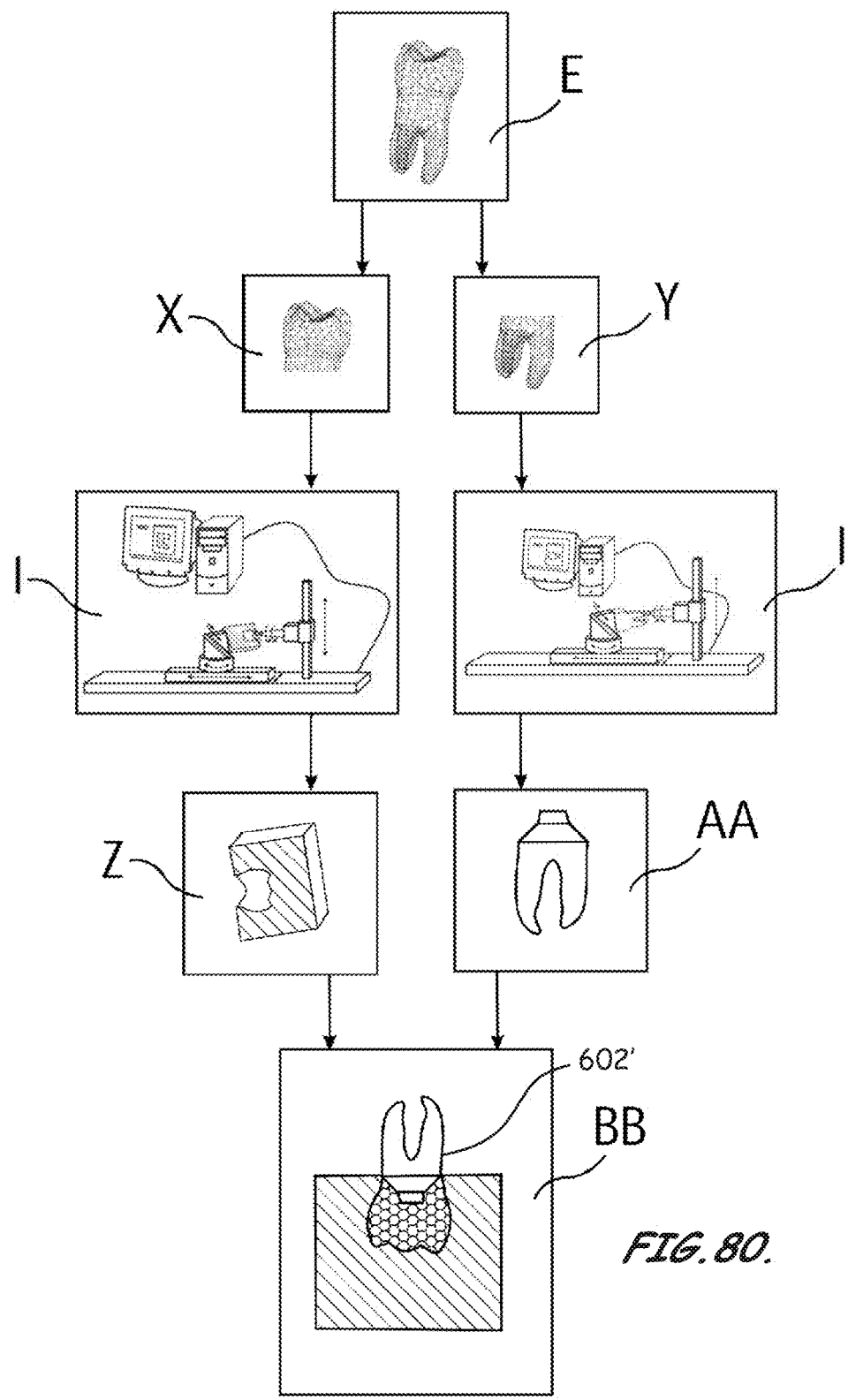
FIG. 80 illustrates the process steps of fabricating a one-piece prosthesis from design data, completing the design by segmenting the prosthesis in a root portion that includes an abutment and a crown portion, fabricate the root portion by computer numerical control (CNC) machining, fabricating a negative shape of the crown portion as a mould by computer numerical control (CNC) machining, and use the root portion and the mould to complete the one-piece prosthesis shaping the crown portion, according to an embodiment of the present invention.

In yet another embodiment, a prosthesis 602' is segmented and such segments are fabricated using different manufacturing technologies. FIG. 80 shows the process steps of receiving design data of a prosthesis 602' in STL format (step E), separating portions in a computer aided design (CAD) process (step X and Y), deriving computer numerical control (CNC) data and utilizing computer aided manufacturing (CAM) machinery, for example, high-speed milling/grinding machines (step I) to fabricate the respective portions (step Z and AA) in response to the CNC data. Note, in step I and Z a mould is manufactured, for example, substantially inverse, with or without a shrinking factor, to the shape shown in step X. The separated portions used to make the prosthesis 602' (step BB). This can be performed by molding a crown portion substantially representing the shape definition shown in step X atop of the part shown in step AA by means of the mould shown in step Z.

Figure 81:
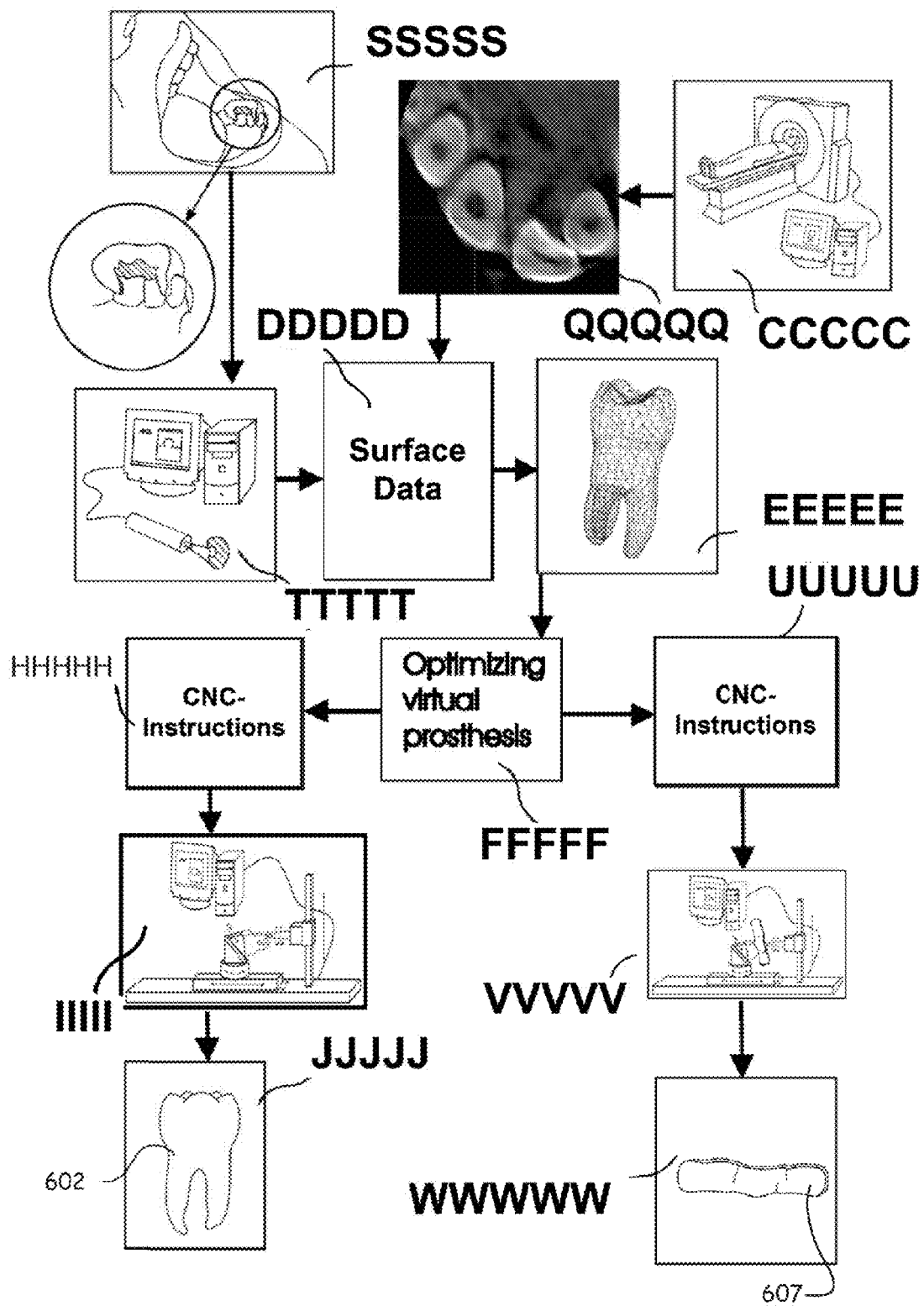
FIG. 81 illustrates an overall fabrication method of the prosthesis and its dedicated parts, including a splint, according to an embodiment of the present invention.

In another embodiment of the fabrication process of a prosthesis 602 together with a splint 607, shown in FIG. 81, in a first step (SSSSS) a physical impression of the denture of the patient is taken, e.g., with silicon material. In a further step (TTTTT), the crown geometry of the patient's crowns are obtained from the patient's dental anatomy and translated to three-dimensional STL-data. Additionally, the patient's dental anatomy is imaged with a computed tomography device (CCCCC). The layered grey scale X-ray data in digitized form (QQQQQ) are analyzed, three-dimensional STL-data (DDDDD) are derived representing the anatomy of the patient's denture. Note, there are other numerical formats available to describe the surface data of a three-dimensional virtual object or model, so that whenever in this specification a STL data format is referenced, it should be read as "3D surface data, for example in STL format". The grey scale X-ray (QQQQQ) data can be represented in the format of the DICOM standard (DICOM: Digital Imaging and Communications in Medicine). In a further step (EEEEE), Boolean algorithms are used to generate combined data of high quality of a virtual prosthesis. The data of the virtual prosthesis are optimized (FFFFF), e.g., automatically or interactively by a technician operating the respective computer equipment. From the data of the virtual prosthesis, computer numerical control (CNC) instructions are derived. These are CNC-instructions of two kinds. Firstly, CNC-instruction are derived for fabricating the dental prosthesis in a CAM (Computer-added Manufacturing) high-speed milling/grinding machine (IIIII and JJJJJ). Moreover, CNC-instructions (UUUUU) are derived for fabricating a splint in step (VVVVV and WWWWW) that individually fits to the corresponding prosthesis.

In a further embodiment of the aforementioned fabrication process, the two steps SSSSS and TTTTT can be combined to one step. Therefore, a three-dimensional camera can be used as known from the CEREC three-dimensional camera systems provided by the Sirona Group to avoid the process (SSSSS) taking a physical impression of the dental anatomy of interest. As in the fabrication process depicted in FIG. 81, a computed tomography device is used for imaging the dental anatomy of the patient's tooth to be replaced and its adjacent teeth.

From the surface data, the CNC-instructions can also be derived for a chair side fabrication device. Such a chair side fabrication device for dental prostheses is known from the in Lab MC XL milling unit which is offered by the Sirona Group. Therewith, in an exemplary embodiment of the present invention, the prosthesis and the corresponding splint can be fabricated at the dentist's site. Firstly, this is a simplification of the overall fabrication and delivery process. Especially, for dentists that have their own milling unit for fabricating crowns etc., the chair side production enhances the overall treatment process and saves time, e.g., in cases where fast replicas are needed by a patient.

Figure 82:
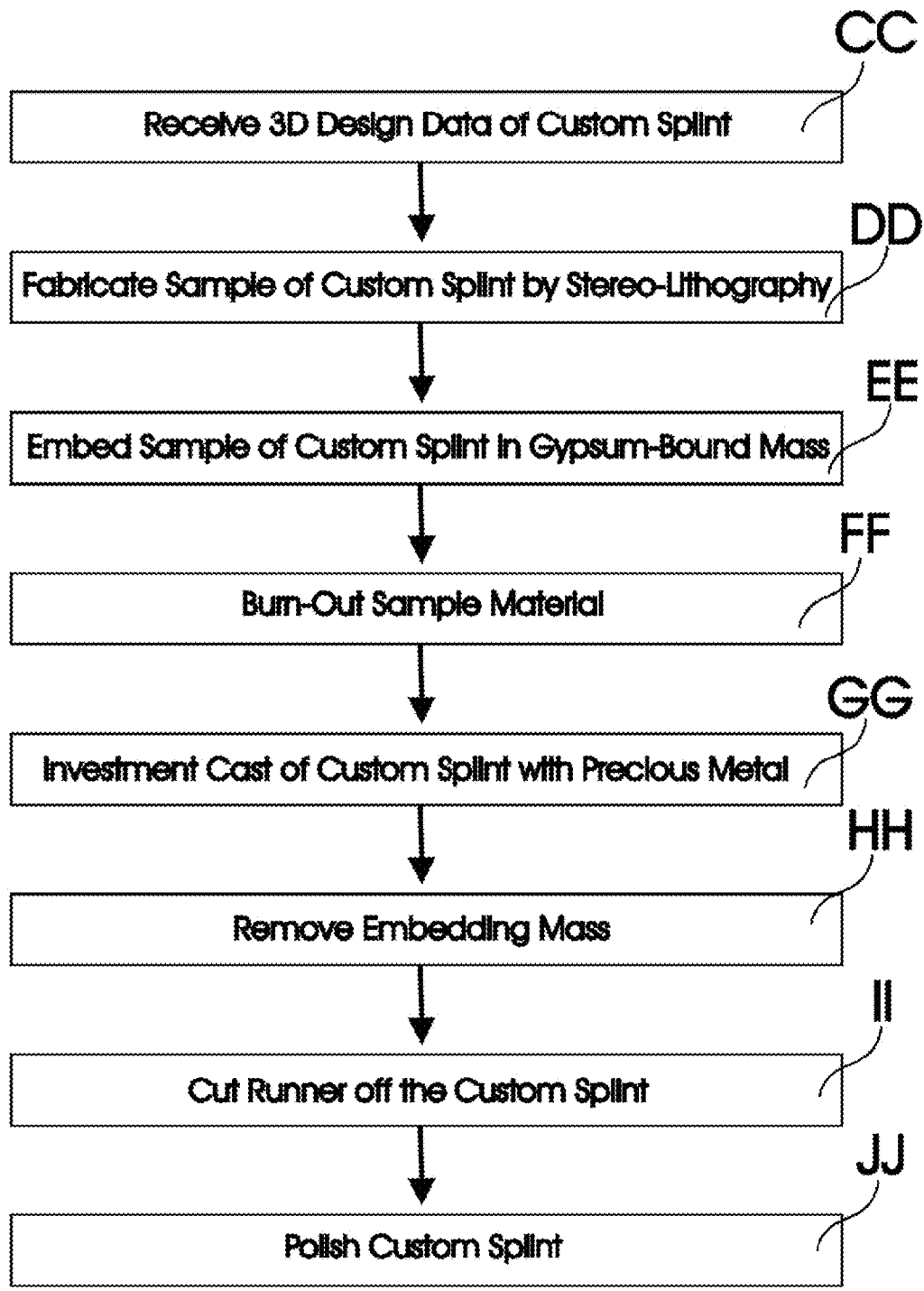
FIG. 82 illustrates the process steps of fabricating the custom splint from design data, and fabricating a model of the splint by rapid prototyping, build a mould around the splint, burning out the model and cast the splint by investment casting, according to an embodiment of the present invention.

In another embodiment, the custom splint is fabricated in an indirect method for example, by lost-wax investment casting. FIG. 82 shows the process steps of fabricating a custom splint (e.g., splint 607) from design data, and fabricating a model of the splint by rapid prototyping, building a mould around the splint, burning out the model and casting the splint by investment casting. As shown in the figure, the process starts with receiving the 3D design data of a custom splint (step CC), then a sample part of the custom splint is fabricated using stereo-lithography conforming to the design data (step DD). The sample part is embedded (step EE) in, for example, a gypsum-bound investment material (like Cera Fina, Whip Mix, U.S.A.). The investment mould is heated and the material of the sample part is burnt out (step FF). The mould filled by vacuum or centrifugal casting with liquid precious alloy (for example, Argenco 42 Type IV extra hard, The Argon Corporation, U.S.A.—step GG), and the embedding mass is removed (step HH). The casting runner is cut from the custom splint (step II), and the custom split is polished and prepared for bonding (step JJ). It should be noted that while process contemplates possible interaction with an operator, one skilled in the art would readily appreciate that certain steps can be combined, or further differentiated, and that this functionality may be partially or fully automated. Alternatively to the precious metal, the investment casting can be done with stainless steel or other suitable non-precious dental alloy known to those skilled in the art. In yet another embodiment, the custom splint is perforated or prepared with retention features on the bonding surface (like a mesh) for better light curing capabilities and better bonding strength. Note, the individual process steps disclosed in FIG. 79 to 82 can be employed to fabricate other components of the dental prosthesis. For example, the process steps shown in FIG. 82 can be employed to fabricate either one or more of the parts 521, 403 and 401 shown in FIG. 61, or, for example, the process steps shown in FIG. 81 can be modified to combine the virtual prosthesis design with the virtual splint design and to segment this combination in multiple parts, to make in step IIII and JJJJJ the parts 403 and 401 shown in FIG. 61, while step UUUUU and WWWWW can be modified to make part 521 shown in FIG. 61.

Figure 83:
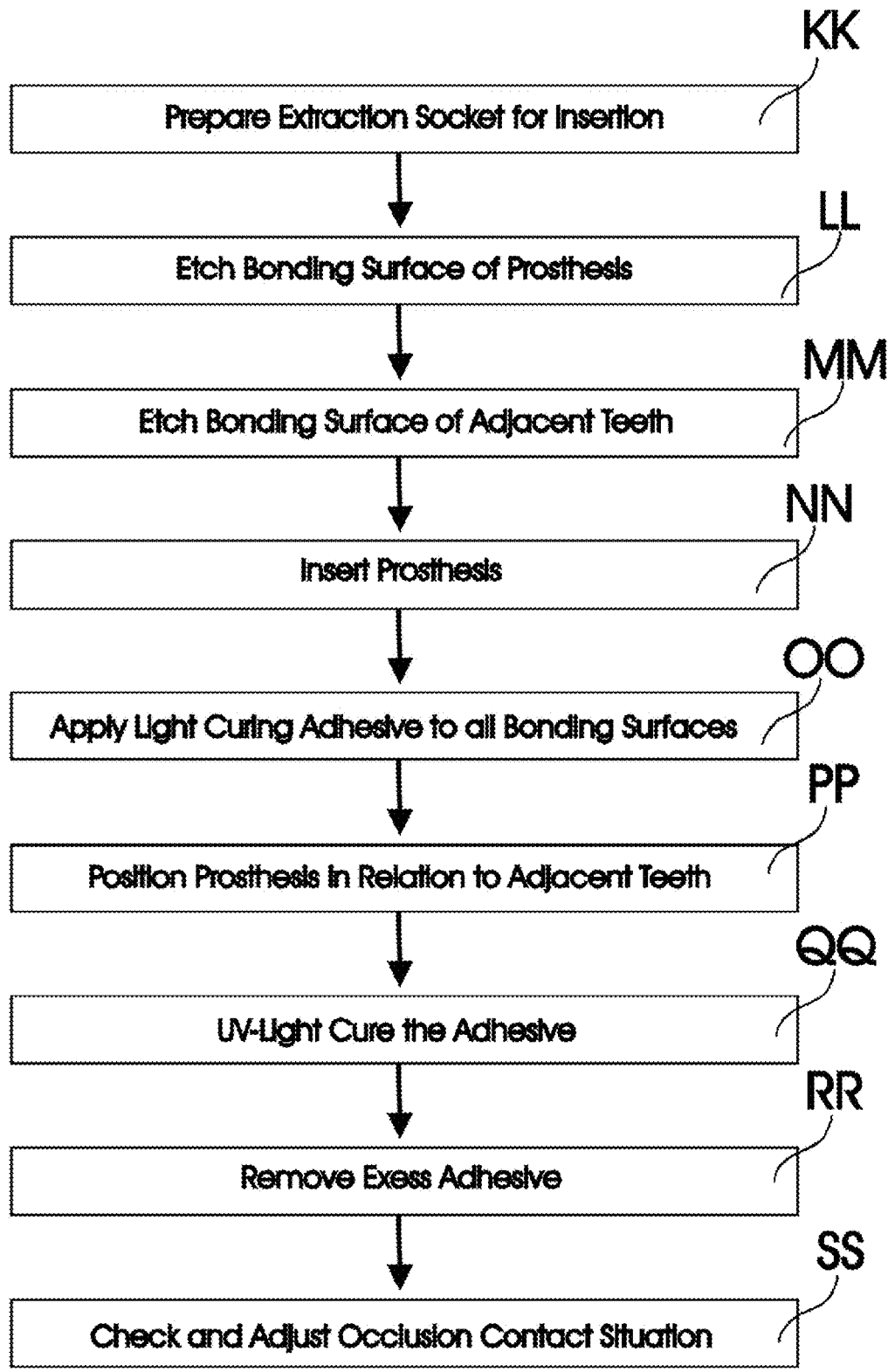
FIG. 83 illustrates the process steps of clinically inserting a one-piece prosthesis into an extraction socket, positioning the prosthesis in relation to the adjacent teeth with the custom splint and fixating the prosthesis in relation to the adjacent dental structure with adhesive means, according to an embodiment of the present invention.

In another embodiment, the clinical process of integrating the prosthesis 601/602 is performed as shown in FIG. 83. The process begins by preparing the extraction socket for insertion, which may include rinsing (step KK), micro-etching (sandblasting) and/or etch (e.g., phosphoric acid) bonding the surface of prosthesis (step LL), micro-etching (sandblasting) and/or etch (e.g., phosphoric acid) bonding surface of the adjacent teeth or other dental structures (step MM). Once the extraction socket is prepared, the prosthesis is inserted (step NN), applying light curing adhesive to all bonding surfaces (step OO). The prosthesis is then positioned and oriented in the desired geometrical relation to the adjacent teeth or other dental anatomy of interest using the custom splint as a positioning aid or guide (step PP). The prosthesis and the splint are held firmly in position while the adhesive is light cured with a dental UV-light curing device (step QQ) in order to fixate the prosthesis in its desired position. Excess adhesive is removed (step RR), and a final check and adjust—if necessary—of the occlusion and articulation of the patient in respect to the contact situation of the prosthesis to the teeth or other dental structures of the opponent arch is performed (step SS).

Figure 84:
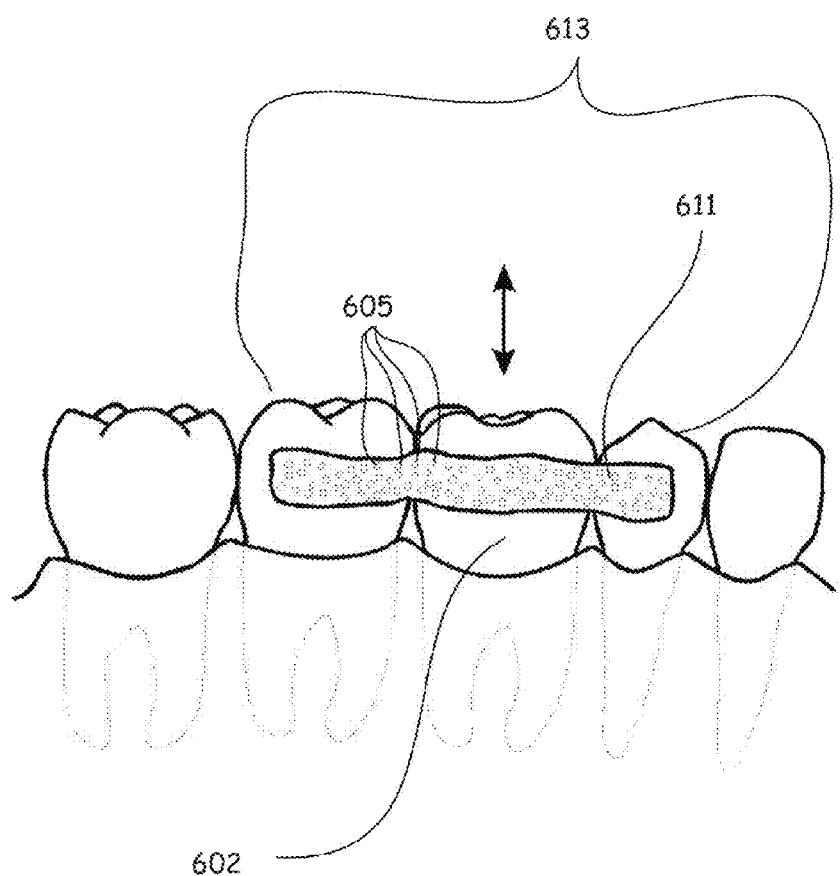
FIG. 84 illustrates a perforated splint comprising holes, according to an embodiment of the present invention.

In a further enhancement of the present invention shown in FIG. 84, the attachable splint 611 provides a number of recesses 613 formed as holes. Other methods of perforation may be used. This enhancement of the attachable splint 611 can be useful for the adhesive material, e.g., glue, which attaches the splint to the prosthesis 602 and the adjacent teeth 605. An adhesive that needs to attach to a smooth splint surface may not provide enough stability since no hold points are provided for the adhesive to attach to. The holes through the splint enhance the adhesive in attaching to the splint. The adhesive material can propagate into the holes or the perforations and, after having changed into solid state, provide additional mounting means between splint and prosthesis or adjacent teeth respectively.

Figure 85:
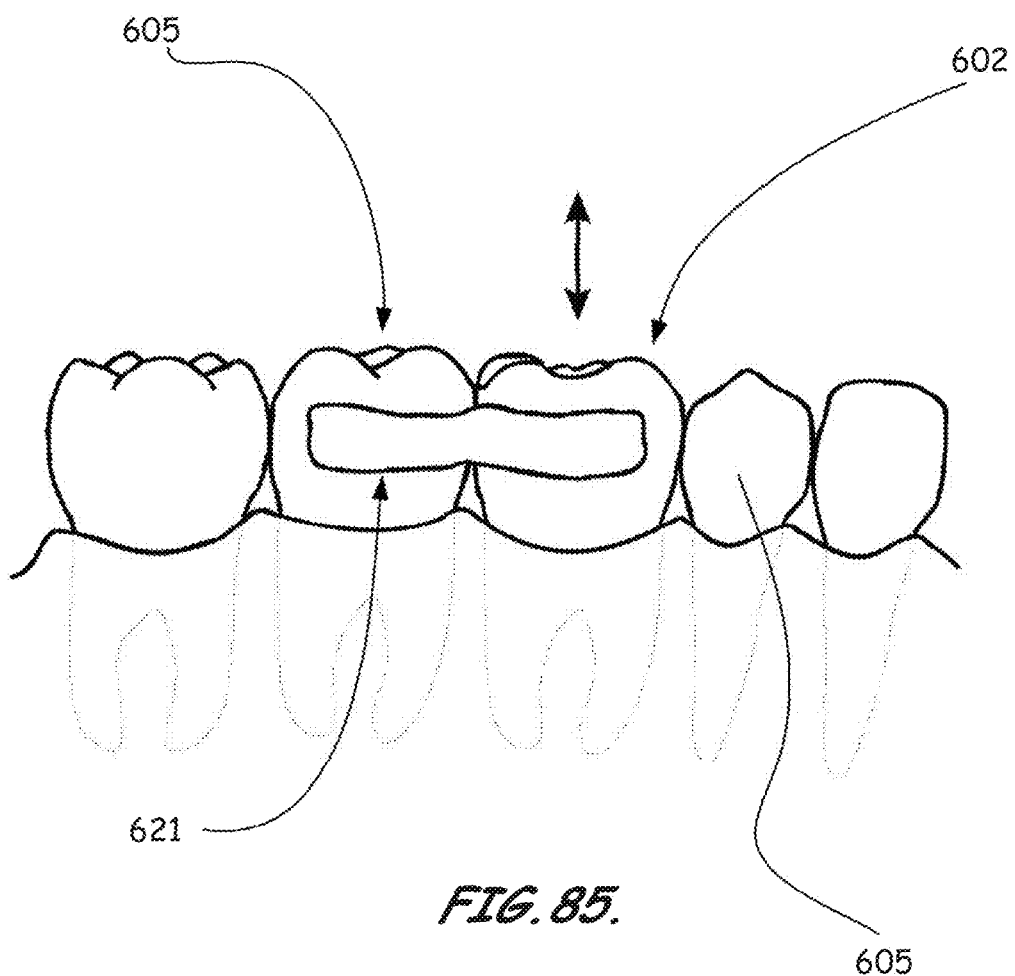
FIG. 85 illustrates a splint which is attached only to one of the adjacent teeth, according to an embodiment of the present invention.

Another embodiment of the present invention is depicted in FIG. 85. Therein, the splint 621 is designed in a way that it is attached to the dental prosthesis 602 and to one of the adjacent teeth 605. Such a splint design can be useful in cases where the other adjacent tooth 605 on the opposite side of the prosthesis 602 is not qualified for the attachment of a wing of the splint 607.

Figure 86:
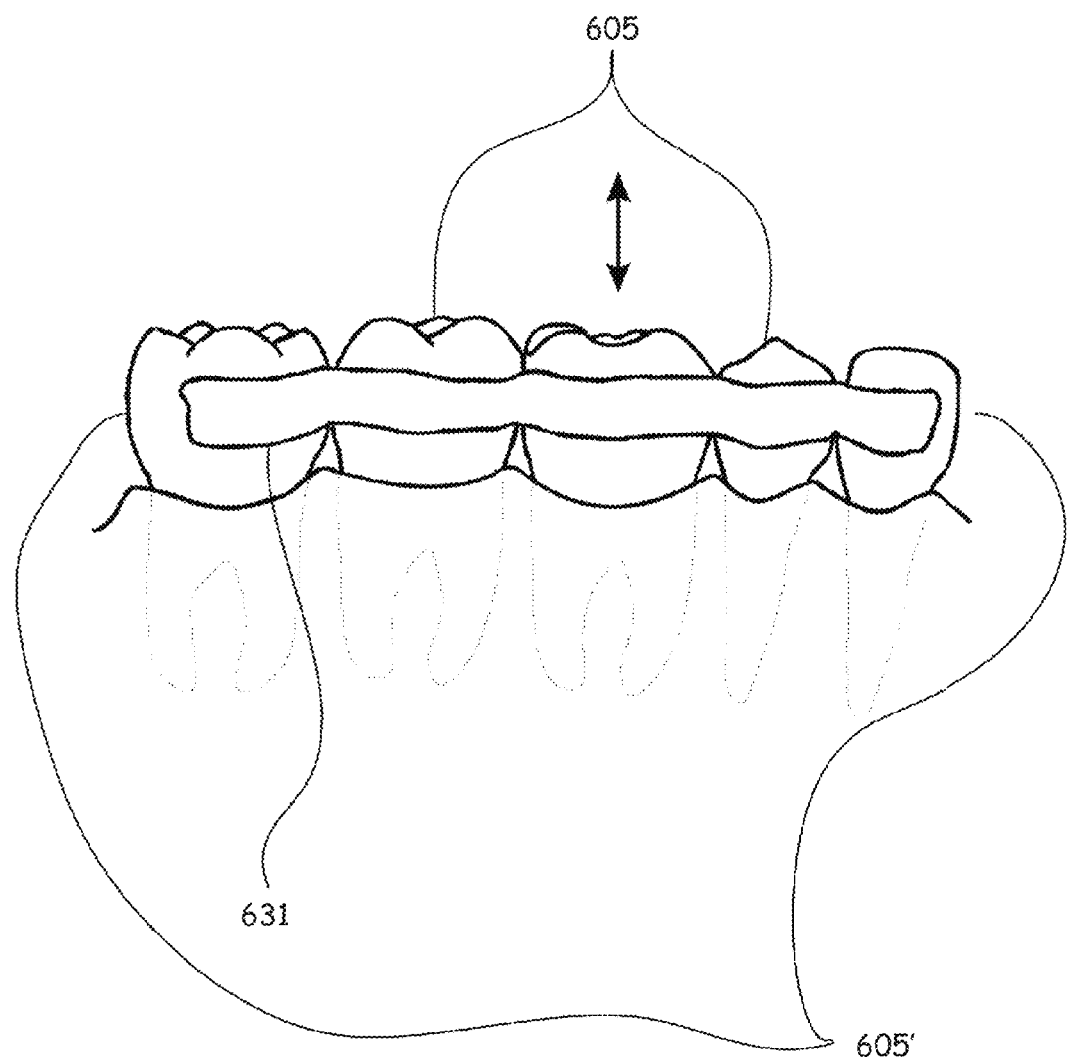
FIG. 86 illustrates a splint being attached to the adjacent teeth and teeth next to the adjacent teeth, according to an embodiment of the present invention.

Another embodiment of the present invention is depicted in FIG. 86. This embodiment is characterized by a splint 631 which is not only attached to the prosthesis 602 and the adjacent teeth 605 but also to the next teeth 605' adjacent to the adjacent teeth 605 of the dental prosthesis 602. Such an embodiment of the splint 607 can be useful when the two directly adjacent teeth 605 are not qualified for providing primary stability to the prosthesis 602 via the splint. The enhanced splint 631, therefore, makes use of the stability of the next teeth 605' adjacent to the adjacent teeth 605. Any combination of the foregoing is possible to reflect limitations of the dental anatomy of interest, attaching the prosthesis to one or more adjacent teeth, on one or either side of the prosthesis.

Figure 87:
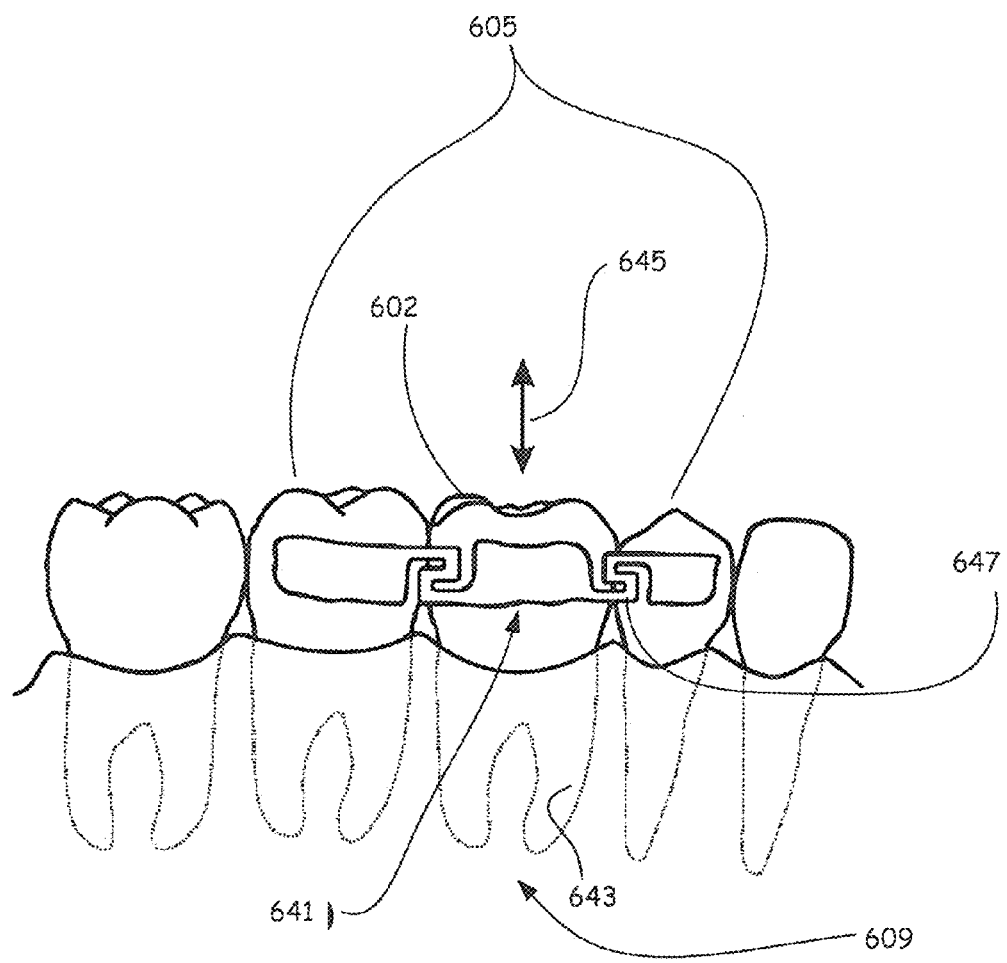
FIG. 87 is a perspective and part environmental view of a customized elastic splint design/modification according to an embodiment of the present invention.

FIG. 87 illustrates a custom-shaped splint 641 attached to the customized dental prosthesis 602 and the two adjacent teeth 605. The design and fabrication of such a splint 641 is based on the imaging data of, for example, the extracted tooth. The splint 641 is used to position and orient the prosthesis 602 in the dental structure 609 building the extraction void 643 in geometrical relation to the adjacent teeth 605. Similar to the splint 607 shown in FIG. 78, the splint 641 is connected with adhesive means to the prosthesis 602 and the adjacent teeth 605. In contrast to the splint 607, the splint 641 is designed in a way that it provides elasticity in vertical direction 645. This elasticity is achieved by an elastic or spring-type connection 647. Beneficially, the prosthesis 602 can immediately be used in the day-to-day use of mastication in which forces are applied to the adjacent teeth 605 and transmitted over the elastic/spring-type connection 647 to the dental prosthesis 602. Thereby, a certain level of micro-movement is applied to the dental prosthesis 602. This movement can serve to enhance the process of either perio-type or osseointegration.

Figure 88:
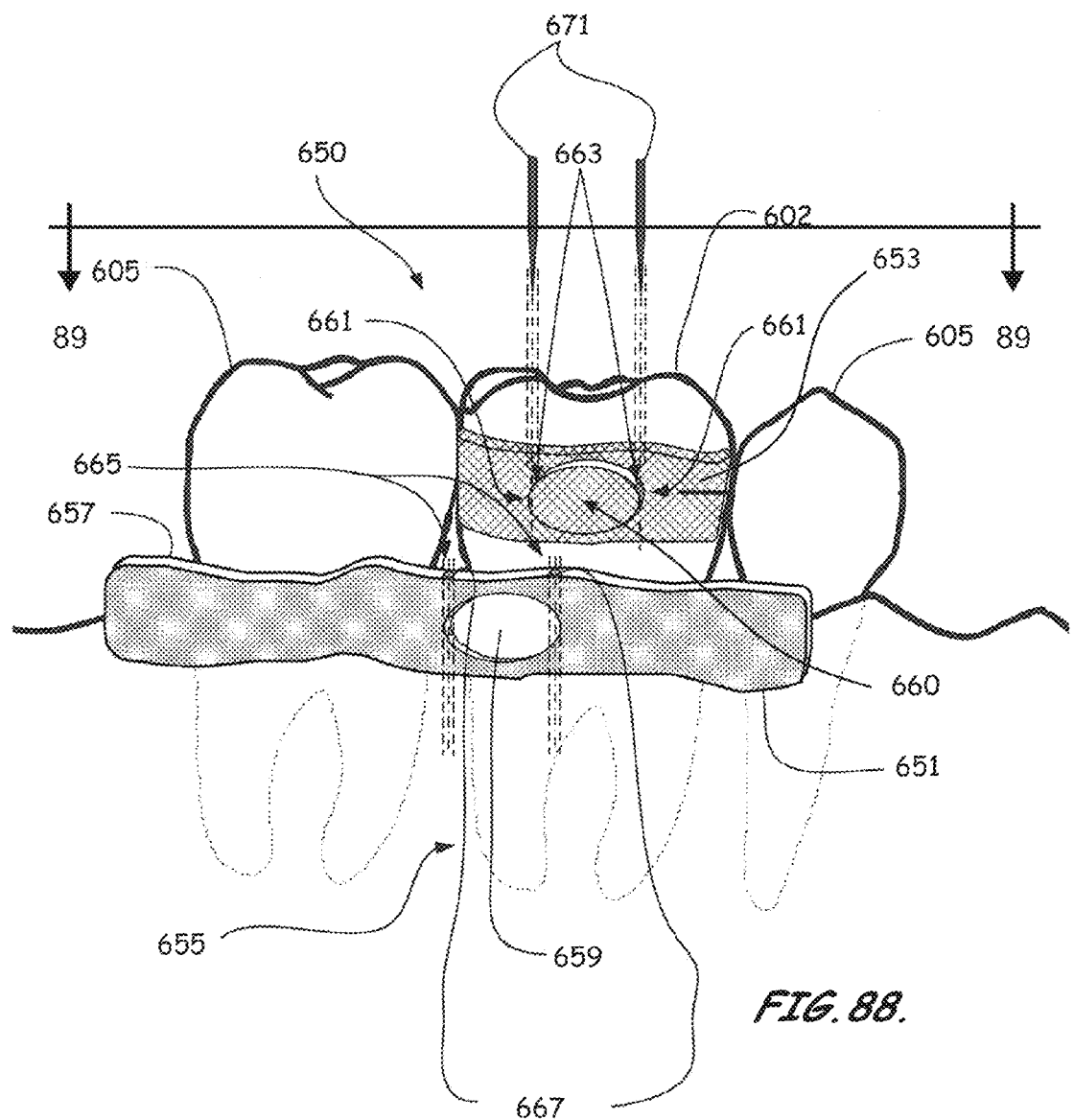
FIG. 88 is a perspective and part environmental view of a detachable two-part splint assembly according to an embodiment of the present invention.

FIG. 88 illustrates a customized detachable splint assembly 650 (including a bridge portion 651 and prosthesis attachment 653) adapted to be aligned to be attached to the customized dental prosthesis 602 and the two adjacent teeth 605. In an exemplary configuration, the attachment portion 653 shown connected to the dental prosthesis 602 is pre-assembled together with the dental prosthesis 602 by adhesive means. In an alternative embodiment, the attachment portion is an integral part of a temporary crown adhesively connected to an abutment portion and a root portion of the dental prosthesis. Thereby, the dental prosthesis 602 with the attachment portion 653 can be adjusted during the implantation procedure and correctly positioned in the alveole 655. When the dental prosthesis 602 is correctly positioned in the alveole 655 and between the surrounding adjacent teeth 605, the bridge portion 651 is attached to the attachment 653 and to the adjacent teeth through its flanks 657. This is achieved by sliding the bridge portion 651 sideways in a way that the elliptic cut 659 surrounds the elliptic attachment portion 660. The elliptic attachment portion 660 has an outer surface size and shape matching an inner surface size and shape of the elliptic cut 659. The attachment portion 653 provides two recesses 661 that proceed vertically downwards from the upper ends 663 of the elliptic attachment portion 660, vertically downwards. The bridge portion 651 contains two holes 665 that proceed from the upper ends 667 vertically downwards. After the bridge portion 651 is attached to the attachment portion 653, two pins 671 are pressed into the holes 665, thereby, firmly connecting and fixing the attachment portion 653 to the bridge portion 651. Note, the elliptic shape is provided by way of example. Additional shapes are within the scope of the present invention.

Figures 89, 90:
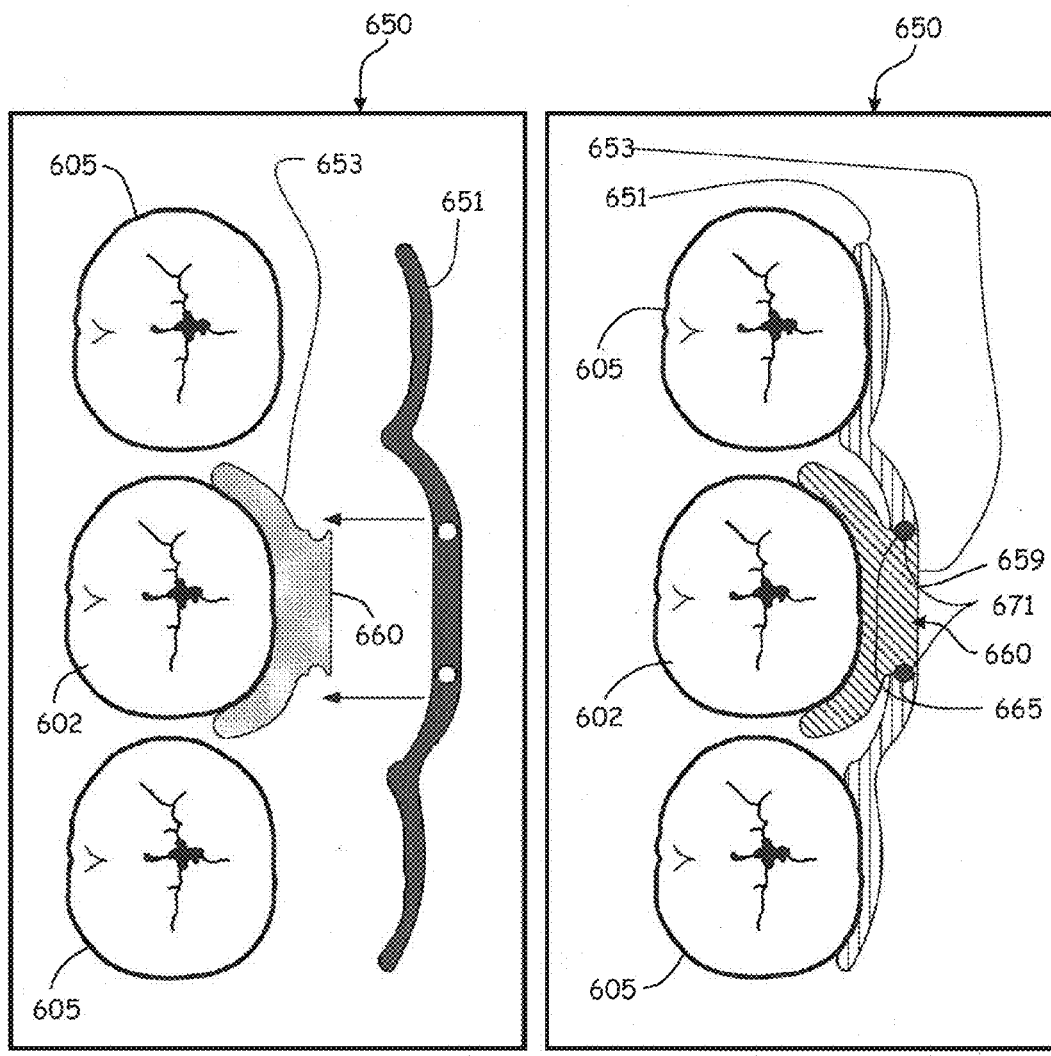
FIGS. 89-90 provide a sectional view of the detachable two-part splint assembly of FIG. 88 according to an embodiment of the present invention.

FIG. 89 shows the detachable splint assembly 650 viewed along the 89-89 line in FIG. 88 from a plan view in a pre-assembly condition—i.e., the bridge portion 651 is unattached to the prosthesis attachment portion 653. The figure further illustrates the step of aligning the elliptic cut 659 of the bridge portion 651 with the elliptic attachment portion 660 of prosthesis attachment 653 for connection thereto. In FIG. 90, the bridge portion 651 is firmly attached to the prosthesis attachment portion 653. With elliptical attachment portion 660 inserted through the elliptical cut 659, the two pins 671 (see also FIG. 88) are pressed into the holes 665.

In another embodiment, the bridge portion 651 is attached to the two adjacent teeth 605 after extraction of the non-functional tooth of interest to serve as a positioning guide placed prior to the insertion of the assembly of prosthesis attachment portion 653 and the dental prosthesis 602 (or respectively the combined part including the prosthesis attachment portion 653 and the dental prosthesis 602) in the alveole 655. The undersized shape of the dental prosthesis 602 compared to the shape of the alveole 655 allows the user/clinician to first decline the assembly (or combined part) and pass the elliptic attachment portion 660 of prosthesis attachment 653 by the bridge portion 651. Second, due to the design, the user/clinician can incline the assembly (or combined part) towards the bridge portion 651 in order to insert the elliptical attachment portion 660 into the elliptical cut 659. Third, due to the design, the user/clinician can press the two pins 671 (see also FIG. 88) into the holes 665 to define the final position and orientation of the dental prosthesis 602 with respect to the alveole 655 and to provide primary stability by affixing the prosthesis attachment portion 653 and subsequently the dental prosthesis 602 to the two adjacent teeth 605.

In another exemplary embodiment, two prosthesis attachment portions (in analogy to 653) are directly bonded onto the two adjacent teeth 605, while the bridge portion 651 includes in addition to the elliptical cut 659 two further elliptical cuts (in analogy to 659) to receive the two aforementioned prosthesis attachment portions that are directly bonded onto the two adjacent teeth. With that, the two prosthesis attachment portions intended to be directly bonded onto the two adjacent teeth 605 can be adhesively bonded onto the two adjacent teeth 605 prior to the extraction of the non-functional tooth of interest, using the bridge portion 651 as a positioning guide. Then, the non-functional tooth of interest is extracted, and the assembly of prosthesis attachment portion 653 and the dental prosthesis 602 (or respectively the combined part including the prosthesis attachment portion 653 and the dental prosthesis 602) can be placed into the alveole 655. Finally, the bridge portion 651 is inserted so that the three elliptic attachment portions (one shown as 660 and to be made in analogy and bonded to the adjacent teeth) attach with the three elliptical cuts (one shown as 659 and two to be made in analogy to 659) of the bridge portion 651, so that when each such elliptical connection is secured with two pins 671, the final position and orientation of the dental prosthesis 602 with respect to the alveole 655 is achieved and the primary stability is provided.

In another exemplary configuration, the bridge portion 651 is pre-assembled (or combined) with the prosthesis attachment portion 653, which is pre-assembled (or combined) with the dental prosthesis 602, and the assembly (or the combined part) is inserted and affixed to the two prosthesis attachment portions being previously directly bonded onto the two adjacent teeth 605 as described before. A separate placement guide, similar to the single bride portion, can be used to place and adhesively bond the two prosthesis attachment portions onto the two adjacent teeth 605 prior to the extraction of the non-functional tooth of interest.

Note, according to various embodiments of the present invention, all specific embodiments discussed with the aforementioned various design features of the splint (e.g. 607, FIGS. 78A and 78B, 611 FIG. 84, 631, FIG. 86, 641, FIG. 87, 651, FIGS. 88, 89 and 90) can be applied as they are applicable to design of the various embodiments of the integrated support device (e.g. 501, FIGS. 57 and 58, 521, FIGS. 59 to 66, 71, 72 and 77, 521', FIG. 71, 593, FIG. 76) and vice versa.

Miscellaneous

One of ordinary skill in the art will recognize that various aspects of the inventions as explained above can readily be combined with each other.

The meaning of "CAD" shall include but shall not be limited to any and all technology of computer aided design.

The meaning of "CAM" shall include but shall not be limited to any and all technology of computer aided manufacturing.

The meaning of "CNC" shall include but shall not be limited to any and all technology of computer numerical control as it relates to manufacturing machinery and systems, including but not limited to rapid prototyping devices and systems.

The meaning of "rapid prototyping" shall include but shall not be limited to all technologies qualified for manufacturing of copies of virtual three-dimensional objects and also technologies qualified for mass customization or the mass production of copies of customized or adapted geometries to the needs of an individual patient. Rapid prototyping in this context shall include but not be limited to manufacturing technologies based on the digital data, by a process that includes depositing material, in accordance with the digital data, layer-by-layer in a plurality of layers each constituting a two-dimensional cross section of a solid object having an edge defined by data of the three-dimensional surface, the layers being stacked in a third dimension to form the solid object having a three-dimensional surface defined by the data. All such rapid prototyping technologies can be used directly to manufacture the part of interest, for example, by selective laser sintering or indirectly by fabricating first, e.g., a resin or wax sample of the part of interest and second using for example, "lost-wax" casing to duplicate such sample and fabricate therewith the part of interest. It also includes sintering techniques where the "green" body is printed in response to computerized numerical controlled (CNC) data and then sintered to its final material properties. Sintering in this context includes pressure and heat.

The meaning of "rapid prototyping" shall be used in its broadest technical sense, where individualized parts are made from virtual representations, and shall include respective additive, subtractive and forming technologies used to three-dimensionally shape work pieces. The meaning of "additive shaping" shall include but shall not be limited to selective laser melting, selective laser sintering, stereolithography, 3-D printing or depositing of wax, wax-bound powders, adhesive-bound powders, slurries. The meaning of "subtractive shaping" shall include but shall not be limited to 3D laser shaping, CNC-grinding, CNC-turning, and CNC-milling technologies, and other machining and finishing technologies. The meaning of "shape forming" shall include but shall not be limited to near net-shape forming technologies, CNC-stamping, and CNC-pressing and casting technologies.

The meaning of "body" of an artificial tooth shall include but shall not be limited to the part of the prosthesis representing a root structure for perio-type or or osseointegration or the combined part of the prosthesis representing a root structure for perio-type or osseointegration and a support structure for a crown or a bridge.

The meaning of "prosthesis" shall include any substantially artificially shaped part of any natural and artificial material. In this sense a dental prosthesis for perio-type integration would have to be distinguished to any human tooth used for intentional re-implantation.

Whenever the context requires, the word "prosthesis" shall be deemed to include the word "implant" and vice versa.

"3D" shall mean three-dimensional.

The meaning of "CT" shall include but shall not be limited to any and all technology of computed tomography.

"CBCT" shall mean cone beam computed tomography and shall include "DVT" technology.

"DVT" shall mean digital volume tomography.

"Three-dimensional X-ray image" shall include but shall not be limited to voxel data, volumetric X-ray data, at least two two-dimensional X-ray images in DICOM format, a stack of two-dimensional X-ray images, data received from CBCT or other CT, MRT, ultrasonic and TOF devices, or any combination thereof.

The meaning of "MRT" shall include but shall not be limited to any and all technology of magnetic resonance tomography.

The meaning of "TOF" shall include but shall not be limited to any and all technology employing Time-of-Flight procedures.

The meaning of "imaging" and "scanning" shall include but shall not be limited to any and all technology of acquiring two-dimensional and/or three-dimensional data of physical objects or parts of a human body.

The meaning of clinical "imaging data" shall include but shall not be limited to in-vivo and in-vitro processes that result in any anatomical data of the anatomy of a human being. In this context the term data shall include but shall not be limited to two-dimensional and three-dimensional data.

The meaning of three-dimensional data shall include but shall not be limited to surface (e.g., triangulated data) and volumetric (e.g., voxel) data.

The meaning of "perio-type tissue" and "periodontal tissue" shall include but shall not be limited to any soft tissue surrounding a tooth.

The meaning of "perio-type ligature", "perio-type ligament" "periodontal ligature", "ligament" or "periodontal ligament" shall include but shall not be limited to the fibrous connective tissue interface usually located between a human tooth and the anatomical structure of the jaw of a human being.

The meaning of each one of the following: "perio-type integration", "parodontal integration", "integration into the periodont", "integration into the parodont", "integration into the dental soft-tissue", "integration into the dental ligament" and alike word constructions shall include but shall not be limited to the integration into the periodontal or perio-type ligament structure or other perio-type tissue or any other biological structure of the human dental anatomy except osseointegration. In this sense the term perio-type integration shall include but shall not be limited to the integration of a prosthesis to be adopted and held by periodontal and/or perio-type ligament tissue of a human being.

In this sense a prostheses for periodontal integration would have to be distinguished to any osseointegrated implant.

The meaning of "cavity" shall include but shall not be limited to the periodontal cavity, a cavity of the jaw bone structure, a cavity of the alveolus or a combination thereof.

The meaning of "extraction socket" shall include prepared or unprepared extraction sockets. The meaning of "prepared" shall include but shall not be limited to being surgically pared, abraded, scraped or curetted by mechanical instruments or laser technology based devices.

The meaning of "replacement", "to replace", "to be replaced" shall include but shall not be limited to any substitution, where one object fills the former position of another object. In the context of the foregoing such substitution can be performed at any time, so that for example, the term replacement shall not be limited to a replacement in a timely manner.

The meaning of a "manufactured one-piece" object shall not be limited to homogeneous objects, and shall include but shall not be limited to manufactured assemblies, objects that are coated, objects that are consisting of more than one pieces or materials bonded together or any combination thereof.

The meaning of a "clinical one-step" process or a "clinical one-step" method shall include but shall not be limited to a series clinical process or method steps performed in one or more clinical events as long as no further iteration is required that includes clinical process or method steps and process or method steps that cannot be performed chair-side.

The meaning of "immediate load" of an implant shall include but shall not be limited to any all integration concepts of implants where the occlusal portion of the implant (e.g., the crown portion facing the opponent jaw) is not protected against the alternate load of mastication by additional protective means.

The meaning of "configured to be integrated into the existing occlusion of the patients dentition" shall include but shall not be limited to any shaping of a crown or a crown-like portion of a prosthesis that contacts or otherwise substantially fills the gap between adjacent crowns, and any shaping that contacts or otherwise substantially interacts with the opponent crowns of the dentition in the process of masticating food.

In dentistry, the term occlusion is used to refer to the manner in which the teeth from upper and lower arches come together when the mouth is closed. The meaning of "occlusion" shall mean but shall not be limited to the manner the teeth of the upper or lower arch are fitting and coming in contact with each other while the mouth is closed or during chewing (articulation). It shall also include the fit and contact of adjacent teeth within one arch. The meaning of "integrated into the occlusion" shall include but shall not be limited to the configuration and integration of the fit and contact situation of a prosthesis within the existing or new build occlusion within the same and the opponent arch.

The words used in this specification to describe the invention and its various embodiments are to be understood not only in the sense of their commonly defined meanings, but to include by special definition in this specification structure, material or acts beyond the scope of the commonly defined meanings. Thus, if an element can be understood in the context of this specification as including more than one meaning, then its use in a claim must be understood as being generic to all possible meanings supported by the specification and by the word itself.

The various embodiments and aspects of embodiments of the invention disclosed herein are to be understood not only in the order and context specifically described in this specification, but to include any order and any combination thereof. Whenever the context requires, all words used in the singular number shall be deemed to include the plural and vice versa. Words which import one gender shall be applied to any gender wherever appropriate. Whenever the context requires, all options that are listed with the word "and" shall be deemed to include the world "or" and vice versa, and any combination thereof. The titles of the sections of this specification and the sectioning of the text in separated paragraphs are for convenience of reference only and are not to be considered in construing this specification.

Insubstantial changes from the claimed subject matter as viewed by a person with ordinary skill in the art, now known or later devised, are expressly contemplated as being equivalent within the scope of the claims. Therefore, obvious substitutions now or later known to one with ordinary skill in the art are defined to be within the scope of the defined elements.

In the drawings and specification, there have been disclosed embodiments of the invention, and although specific terms are employed, the terms are used in a descriptive sense only and not for purposes of limitation, the scope of the invention being set forth in the following claims. It must be understood that the illustrated embodiment has been set forth only for the purposes of example and that it should not be taken as limiting the invention. It will be apparent to those skilled in the art that alterations, other embodiments, improvements, details and uses can be made consistent with the letter and spirit of the disclosure herein and within the scope of this disclosure patent, which is limited only by the following claims, construed in accordance with the patent law, including the doctrine of equivalents. For example, the various enhancements to the splint embodiments such as the spring-type connection, among others, along with the manufacturing methodologies, are applicable to the various embodiments of the integrated support structure, and vice versa. Also for example, the various enhancements of the integrated support structure embodiments of, along with the manufacturing methodologies, are applicable to the various embodiments of the dental implant assembly/dental prosthesis described herein.

This patent application is a non-provisional of and claims priority to and the benefit of U.S. Provisional Patent Application No. 61/602,470, filed on Feb. 23, 2012, and is a continuation-in-part of U.S. Patent application Ser. No. 13/247,843, Sep. 28, 2011, and U.S. Patent application Ser. No. 13/247,607, filed Sep. 28, 2011, which claimed priority to and the benefit of U.S. Provisional Patent Application No. 61/454,450 filed on Mar. 18, 2011; and is related to U.S. Patent application Ser. No. 13/767,982, concurrently filed on Feb. 15, 2013, and U.S. Patent application Ser. No. 12/763,001, filed Apr. 19, 2010, which is a continuation-in-part of and claimed priority to and the benefit of US. Patent application Ser. No. 11/724,261, filed Mar. 15, 2007, now U.S. Pat. No. 7,708,557, which is a continuation-in-part of and claimed priority to and the benefit of co-pending U S. Patent application Ser. No. 11/549,782 filed on Oct. 16, 2006, each incorporated by reference in its entirety.

In the claims which follow, reference characters if used to designate claim steps are provided for convenience of description only, and are not intended to imply any particular order for performing the steps.

What is claimed is:

1. A system for providing temporary primary stability to a dental implant positioned in a jawbone cavity of a specific pre-identified patient, the system comprising:
   design data including a virtual model modeling a position and inclination of the dental implant in the jawbone cavity and in a geometrical relation to one or more adjacent functional teeth adjacent the jawbone cavity of the specific pre-identified patient;
   the dental implant, the dental implant being custom manufactured according to the design data; and
   an integrated support device, the integrated support device comprising:
   a prosthesis interface member configured to engage and land atop and surround substantial portions of an occlusal extending rising of a dental prosthesis component comprising the dental implant positioned within the jawbone cavity of the specific pre-identified patient, wherein an at least semirigid connection is formed between the prosthesis interface member and the occlusal extending rising to at least semirigidly fixate the prosthesis interface member to the occlusal extending rising to stabilize and provide primary stability to the dental implant, the prosthesis interface member and the dental prosthesis component forming a form-lock fit when placed together, wherein the prosthesis interface member includes an occlusal extending recess extending into a body of the prosthesis interface member, wherein an inner surface contour of the occlusal extending recess has an asymmetrical custom-shaped surface contour that is directly correlated to a corresponding portion of the occlusal-facing surface of the occlusal extending rising of the dental prosthesis component also having an asymmetrical custom-shaped surface contour, and wherein the asymmetrical custom-shaped surface contour of the occlusal-facing surface of the occlusal extending rising of the dental prosthesis component matches the shape of a virtual occlusal extending rising formed by reducing dimensions of a modeled virtual occlusally facing crown component modeling a crown of a tooth of the specific pre-identified patient to be replaced; and
   a bonding wing integral with the prosthesis interface member and configured to bond to a corresponding adjacent functional tooth adjacent the jawbone cavity when operably positioned thereon to at least substantially rigidly fixate the prosthesis interface member to stabilize and provide temporary primary stability to the dental implant and to maintain the dental implant at a position and inclination substantially the same as the modeled position and inclination included in the design data when the dental implant is positioned within and being integrated into the jawbone cavity of the pre-identified patient, the integrated support device shaped responsive to the design data and prior to its clinical integration adjacent the dental implant and the jawbone cavity of the specific pre-identified patient, the prosthesis interface member and bonding wing monolithically formed as one part, the prosthesis interface member entailing the bonding wing, and the bonding wing arising outwardly from a surface of the prosthesis interface member toward the corresponding adjacent functional tooth.

2. The system as defined in claim 1, wherein the dental prosthesis component is an assembly, including the dental implant and an abutment, wherein the occlusal extending rising of the dental prosthesis component being engaged by the prosthesis interface member is an occlusal extending rising of the abutment connected to the dental implant.

3. The system as defined in claim 1, wherein the prosthesis interface member comprises a temporary crown.

4. The system as defined in claim 1, wherein the prosthesis interface member includes an occlusal extending recess extending substantially into a body of the prosthesis interface member to define a complementing interface surface, and wherein an occlusal-facing surface of the occlusal extending rising and the complementing interface surface of the prosthesis interface member together create a form-lock fit when the occlusal-facing surface of the occlusal extending rising is operably positioned within the occlusal extending recess.

5. The system as defined in claim 1, wherein the prosthesis interface member includes an occlusal extending recess extending substantially into a body of the prosthesis interface member and having a three-dimensional asymmetric shape directly correlated with a three-dimensional asymmetric shape of substantial portions of the occlusal-facing surface of the occlusal extending rising of the dental prosthesis component.

6. The system as defined in claim 1,
wherein the prosthesis interface member comprises a crown portion custom manufactured for the specific pre-identified patient receiving the dental prosthesis component; and
wherein an outline of a cross-section of the crown portion custom manufactured for the pre-identified patient directly correlates to an outline of a corresponding cross-section of the occlusal extending rising of the dental prosthesis component.

7. The system as defined in claim 1, wherein the bonding wing is dimensioned to be sufficiently small so as to not extend atop a portion of an incisal surface of the respective adjacent functional tooth that is normally aligned to contact a surface of a corresponding opposite-facing functional tooth when the respective tooth is an anterior tooth, and so as to not extend atop a portion of an occlusal surface of the respective adjacent functional tooth that is normally aligned to contact an occlusal surface of a corresponding opposite-facing functional tooth when the respective tooth is a posterior tooth.

8. The system as defined in claim 1, wherein the bonding wing includes a tooth-facing outer surface portion adapted to adhesively bond to an outer surface portion of a crown of the adjacent functional tooth and having a custom three-dimensional surface shape dimensioned to substantially match a three-dimensional shape of the outer surface portion of the crown of the adjacent functional tooth, the tooth-facing outer surface portion having the custom three-dimensional surface shape prior to insertion of the dental implant into the jawbone, prior to application of bonding material to the tooth-facing outer surface portion, and prior to bonding attachment of the tooth-facing outer surface portion to the outer surface portion of the crown of the adjacent functional tooth, determined using imaging data.

9. The system as defined in claim 1, wherein the bonding wing is a first bonding wing, wherein the adjacent functional tooth is a first adjacent functional tooth, and wherein the integrated support device further comprises:
a substantially rigid second bonding wing integral with the prosthesis interface member and configured to bond to a corresponding second adjacent functional tooth located opposite the first adjacent functional tooth to at least substantially rigidly fixate the prosthesis interface member to thereby stabilize the dental implant in a user desired position and inclination and provide temporary primary stability to the dental implant when the dental implant is being integrated into the jawbone cavity.

10. The system as defined in claim 9, wherein the second bonding wing includes a tooth-facing outer surface portion adapted to adhesively bond to an outer surface portion of a crown of the second adjacent functional tooth and having a custom three-dimensional surface shape dimensioned to substantially match a three-dimensional shape of the outer surface portion of the crown of the second adjacent functional tooth, the tooth-facing outer surface portion having the custom three-dimensional surface shape prior to insertion of the dental implant into the jawbone, prior to application of bonding material to the tooth-facing outer surface portion, and prior to bonding attachment of the tooth-facing outer surface portion to the outer surface portion of the crown of the adjacent functional tooth, determined using imaging data.

11. A system for providing temporary primary stability to a dental implant positioned in a jawbone cavity of a specific pre-identified patient, the system comprising:
design data including a virtual model modeling a position and inclination of the dental implant in the jawbone cavity of the specific pre-identified patient the dental implant, the dental implant being custom manufactured according to the design data; and
an integrated support device, the integrated support device comprising:
a prosthesis interface member configured to engage and land atop and surround substantial portions of an occlusal-facing surface of an occlusal extending portion of a dental prosthesis component connected to or integral with the dental implant, wherein an at least semirigid connection is formed between the prosthesis interface member and the occlusal extending rising to at least semirigidly fixate the prosthesis interface member to the occlusal extending rising to stabilize and provide primary stability to the dental implant, the prosthesis interface member and the dental prosthesis component forming a form-lock fit when placed together, wherein the prosthesis interface member includes an occlusal extending recess extending into a body of the prosthesis interface member, wherein an inner surface contour of the occlusal extending recess has an asymmetrical custom-shaped surface contour that is directly correlated to a corresponding portion of the occlusal-facing surface of the occlusal extending rising of the dental prosthesis component also having an asymmetrical custom-shaped surface contour, and wherein the asymmetrical custom-shaped surface contour of the occlusal-facing surface of the occlusal extending rising of the dental prosthesis component matches the shape of a virtual occlusal extending rising formed by reducing dimensions of a modeled virtual occlusally facing crown component modeling a crown of a tooth of the specific pre-identified patient to be replaced; and
a bonding wing substantially rigidly connected to or integral with the prosthesis interface member and configured to bond to a corresponding adjacent functional tooth adjacent the jawbone cavity when operably positioned thereon to at least substantially rigidly fixate the prosthesis interface member to thereby stabilize the dental implant in a position and inclination substantially the same as the modeled position and inclination included in the design data and provide temporary primary stability to the dental implant when the dental implant is positioned within the jawbone cavity, the prosthesis interface member and bonding wing monolithically formed as one part, the prosthesis interface member entailing the bonding wing, and the bonding wing arising outwardly from a surface of the prosthesis interface member toward the corresponding adjacent functional tooth.

12. The system as defined in claim 11, wherein the occlusal extending portion of the dental prosthesis component being engaged by the prosthesis interface member comprises an occlusal extending rising of an abutment connected to the dental implant.

13. The system as defined in claim 11, wherein the prosthesis interface member comprises a temporary crown.

14. The system as defined in claim 11, wherein the prosthesis interface member includes an occlusal extending recess extending substantially into a body of the prosthesis interface member to define a complementing interface surface, and wherein the occlusal-facing surface of the occlusal extending portion and the complementing interface surface of the prosthesis interface member together create a form-lock fit when the occlusal-facing surface of the occlusal extending portion is operably positioned within the occlusal extending recess.

15. The system as defined in claim 11, wherein the prosthesis interface member includes an occlusal extending recess extending substantially into a body of the prosthesis interface member and having a three-dimensional asymmetric shape directly correlated with a three-dimensional asymmetric shape of substantial portions of the occlusal-facing surface of the occlusal extending portion of the dental prosthesis component.

16. The system as defined in claim 11,
wherein the prosthesis interface member comprises a crown portion custom manufactured for the specific pre-identified patient receiving the dental implant; and
wherein an outline of a cross-section of the crown portion custom manufactured for the pre-identified patient directly correlates to an outline of a corresponding cross-section of the occlusal extending portion of the dental prosthesis component.

17. The system as defined in claim 11, wherein the adjacent functional tooth is an anterior tooth, and wherein the bonding wing extends atop a portion of an incisal surface of the adjacent functional tooth, the portion extending atop the incisal surface being dimensioned to avoid extension over any portion of the incisal surface that is normally aligned to contact a surface of a corresponding opposite-facing functional tooth as determined by imaging data.

18. The system as defined in claim 11, wherein the adjacent functional tooth is a posterior tooth, and wherein the bonding wing extends atop a portion of an occlusal surface of the respective adjacent functional tooth, the portion extending atop the occlusal surface being dimensioned to avoid extension over any portion of the occlusal surface that is normally aligned to contact an occlusal surface of a corresponding opposite-facing functional tooth as determined by imaging data.

19. The system as defined in claim 11, wherein the bonding wing is dimensioned to be sufficiently small so as to not extend atop a portion of an incisal surface of the respective adjacent functional tooth that is normally aligned to contact a surface of a corresponding opposite-facing functional tooth when the respective tooth is an anterior tooth, and so as to not extend atop a portion of an occlusal surface of the respective adjacent functional tooth that is normally aligned to contact an occlusal surface of a corresponding opposite-facing functional tooth when the respective tooth is a posterior tooth.

20. The system as defined in claim 11, wherein the bonding wing includes a tooth-facing outer surface portion adapted to adhesively bond to an outer surface portion of a crown of the adjacent functional tooth and having a custom three-dimensional surface shape dimensioned to substantially match a three-dimensional shape of the outer surface portion of the crown of the adjacent functional tooth, the tooth-facing outer surface portion having the custom three-dimensional surface shape prior to insertion of the dental implant into the jawbone, prior to application of bonding material to the tooth-facing outer surface portion, and prior to bonding attachment of the tooth-facing outer surface portion to the outer surface portion of the crown of the adjacent functional tooth, determined using imaging data.

21. The system as defined in claim 11, wherein the bonding wing is a first bonding wing and wherein the adjacent functional tooth is a first adjacent functional tooth, the integrated support device comprising:
a second bonding wing substantially rigidly connected to or integral with the prosthesis interface member and configured to bond to a corresponding second adjacent functional tooth adjacent the jawbone cavity when operably positioned thereon to at least substantially rigidly fixate the prosthesis interface member to thereby stabilize the dental implant in a user desired position and inclination and provide primary stability to the dental implant when the dental implant is being integrated into the jawbone cavity.

22. The system as defined in claim 21, wherein the second bonding wing includes a tooth-facing outer surface portion adapted to adhesively bond to an outer surface portion of a crown of the second adjacent functional tooth and having a custom three-dimensional surface shape dimensioned to substantially match a three-dimensional shape of the outer surface portion of the crown of the second adjacent functional tooth, the tooth-facing outer surface portion having the custom three-dimensional surface shape prior to insertion of the dental implant into the jawbone, prior to application of bonding material to the tooth-facing outer surface portion, and prior to bonding attachment of the tooth-facing outer surface portion to the outer surface portion of the crown of the adjacent functional tooth, determined using imaging data.

23. A dental system comprising:
design data including a virtual model modeling a dental implant and a virtual model of a position and inclination of the dental implant in a jawbone cavity of a specific pre-identified patient in a geometrical relation to one or more adjacent teeth of the specific pre-identified patient adjacent the jawbone cavity;
the dental implant, the dental implant being custom manufactured according to the design data; and
an integrated support device, the integrated support device comprising:
a prosthesis interface member configured to surround substantial portions of an occlusal-facing surface of an occlusal extending portion of a dental prosthesis component connected to or integral with the dental implant, wherein an at least semirigid connection is formed between the prosthesis interface member and the occlusal extending portion to at least semirigidly fixate the prosthesis interface member to the occlusal extending portion to stabilize and provide primary stability to the dental implant, the prosthesis interface member and the dental prosthesis component forming a form-lock fit when placed together, wherein the prosthesis interface member includes an occlusal extending recess extending into a body of the prosthesis interface member, wherein an inner surface contour of the occlusal extending recess has an asymmetrical custom-shaped surface contour that is directly correlated to a corresponding portion of the occlusal-facing surface of the occlusal extending rising of the dental prosthesis component also having an asymmetrical custom-shaped surface contour, and wherein the asymmetrical custom-shaped surface contour of the occlusal-facing surface of the occlusal extending rising of the dental prosthesis component matches the shape of a virtual occlusal extending rising formed by reducing dimensions of a modeled virtual occlusally facing crown component modeling a crown of a tooth of the specific pre-identified patient to be replaced, and a bonding wing substantially rigidly connected to or integral with the prosthesis interface member and configured to bond to one or more corresponding adjacent crowns adjacent the jawbone cavity when operably positioned thereon, the prosthesis interface member and bonding wing monolithically formed as one part, the prosthesis interface member entailing the bonding wing, and the bonding wing arising outwardly from a surface of the prosthesis interface member toward the one or more corresponding adjacent crowns;

the integrated support device shaped responsive to the design data; and the integrated support device shaped prior to its clinical integration adjacent the dental implant and the jawbone cavity of the specific pre-identified patient.

24. The dental system as defined in claim 23, wherein the prosthesis interface member comprises a temporary crown.

25. The dental system as defined in claim 23, wherein the dental implant is shaped responsive to the design data.

26. The dental system as defined in claim 25, further comprising:

imaging data of the specific pre-identified patient, including a virtual representation of the jawbone cavity and a virtual representation of one or more adjacent teeth of the specific pre-identified patient, wherein the design data are derived from the imaging data.

27. The dental system as defined in claim 23, wherein the prosthesis interface member is configured to engage with substantial portions of the occlusal extending portion of the dental prosthesis component connected to or integral with the dental implant.

28. The dental system as defined in claim 27, wherein an occlusal-facing surface of an occlusal extending rising and a complementing apical-facing interface surface forming an occlusal-extending recess of the prosthesis interface member together create a form-lock fit when the occlusal-facing surface of the occlusal-extending rising is operably positioned within the apical-facing occlusal-extending recess of the prosthesis interface member.

29. The dental system as defined in claim 27, wherein the prosthesis interface member and the dental prosthesis component connected to or integral with the dental implant are assembled prior to a clinical integration of the dental implant into the jawbone cavity of the specific pre-identified patient.

* * * * *